(12) United States Patent
Patel et al.

(10) Patent No.: US 10,940,205 B2
(45) Date of Patent: Mar. 9, 2021

(54) COMPOSITIONS OF PHARMACEUTICAL ACTIVES CONTAINING DIETHYLENE GLYCOL MONOETHYL ETHER OR OTHER ALKYL DERIVATIVES

(71) Applicant: THEMIS MEDICARE LIMITED, Mumbai (IN)

(72) Inventors: Dinesh Shantilal Patel, Mumbai (IN); Sachin Dinesh Patel, Mumbai (IN); Shashikant Prabhudas Kurani, Mumbai (IN); Madhavlal Govindlal Patel, Mumbai (IN)

(73) Assignee: THEMIS MEDICARE LIMITED, Mumbai (IN)

( * ) Notice: Subject to any disclaimer, the term of this patent is extended or adjusted under 35 U.S.C. 154(b) by 41 days.

(21) Appl. No.: 15/801,390

(22) Filed: Nov. 2, 2017

(65) Prior Publication Data
US 2018/0071390 A1 Mar. 15, 2018

Related U.S. Application Data

(62) Division of application No. 14/242,973, filed on Apr. 2, 2014, now Pat. No. 9,827,315.

(30) Foreign Application Priority Data

Apr. 2, 2013 (IN) .................... IN1287/MUM/2013

(51) Int. Cl.
| | |
|---|---|
| *A61K 47/10* | (2017.01) |
| *A61K 9/00* | (2006.01) |
| *A61K 31/167* | (2006.01) |
| *A61K 31/4439* | (2006.01) |
| *A61K 31/565* | (2006.01) |
| *A61K 31/57* | (2006.01) |
| *A61K 31/573* | (2006.01) |
| *A61K 9/06* | (2006.01) |
| *A61K 9/08* | (2006.01) |
| *A61K 9/48* | (2006.01) |

(52) U.S. Cl.
CPC ............ *A61K 47/10* (2013.01); *A61K 9/0014* (2013.01); *A61K 9/0019* (2013.01); *A61K 9/0048* (2013.01); *A61K 9/06* (2013.01); *A61K 9/08* (2013.01); *A61K 9/4858* (2013.01); *A61K 31/167* (2013.01); *A61K 31/4439* (2013.01); *A61K 31/565* (2013.01); *A61K 31/57* (2013.01); *A61K 31/573* (2013.01); *Y02A 50/30* (2018.01)

(58) Field of Classification Search
CPC ....................................................... A61K 47/10
See application file for complete search history.

(56) References Cited

U.S. PATENT DOCUMENTS

| | | | | |
|---|---|---|---|---|
| 8,128,913 | B1 * | 3/2012 | Roszell ................ | A61K 8/8164 424/59 |
| 9,789,041 | B2 * | 10/2017 | Gross ..................... | A61K 36/76 |
| 2010/0215726 | A1 * | 8/2010 | Roth ........................ | A61K 8/64 424/450 |

* cited by examiner

*Primary Examiner* — Marcos L Sznaidman
(74) *Attorney, Agent, or Firm* — Ladas & Parry LLP

(57) ABSTRACT

The present invention relates to pharmaceutical compositions of various pharmaceutical actives, especially lyophilic and hydrophilic actives containing Diethylene glycol monoethyl ether or other alkyl derivatives thereof as a primary vehicle and/or to pharmaceutical compositions utilizing Diethylene glycol monoethyl ether or other alkyl derivatives thereof as a primary vehicle or as a solvent system in preparation of such pharmaceutical compositions. The pharmaceutical compositions of the present invention are safe, non-toxic, exhibits enhanced physical stability compared to conventional formulations containing such pharmaceutical actives and are suitable for use as injectables for intravenous and intramuscular administration, as well as for use as a preformed solution/liquid for filling in and preparation of capsules, tablets, nasal sprays, gargles, dermal applications, gels, topicals, liquid oral dosage forms and other dosage forms.

11 Claims, 1 Drawing Sheet

Sensor application method at injection site

COMPOSITIONS OF PHARMACEUTICAL ACTIVES CONTAINING DIETHYLENE GLYCOL MONOETHYL ETHER OR OTHER ALKYL DERIVATIVES

CROSS REFERENCE APPLICATIONS

This application is a Divisional of U.S. Ser. No. 14/242,973 filed Apr. 2, 2014 which claims the benefit of Indian Application No. 1287/MUM/2013 filed Apr. 2, 2013, the content of which is incorporated by reference.

FIELD OF THE INVENTION

The present invention relates to pharmaceutical compositions of various pharmaceutical actives containing Diethylene glycol monoethyl ether or other alkyl derivatives thereof as a primary vehicle and/or to pharmaceutical compositions utilizing Diethylene glycol monoethyl ether or other alkyl derivatives thereof as a primary vehicle or as a solvent system in preparation of such pharmaceutical compositions. The present invention especially relates to pharmaceutical compositions of lipophilic and hydrophilic actives containing Diethylene glycol monoethyl ether or other alkyl derivatives thereof as a primary vehicle and/or to pharmaceutical compositions utilizing Diethylene glycol monoethyl ether or other alkyl derivatives thereof as a primary vehicle or as a solvent system in preparation of such pharmaceutical compositions. The pharmaceutical compositions of the present invention are safe, non-toxic, exhibits enhanced physical stability compared to conventional formulations containing such pharmaceutical actives and are suitable for use as injectables for intravenous and intramuscular administration, as well as for use as a preformed solution/liquid for filling in and preparation of capsules, tablets, nasal sprays, gargles, dermal applications, gels, topicals, liquid oral dosage forms and other dosage forms.

BACKGROUND OF THE INVENTION

Formulation of various pharmaceutical actives, especially lipophilic actives is a problem because many such actives are difficult to solubilize, by virtue of their poor solubility; because many formulations containing such actives have poor stability and hence are difficult to manufacture and in many instances require such formulations to be lyophilized or freeze dried; and because many formulations containing such actives are required to be formulated as emulsions and hence difficult to manufacture. This is especially true for formulations of such actives in the form of injectables, capsules, gargles, solutions etc and other dosage forms. Preparation of various lipophilic drugs that are poorly soluble or insoluble in water/other solvents in soluble pellucid has been a continuing problem in the art.

Examples of such pharmaceutical actives, useful in various physiological conditions to alleviate the pathology caused due to various disease conditions are the following, which are not restrictive and a person of skill in the art may select other compounds which fall into the aforementioned categories:
I) Steroids and Hormones;
II) Antimalarial agents;
III) Proton Pump Inhibitors;
IV) Analgesic Agents (NSAIDs and Narcotic Analgesics);
V) COX 2 Inhibitors;
VI) Hypnotic Agents;
VII) Antifungal Agents;
VIII) Oxicams;
IX) ACE Inhibitors;
X) Muscle Relaxants;
XI) Antibiotics;
XII) Aldosterone Receptor Antagonists;
XIII) Cardiovascular Agents;
XIV) Calcium Channel Blockers;
XV) Anti-arrhythmic Agents;
XVI) Cardiac Glycosides and other Drugs related to CVS;
XVII) Antipsychotic Agents;
XVIII) Anticonvulsants;
XIX) Diuretics;
XX) Anticancer Agents;
XXI) Immunosuppressants;
XXII) Vitamins and Minerals; and
XXIII) Peptides In the past, numerous agents have been used to solubilize various categories of drugs. The use of organic solvents like Acetone, Methanol, Ethyl acetate, Tetrahydrofuran, Chloroform, Hexane, etc., for their subsequent use either as oral or injectable (intramuscularly or intravenously) is prohibited.

Use of oil and its derivatives has its limitations as these are derived from plant origin like sesame oil, cottonseed oil etc., which poses stability problems because their quality changes with season, may get unstable/rancid as well as their bulky viscous nature result in pain and further complication during application at the injecting site.

Manufacture of injectables using oil and its derivative also leads to problems from a quality control point of view. The tendencies of seasonal changes in oil quality (rancidity) and color change were problems encountered by manufacturing chemists. The pesticide residue from oil of natural origin is a potential risk factor for injectable forms. Further sterilization and difficulties during filtration are the added secondary problems.

Use of emulsions for solubilizing various drugs was also attempted. But the stability of emulsions, its particle size and sterility resulted in high cost of production. Moreover, various technologies are developed for administration in the injectable form and also pose the problems of pain at the site of the injection.

The abovementioned factors limit the use of oil as well as oil/water emulsions as solubilizing agents for the preparation of various categories of active drugs. Moreover, some of the derivatives of oil cause anaphylactic shocks and histamine release, thus reducing their usage.

The use of fatty acids and its derivative also requires special quality control and their therapeutic use in oral and injectable forms are therefore limited. Use of polyethylene glycol derivatives are quite high but there are limitations to their use as they can be administered up to certain levels only and are toxic at higher levels. Thus they become specific either for oral or local applications and their use is limited in injectables.

Further, the problems associated with oil-based injections are many, such as for instance a small test dose prior to actual administration is usually required to confirm tolerability of both active and oily vehicle; it causes pain, erythema and swelling at the site of injection; it leads to nodule formation at the site of injection; it is associated with a risk of damage to nerves, arteries or veins if improperly given or administered; if side effects occur they would be prolonged until plasma levels fall—hence the necessity for a test dose; it can take several weeks for plasma levels to reach steady state; injection technique competency, assessment and training are required; there are logistical difficulties for administering to a patient who is employed; there is a need for stabilizers and preservatives in larger amounts in such formulations for maintaining stability of the oily injections; some people have dislike or phobia of pain from the needles of such injectables; there could be staffing and medicine storage issues; it is viewed by some as stigmatizing and coercive, etc.

It is also found that there are some drugs available in the lyophilized form and the doctor/physician requires other pack of solvents to reconstitute before an administration. The technique of lyophilization is a costly process and unviable, leading many of such drugs uneconomical to patients.

Many drugs that are oil soluble have limited application as only to be administered intramuscularly and not used for ocular or intravenous purpose.

Complications associated with intramuscular injections are also many, such as they cause skin and tissue trauma; muscle fibrosis and contracture; nerve palsies, paralysis; anaphylactic shock; formation of thrombosis in veins; thrombo phlebitis; can involve infectious processes and cause abscesses or gangrene.

The formulation of drugs used for application as "Eye drops" in form of suspension/emulsions is limited because of their limited solubility in the aqueous media. Quality control attributes like stability, particulate matter, particle size etc., for such emulsions and suspensions, are the problems that are encountered by chemists during their preparation and application as "Eye drops".

The problems associated with parenteral suspension formulations are also many, such as typically they limit the formulator in selecting the ingredients, which are parenterally acceptable as suspending agents, viscosity inducing agents, wetting agents and preservatives; they are difficult to manufacture—special facilities are required to maintain aseptic conditions for manufacturing such as crystallization, particle size reduction, wetting, sterilization etc.; stability of the formulations during the period between manufacture and use resulting in many occasions in settlement of solids, caking, causing difficulty in redispersion etc.; difficulty in maintenance of physical stability; non-uniformity of dose at the time of administration; vials to be shaken for uniformity prior to use; necessity of ensuring or ruling out of clumping or granular appearance of the suspension before withdrawing into syringes; after withdrawal, the injections are to be applied as soon as possible before its starts settling in the syringe, with the result that the entire problems can be an issue for the doctor/physician.

Many drugs for solubilization require milling or micronization to enhance the solubility in the solubilizing agents. For instance, steroids require micronization to solubilize in oil or its derivatives or in a co-solvent. The use of co-solvents or other additives in oil type product adds up difficulty in administration due to viscosity and may also cause hemolysis if not used in appropriate acceptable concentration in the body particularly for the parenteral preparation.

Thus the formulation of a clear solution of drugs for therapy has always been challenge with the need of a solubilizer to give clear solution.

It is known that ethanol is often used in varying amounts up to 50-60% for solubilization of many drugs during their preparation. However, if it is used for therapeutic application in the concentration through intravenous, intramuscular or for oral delivery, then it may lead to intoxication leading to its restrictions.

The use of Propylene Glycol is also limited. The safety regarding its parenteral application is only up to 40%, that too also through Intramuscular route and is considered as hemolytic and toxic at higher concentration to the central nervous system. The formulation containing 30% Propylene Glycol which has been used is known to cause hemolysis in humans. Hemolysis, CNS depression, hyperosmolality, and lactic acidosis have been reported after I.V. administration of Propylene glycol [NTP-CERHR Monograph on the Potential Human Reproductive and Developmental Effects of Propylene Glycol (March 2004) NIH Pub. No. 04-4482 Page 11-30] Propylene glycol is viscous with a viscosity of 58.1 cps, thus limiting their use in IM/IV formulation and is not known for the Intravenous administration. (Handbook of Pharmaceutical Excipients, $3^{rd}$ Edition by Dr. Arthur H. Kibbe, Page No. 443)

Cyclodextrins and its advanced derivatives are used in the formulation for solubilizing by the process of complexation of lipophilic compounds. Because of its toxicity, their use is limited. When administered, it is un-metabolized and accumulates in kidney as the insoluble cholesterol complexes resulting in severe nephrotoxicity and hence it has been used primarily for oral purpose. Questions always arise on safety when Cyclodextrin derivatives are administered parenterally (Handbook of Pharmaceutical Excipients, $3^{rd}$ Edition by Dr. Arthur H. Kibbe, Page No. 165). Also the molecular weight of β-cyclodextrin is more than 1000 and hence after administration it could lead to problems of excretion with or without causing damages to kidney or any functions of the organ in the body.

Glycofurol is cyclic glycol derivative used nowadays as solubilizer solvent in parenteral products for intravenous or intramuscular injection in concentration up to 50% v/v. It has viscosity of 8-18 Cps which may also attribute to cloudiness when miscible in water. It is irritant when used undiluted; its tolerability is approximately the same as propylene glycol. Glycofurol has found to have effect on liver function. (Handbook of Pharmaceutical Excipients, Raymond C. Rowe, 5th Edition Page. No. 313). Central nervous system toxicity was also observed when given by intravenous (I.V.) injection. Necrosis of tissue was even observed when it was given intramuscularly (I.M.)

Chremophor El® (Trademark for a polyoxy-ethylene castor oil derivative), a surfactant was also used to solubilize poorly soluble drugs, which was found to have acute anaphylactoid reaction after initiation of intravenous fusion. It was a result due to improper mixing of this vehicle in parenterals and hence different mixing techniques were used to assess their effect on the distribution of Chremophor EL in the solution. This led to problem in parenteral formulation of various actives with this solubilizer and time is required for developing a proper technique for mixing of this solubilizer which limits its use in parenterals with non-safe toxic profile. Due to safety issues, it is used carefully as exceptional use and last resort as drug solubilizing agent (eg. Pacltaxel injection, where balance of convenience suggests its use for terminal therapy of cancer verses anaphylaxis).

Ethyl oleate/Oleic acid ethyl ester is used nowadays for lipophilic compounds and for steroids as vehicle in certain parenteral preparations intended for intramuscular and subcutaneous administration. It is an oily liquid with viscosity of 3.9 Cps at 25° C., less viscous than fixed oils. It is found that it remains clear at 5° C., but darkens in color on standing, so antioxidants are to be added frequently to extend shelf life. Thus addition of group of antioxidants as well as use of amber bottle is required to protect it from light. This increases the cost of formulation by taking control on above factor of packing, stability (Handbook of Pharmaceutical Excipients, Raymond C. Rowe, 5th Edition Page. No. 274).

U.S. Pat. No. 4,628,053 relates to stabilized injection solutions of Piroxicam in which propylene glycol, ethanol and water as the solvent for parenteral administration, which might be viscous and painful at the site of injection.

U.S. Pat. No. 4,824,841 relates to a process for the transformation of Piroxicam into an hydrated form suitable for Oral, topic or parenteral administration.

U.S. Pat. No. 4,942,167 discloses aqueous pharmaceutical formulation containing lyophilized Piroxicam in Glycine as vehicle which is not transparent solution and stability can be issue.

U.S. Pat. No. 5,420,124A relates to an injectable Piroxicam potassium composition which contains triethyleneglycol as a solvent and stabilizer.

WO/1996/041646 disclose a pharmaceutical composition in the form of an aqueous solution or in the form of a product for reconstitution as an aqueous solution, for parenteral administration or ophthalmic administration, comprising Lornoxicam or a pharmaceutically acceptable salt thereof and a cyclodextrin selected from the group consisting of hydroxypropylated or sulphoalkylated derivatives of alpha, beta or gamma cyclodextrin.

Chinese Patent No. CN 101327193 relates to Lornoxicam freeze-dried powder injection and a preparation method thereof. The freeze-dried powder injection comprises Lornoxicam, mannite, tromethamine, EDTA and pH regulator.

From all the above limitations, it is apparent that there is need for a solvent, which is safe and non-toxic, which can be employed as a vehicle for preparation of pharmaceutical compositions in an efficient way through an economical process and being beneficial in treating mammals.

The present inventors have surprisingly found that most, if not all of the limitations/problems/concerns associated with the conventional formulations of various pharmaceutical actives, especially lipophilic actives can be overcome by employing Diethylene glycol monoethyl ether or other alkyl derivatives thereof as a primary vehicle or as a solvent in formulation of pharmaceutical compositions containing such pharmaceutical actives. Diethylene glycol monoethyl ether or other alkyl derivatives thereof are versatile enough to be accepted as vehicles for use in various drug delivery systems. It has been tested for its safety and toxicity and is reported to be safe for its therapeutic use through various routes of administration. Presently the ethyl derivative is in vogue, but use of methyl or any other alkyl derivatives may also be used.

The structure of Diethylene glycol monoethylether is as given below:

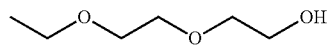

It is less viscous and safe. It has inherent viscosity of about 3.11 cps. It is soluble in water. The density of Diethylene glycol monoethyl ether is 0.985 to 0.991. Diethylene glycol monoethyl ether is less dense than water thereby making it easily flowable. As the compound has less viscosity it can be used for preparations of compositions which are having an easy syringability and thus advantageous to withdraw from vials or ampoules by the healthworkers. Further the same advantage offers doctors with its less painful impact and also less volume of liquid could be administered for the drug products in the therapeutic concentration through parenteral routes.

U.S. Pat. No. 5,837,714 discloses solid pharmaceutical dispersions comprising a poorly soluble drug substance, as SR48692 or Naproxen, Xylitol and Diethylene glycol monoethyl ether, and a method of preparing such dispersions comprising the steps of dissolving the poorly soluble drug substance in Diethylene glycol monoethyl ether and adding the solution to Xylitol. The dispersions exhibit good pharmaceutical properties and reduced levels of impurities and degradation products.

U.S. Patent Application No. 20100056982A1 teaches the photodynamic treatment of acne vulgaris. The method involves the topical administration of a photosensitizer composition comprising hydrophobic green porphyrins such as Lemuteporfin, Polyethylene glycol and skin penetration enhancers such as Oleyl alcohol and Transcutol™ to acne-affected skin and subsequent exposure of that skin to energy of a wavelength of activating the photosensitizer.

U.S. Patent Application No. 20100010059A1 teaches partially based on a discovery that an oral formulation containing N-(3-methylisothiazol-5-yl)-2-[1-(3-methyl-isoxazol-5-ylmethyl)-1H-indol-3-yl]-2-oxoacetamide unexpectedly enhances the oral bioavailability of the compound. In one aspect, this invention features an anticancer formulation, which contains d-alpha-Tocopheryl Polyethylene glycol 1000 succinate ("TPGS"), 2-(2-ethoxyethoxy) ethanol ("Transcutol"); and an effective amount of a compound of formula WO 97/03698 teaches for Transdermal therapeutic system (TTS) having a backing film, having an acrylate-based pressure sensitive adhesive having a hormone content and a content of absorption accelerators and having a protective film, wherein the hormone content is provided by a content of an oestrogen and/or gestagen and/or androgen, and wherein the absorption accelerators are the two substances Oleic acid and 2-(2-ethoxyethoxy)-ethanol.

U.S. Pat. No. 5,552,153 teaches a pharmaceutical composition for transdermal delivery comprising an effective amount of an active ingredient selected from a Benzodiazepine and a Benzodiazepine antagonist; Ethanol; Caprylic acid; and Oleic acid. Additionally, the composition may contain Silicon fluid, Benzyl alcohol, and Diethylene glycol monoethyl ether or Dimethyl sulfoxide.

U.S. Pat. No. 5,998,392 teaches about the improved compositions of Benzoyl peroxide and methods of processing Benzoyl peroxide. More particularly, the invention relates to the use of a composition such as Transcutol®. Diethylene glycol monoethyl ether as a processing aid for making a new benzoyl peroxide premixture which can be admixed with an aqueous medium to make a new benzoyl peroxide flocculent composition.

U.S. Pat. No. 5,741,512 teaches with the Pharmaceutical compositions comprising Cyclosporin, e.g. Cyclosporin as "microemulsion pre-concentrate" and microemulsion form. The compositions typically comprise a C.sub.1-5 alkyl or tetrahydrofurfuryl di- or partial-ether of a low molecular weight mono- or poly-oxy-alkane diol, e.g. Transcutol or Glycofurol, as hydrophilic component. Compositions are also provided comprising a cyclosporin and, suitably, also a saccharide monoester, e.g. raffinose or saccharose monolaurate. Dosage forms include topical formulations and, in particular, oral dosage forms.

OBJECTS OF THE INVENTION

An object of the present invention is to provide pharmaceutical compositions of various pharmaceutical actives containing Diethylene glycol monoethyl ether or other alkyl derivatives thereof as a primary vehicle or solvent.

Another object of the present invention is to provide pharmaceutical compositions of various lipophilic and hydrophilic actives containing Diethylene glycol monoethyl ether or other alkyl derivatives thereof as a primary vehicle or solvent.

Yet another object of the present invention is to provide use of Diethylene glycol monoethyl ether or other alkyl derivatives thereof as a primary vehicle or as a solvent in preparation of pharmaceutical compositions containing various pharmaceutical actives.

Still another object of the present invention is to provide use of Diethylene glycol monoethyl ether or other alkyl derivatives thereof as a primary vehicle or as a solvent in preparation of pharmaceutical compositions containing various lipophilic and hydrophilic actives.

Another object of the present invention is to utilize Diethylene glycol monoethyl ether or other alkyl derivatives thereof as a primary vehicle or solvent for formulation of pharmaceutical actives which are difficult to solubilize in physiologically acceptable solvents.

Yet another object of the present invention is to utilize Diethylene glycol monoethyl ether or other alkyl derivatives thereof as a primary vehicle or solvent for formulation of lipophilic and hydrophilic actives which are difficult to solubilize in physiologically acceptable solvents.

Still another object of the present invention is to utilize Diethylene glycol monoethyl ether or other alkyl derivatives thereof as a primary vehicle or solvent for formulation of pharmaceutical actives which exhibit instability when compounded with an aqueous phase.

Another object of the present invention is to utilize Diethylene glycol monoethyl ether or other alkyl derivatives thereof as a primary vehicle or solvent for formulation of lipophilic and hydrophilic actives which exhibit instability when compounded with an aqueous phase.

Yet another object of the present invention is to utilize Diethylene glycol monoethyl ether or other alkyl derivatives thereof as a primary vehicle or solvent for formulation of pharmaceutical actives which are difficult to solubilize in physiologically acceptable solvents and require to be formulated as oily injections.

Still another object of the present invention is to utilize Diethylene glycol monoethyl ether or other alkyl derivatives thereof as a primary vehicle or solvent for formulation of lipophilic and hydrophilic actives which are difficult to solubilize in physiologically acceptable solvents and require to be formulated as oily injections.

Another object of the present invention is to utilize Diethylene glycol monoethyl ether or other alkyl derivatives thereof as a primary vehicle or solvent for formulation of pharmaceutical actives which are difficult to solubilize in physiologically acceptable solvents and require to be formulated as emulsions.

Yet another object of the present invention is to utilize Diethylene glycol monoethyl ether or other alkyl derivatives thereof as a primary vehicle or solvent for formulation of lipophilic and hydrophilic actives which are difficult to solubilize in physiologically acceptable solvents and require to be formulated as emulsions.

Still another object of the present invention is to utilize Diethylene glycol monoethyl ether or other alkyl derivatives thereof as a primary vehicle or solvent for formulation of pharmaceutical actives which are free from oil and related matters.

Another object of the present invention is to utilize Diethylene glycol monoethyl ether or other alkyl derivatives thereof as a primary vehicle or solvent for formulation of lipophilic and hydrophilic actives which are free from oil and related matters.

Yet another object of the present invention is to utilize Diethylene glycol monoethyl ether or other alkyl derivatives thereof as a primary vehicle or solvent for formulation of pharmaceutical actives which are less viscous, less dense and more transparent than oily injections containing such pharmaceutical actives.

Still another object of the present invention is to utilize Diethylene glycol monoethyl ether or other alkyl derivatives thereof as a primary vehicle or solvent for formulation of lipophilic and hydrophilic actives which are less viscous, less dense and more transparent than oily injections containing such lipophilic actives.

Another object of the present invention is to utilize Diethylene glycol monoethyl ether or other alkyl derivatives thereof as a primary vehicle or solvent for formulation of pharmaceutical actives which results in less pain when injected compared to that caused by administration of oily injections containing such pharmaceutical actives.

Yet another object of the present invention is to utilize Diethylene glycol monoethyl ether or other alkyl derivatives thereof as a primary vehicle or solvent for formulation of lipophilic and hydrophilic actives which results in less pain when injected compared to that caused by administration of oily injections containing such lipophilic actives.

Still another object of the present invention is to utilize Diethylene glycol monoethyl ether or other alkyl derivatives thereof as a primary vehicle or solvent for formulation of pharmaceutical actives which can be easily administered by doctors/physicians/nurses.

Another object of the present invention is to utilize Diethylene glycol monoethyl ether or other alkyl derivatives thereof as a primary vehicle or solvent for formulation of lipophilic and hydrophilic actives which can be easily administered by doctors/physicians/nurses.

Yet another object of the present invention is to provide pharmaceutical compositions of pharmaceutical actives containing or utilizing Diethylene glycol monoethyl ether or other alkyl derivatives thereof as a primary vehicle or solvent, which are easy to manufacture, do not involve any lengthy and tedious manufacturing steps, which are viable and economical.

Still another object of the present invention is to provide pharmaceutical compositions of lipophilic and hydrophilic actives containing or utilizing Diethylene glycol monoethyl ether or other alkyl derivatives thereof as a primary vehicle or solvent, which are easy to manufacture, do not involve any lengthy and tedious manufacturing steps, which are viable and economical.

Another object of the present invention is to provide pharmaceutical compositions of pharmaceutical actives containing or utilizing Diethylene glycol monoethyl ether or other alkyl derivatives thereof as a primary vehicle or solvent, which do not cause side effects; which do not cause pain, erythema, swelling at the site of injection; which do not cause damage to nerves, arteries or veins; and which does not require a test dose to be given to the patient prior to actual administration.

Yet another object of the present invention is to provide pharmaceutical compositions of lipophilic and hydrophilic actives containing or utilizing Diethylene glycol monoethyl ether or other alkyl derivatives thereof as a primary vehicle or solvent, which do not cause side effects; which do not cause pain, erythema, swelling at the site of injection; which do not cause damage to nerves, arteries or veins; and which does not require a test dose to be given to the patient prior to actual administration.

Still another object of the present invention is to provide pharmaceutical compositions of pharmaceutical actives containing or utilizing Diethylene glycol monoethyl ether or other alkyl derivatives thereof as a primary vehicle or solvent, which do not cause logistical difficulties when administered to a patient who is in employment; which does not have staffing and medicine storage issues; and which is not stigmatizing or coercive to a patient.

Another object of the present invention is to provide pharmaceutical compositions of lipophilic and hydrophilic actives containing or utilizing Diethylene glycol monoethyl ether or other alkyl derivatives thereof as a primary vehicle or solvent, which do not cause logistical difficulties when administered to a patient who is in employment; which does not have staffing and medicine storage issues; and which is not stigmatizing or coercive to a patient.

Yet another object of the present invention is to provide pharmaceutical compositions of pharmaceutical actives containing or utilizing Diethylene glycol monoethyl ether or other alkyl derivatives thereof as a primary vehicle or solvent, which do not contain stabilizers or preservatives in large amounts for maintaining the stability of the compositions.

Still another object of the present invention is to provide pharmaceutical compositions of lipophilic and hydrophilic actives containing or utilizing Diethylene glycol monoethyl ether or other alkyl derivatives thereof as a primary vehicle or solvent, which do not contain stabilizers or preservatives in large amounts for maintaining the stability of the compositions.

Another object of the present invention is to provide pharmaceutical compositions of pharmaceutical actives containing or utilizing Diethylene glycol monoethyl ether or other alkyl derivatives thereof as a primary vehicle or solvent, which do not cause skin and tissue trauma; muscle fibrosis and contracture; nerve palsies; paralysis; anaphylactic shock; formation of thrombosis in veins; thrombo phlebitis; and abscesses or gangrene, when administered intramuscularly.

Yet another object of the present invention is to provide pharmaceutical compositions of lipophilic and hydrophilic actives containing or utilizing Diethylene glycol monoethyl ether or other alkyl derivatives thereof as a primary vehicle or solvent, which do not cause skin and tissue trauma; muscle fibrosis and contracture; nerve palsies; paralysis; anaphylactic shock; formation of thrombosis in veins; thrombo phlebitis; and abscesses or gangrene, when administered intramuscularly.

Still another object of the present invention is to provide pharmaceutical compositions of pharmaceutical actives containing or utilizing Diethylene glycol monoethyl ether or other alkyl derivatives thereof as a primary vehicle or solvent, which does not require special facilities to maintain asceptic conditions for manufacturing such as crystallization, particle size reduction, wetting, sterilization etc.

Another object of the present invention is to provide pharmaceutical compositions of lipophilic and hydrophilic actives containing or utilizing Diethylene glycol monoethyl ether or other alkyl derivatives thereof as a primary vehicle or solvent, which does not require special facilities to maintain asceptic conditions for manufacturing such as crystallization, particle size reduction, wetting, sterilization etc.

Yet another object of the present invention is to provide pharmaceutical compositions of pharmaceutical actives containing or utilizing Diethylene glycol monoethyl ether or other alkyl derivatives thereof as a primary vehicle or solvent, wherein the stability of the compositions during the period between manufacture and use does not result in settlement of solids, caking, difficulty in redispersion etc.

Still another object of the present invention is to provide pharmaceutical compositions of lipophilic and hydrophilic actives containing or utilizing Diethylene glycol monoethyl ether or other alkyl derivatives thereof as a primary vehicle or solvent, wherein the stability of the compositions during the period between manufacture and use does not result in settlement of solids, caking, difficulty in redispersion etc.

Another object of the present invention is to provide pharmaceutical compositions of pharmaceutical actives containing or utilizing Diethylene glycol monoethyl ether or other alkyl derivatives thereof as a primary vehicle or solvent, wherein there is uniformity of dose at the time of administration and vials need not be shaken for uniformity prior to use.

Yet another object of the present invention is to provide pharmaceutical compositions of lipophilic and hydrophilic actives containing or utilizing Diethylene glycol monoethyl ether or other alkyl derivatives thereof as a primary vehicle or solvent, wherein there is uniformity of dose at the time of administration and vials need not be shaken for uniformity prior to use.

Still another object of the present invention is to provide pharmaceutical compositions of pharmaceutical actives containing or utilizing Diethylene glycol monoethyl ether or other alkyl derivatives thereof as a primary vehicle or solvent, which need not be applied as soon as possible to avoid settling in the syringe and do not cause an issue for the doctor/physician/nurse.

Another object of the present invention is to provide pharmaceutical compositions of lipophilic and hydrophilic actives containing or utilizing Diethylene glycol monoethyl ether or other alkyl derivatives thereof as a primary vehicle or solvent, which need not be applied as soon as possible to avoid settling in the syringe and do not cause an issue for the doctor/physician/nurse.

Yet another object of the present invention is to provide pharmaceutical compositions of pharmaceutical actives containing or utilizing Diethylene glycol monoethyl ether or other alkyl derivatives thereof as a primary vehicle or solvent, which exhibit enhanced physical stability in comparison to conventional compositions containing such pharmaceutical actives.

Still another object of the present invention is to provide pharmaceutical compositions of lipophilic and hydrophilic actives containing or utilizing Diethylene glycol monoethyl ether or other alkyl derivatives thereof as a primary vehicle or solvent, which exhibit enhanced physical stability in comparison to conventional compositions containing such lipophilic and hydrophilic actives.

Another object of the present invention is to provide pharmaceutical compositions of pharmaceutical actives containing or utilizing Diethylene glycol monoethyl ether or other alkyl derivatives thereof as a primary vehicle or solvent, which are versatile enough to be accepted as vehicles for use in various drug delivery systems.

Yet another object of the present invention is to provide pharmaceutical compositions of lipophilic and hydrophilic actives containing or utilizing Diethylene glycol monoethyl ether or other alkyl derivatives thereof as a primary vehicle or solvent, which are versatile enough to be accepted as vehicles for use in various drug delivery systems.

Still another object of the present invention is to provide pharmaceutical compositions of pharmaceutical actives containing or utilizing Diethylene glycol monoethyl ether or other alkyl derivatives thereof as a primary vehicle or solvent, which are safe and non-toxic for various routes of administration.

Another object of the present invention is to provide pharmaceutical compositions of lipophilic and hydrophilic actives containing or utilizing Diethylene glycol monoethyl ether or other alkyl derivatives thereof as a primary vehicle or solvent, which are safe and non-toxic for various routes of administration.

Yet another object of the present invention is to provide pharmaceutical compositions of pharmaceutical actives containing or utilizing Diethylene glycol monoethyl ether or other alkyl derivatives thereof as a primary vehicle or solvent, for use in parenteral, oral, dermal, nasal, and other dosage forms.

Still another object of the present invention is to provide pharmaceutical compositions of lipophilic and hydrophilic actives containing or utilizing Diethylene glycol monoethyl ether or other alkyl derivatives thereof as a primary vehicle or solvent, for use in parenteral, oral, dermal, nasal, and other dosage forms.

Another object of the present invention is to provide; pharmaceutical compositions of pharmaceutical actives containing or utilizing Diethylene glycol monoethyl ether or other alkyl derivatives thereof as a primary vehicle or solvent, for use of administration via I.M and/or I.V route, oral, dermal, nasal, optic, and other routes of administration.

Yet another object of the present invention is to provide pharmaceutical compositions of lipophilic and hydrophilic actives containing or utilizing Diethylene glycol monoethyl ether or other alkyl derivatives thereof as a primary vehicle or solvent, for use of administration via I.M and/or I.V route, oral, dermal, nasal, optic, and other routes of administration.

Still another object of the present invention is to provide pharmaceutical compositions of pharmaceutical actives containing or utilizing Diethylene glycol monoethyl ether or other alkyl derivatives thereof as a primary vehicle or solvent, which also provides the function of a permeation enhancing agent.

Another object of the present invention is to provide pharmaceutical compositions of lipophilic and hydrophilic actives containing or utilizing Diethylene glycol monoethyl ether or other alkyl derivatives thereof as a primary vehicle or solvent, which also provides the function of a permeation enhancing agent.

Yet another object of the present invention is to provide pharmaceutical compositions of pharmaceutical actives containing or utilizing Diethylene glycol monoethyl ether or other alkyl derivatives thereof as a primary vehicle or solvent, which provides ease of application of the said pharmaceutical actives comparatively reduced pain at the site of injection via I.M and I.V route.

Still another object of the present invention is to provide pharmaceutical compositions of lipophilic and hydrophilic actives containing or utilizing Diethylene glycol monoethyl ether or other alkyl derivatives thereof as a primary vehicle or solvent, which provides ease of application of the said lipophilic and hydrophilic actives comparatively reduced pain at the site of injection via I.M and I.V route.

Another object of the present invention is to provide pharmaceutical compositions of pharmaceutical actives containing or utilizing Diethylene glycol monoethyl ether or other alkyl derivatives thereof as a primary vehicle or solvent, which exist in different dosage forms with desired quality control and are especially free from toxicity problems encountered due to solvents.

Yet another object of the present invention is to provide pharmaceutical compositions of lipophilic and hydrophilic actives containing or utilizing Diethylene glycol monoethyl ether or other alkyl derivatives thereof as a primary vehicle or solvent, which exist in different dosage forms with desired quality control and are especially free from toxicity problems in the therapeutic dose of drugs and encountered due to solvents.

Still another object of the present invention is to provide pharmaceutical compositions of pharmaceutical actives containing or utilizing Diethylene glycol monoethyl ether or other alkyl derivatives thereof as a primary vehicle or solvent, which can be formulated into different dosage forms such as capsules, nasal sprays, gargles, dermal gels, and others, which, moreover, can be made into a soluble pellucid solution.

Another object of the present invention is to provide pharmaceutical compositions of lipophilic and hydrophilic actives containing or utilizing Diethylene glycol monoethyl ether or other alkyl derivatives thereof as a primary vehicle or solvent, which can be formulated into different dosage forms such as capsules, nasal sprays, gargles, dermal gels, and others, which, moreover, can be made into a soluble pellucid solution.

Yet another object of the present invention is to provide pharmaceutical compositions of pharmaceutical actives containing or utilizing Diethylene glycol monoethyl ether or other alkyl derivatives thereof as a primary vehicle or solvent, which are comparatively less toxic and at the same time would be excreted out easily without causing damage to any organ, especially kidney, as well as would not get accumulated in any part of the body.

Still another object of the present invention is to provide pharmaceutical compositions of lipophilic and hydrophilic actives containing or utilizing Diethylene glycol monoethyl ether or other alkyl derivatives thereof as a primary vehicle or solvent, which are non-toxic and at the same time would be excreted out easily without causing damage to any organ, especially kidney, as well as would not get accumulated in any part of the body.

Another object of the present invention is to provide pharmaceutical compositions of pharmaceutical actives containing or utilizing Diethylene glycol monoethyl ether or other alkyl derivatives thereof as a primary vehicle or solvent, which provides transparent and less viscous parenteral solutions.

Yet another object of the present invention is to provide pharmaceutical compositions of lipophilic and hydrophilic actives containing or utilizing Diethylene glycol monoethyl ether or other alkyl derivatives thereof as a primary vehicle or solvent, which provides transparent and less viscous parenteral solutions.

Still another object of the present invention is to provide pharmaceutical compositions of pharmaceutical actives containing or utilizing Diethylene glycol monoethyl ether or other alkyl derivatives thereof as a primary vehicle or solvent, which exhibit better bioavailability in comparison to conventional compositions containing such pharmaceutical actives.

Another object of the present invention is to provide pharmaceutical compositions of lipophilic and hydrophilic actives containing or utilizing Diethylene glycol monoethyl ether or other alkyl derivatives thereof as a primary vehicle or solvent, which exhibit better bioavailability in comparison to conventional compositions containing such lipophilic and hydrophilic actives.

Yet another object of the present invention is to provide pharmaceutical compositions of pharmaceutical actives containing or utilizing Diethylene glycol monoethyl ether or other alkyl derivatives thereof as a primary vehicle or solvent, wherein the said pharmaceutical actives are not milled or micronized.

Still another object of the present invention is to provide pharmaceutical compositions of lipophilic and hydrophilic actives containing or utilizing Diethylene glycol monoethyl ether or other alkyl derivatives thereof as a primary vehicle or solvent, wherein the said lipophilic and hydrophilic actives are not milled or micronized.

A further object of the present invention is to provide pharmaceutical compositions of pharmaceutical actives containing or utilizing Diethylene glycol monoethyl ether or other alkyl derivatives thereof as a primary vehicle or solvent, which preferably contains preservatives and buffers to maintain its pH.

Yet further object of the present invention is to provide pharmaceutical compositions of lipophilic and hydrophilic actives containing or utilizing Diethylene glycol monoethyl ether or other alkyl derivatives thereof as a primary vehicle or solvent, which preferably contains preservatives and buffers to maintain its pH.

BRIEF DESCRIPTION OF THE FIGURE

FIG. 1 shows the operator simply wears a special force sensor on thumb and measures the force which elicit the animal response.

SUMMARY OF THE INVENTION

In accordance with the need for a vehicle or solvent, which is safe and non-toxic for formulation and preparation of pharmaceutical compositions, containing pharmaceutical actives, especially lipophilic and hydrophilic actives belonging to diverse pharmacological and therapeutic classes and which, moreover, can be manufactured in an efficient way through an economical process and being beneficial in treating mammals and, which, further, is free from most, if not all of the limitations/problems/concerns associated with the conventional formulations of such pharmaceutical actives the present inventors have found that Diethylene glycol monoethyl ether or other alkyl derivatives thereof, especially the former, is the vehicle or solvent of choice.

The present inventors have found Diethylene glycol monoethyl ether, otherwise known as 2-(2-Ethoxyethoxy) ethanol, CARBITOL™, DE Solvent, Diethylene glycol ethyl ether, Ethyldiglycol or Transcutol and having the structure shown below,

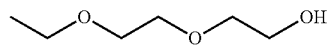

is versatile enough to be accepted as a vehicle for use in various drug delivery systems. It has been tested for its safety and toxicity and is reported to be safe for its therapeutic use through various routes of administration. Presently the ethyl derivative is in vogue, but use of methyl or any other alkyl derivatives after its safety evaluation may be used.

The use of Diethylene glycol monoethyl ether or other alkyl derivatives thereof in formulation or manufacture of pharmaceutical compositions of pharmaceutical actives, especially lipophilic actives belonging to diverse pharmacological and therapeutic categories results in many advantages, such as:

(a) It has great solubilizing power and can easily solubilize various pharmaceutical actives, belonging to diverse pharmacological and therapeutic classes as listed in Categories (I) to (XXII) described in the BACKGROUND OF THE INVENTION section of this Application, which other solvents/vehicles known in the art are not completely capable of;

(b) It is versatile enough to be accepted as a vehicle or solvent for use in various drug delivery systems for use in parenteral (both intramuscular and intravenous), oral, dermal, nasal, optic, ocular and otic other routes of administration, especially as injectables, capsules, nasal sprays, gargles, dermal gels etc.;

(c) It is a highly versatile vehicle or solvent for formulation of pharmaceutical actives, especially lipophilic actives, which are difficult to solubilize and require to be formulated as oily injections or as emulsions, or which exhibit instability when compounded with an aqueous phase;

(d) It is safe for various routes of administration and is less toxic from toxicity and quality control problems encountered with other solvents known in the art;

(e) The pharmaceutical compositions of various pharmaceutical actives containing it as a vehicle or solvent exhibit enhanced physical stability in comparison to convention compositions of such pharmaceutical actives;

(f) Its use as a vehicle or solvent results in formulation of pharmaceutical compositions of pharmaceutical actives, which are easy to manufacture; do not involve and lengthy and tedious manufacturing steps; which are viable and economical; and which do not require special facilities to maintain aseptic conditions for manufacturing such as crystallization, particle size reduction, wetting, sterilization etc.;

(g) Its use as a vehicle or solvent results in formulation of pharmaceutical compositions of pharmaceutical actives, which will have a better bioavailability;

(h) Its use as a vehicle or solvent results in formulation of pharmaceutical compositions of pharmaceutical actives, which are more transparent, less viscous, and less dense than oily injections containing such pharmaceutical actives and can be made into a soluble pellucid solution;

(i) The pharmaceutical compositions of various pharmaceutical actives containing it as a vehicle or solvent are free from oil and objectionable/problematic matters and hence more stable;

(j) The pharmaceutical compositions of various pharmaceutical actives containing it as a vehicle or solvent cause less pain when injected compared to that caused by injection of oily injections containing such pharmaceutical actives;

(k) The pharmaceutical compositions of various pharmaceutical actives containing it as a vehicle or solvent are easy to administer and thereby useful for doctors/physicians/nurses;

(l) The pharmaceutical compositions of various pharmaceutical actives containing it as a vehicle or solvent are free of side effects associated with conventional formulations and most importantly do not require a test dose to be given to the patient prior to actual administration;

(m) The pharmaceutical compositions of various pharmaceutical actives containing it as a vehicle or solvent do not cause pain, erythema, swelling at the site of injections; do not cause damage to nerves, arteries or veins; do not cause skin and tissue trauma; muscle fibrosis and contracture; nerve palsies; paralysis; anaphylactic shock; formation of thrombosis in veins; thrombo phlebitis; abscesses or gangrene; do not have staffing and medicine storage issues; is not stigmatizing or coercive to a patient; and do not cause logistical difficulties when administered to a patient who is in employment;

(n) The pharmaceutical compositions of various pharmaceutical actives containing it as a vehicle or solvent which do not exhibit instability during the period between manufacture and use; do not result in settlement of solids, caking, difficulty in redispersion etc.; do not result in non-uniformity of dose at the time of administration and vials need not be shaken for uniformity prior to use;

(o) It also functions as a permeation enhancing agent;

(p) The pharmaceutical compositions of various pharmaceutical actives containing it as a vehicle or solvent do not require stabilizers or preservatives in large amounts for maintaining the stability of the compositions; and (q) It is excreted easily without causing damage to any organ, especially kidney, as well as would not get accumulated in any part of the body; and (r) Its use obviates the need for the pharmaceutical actives or lipophilic actives to be milled or micronized prior to use.

Typically, the pharmaceutical or lipophilic actives, embraced within the scope of the present invention, which however, should be construed as non-limiting can be classified in to the following three categories, viz.

1) Those which are difficult to solubilize and often require toxic vehicles for solubilization and may further require unwanted excipients for formulation into suitable dosage forms;
2) Those which have stability issues and often require complex and expensive technology for formulation of such actives into suitable stable dosage forms; and
3) Those which are available in the form of suspensions and are very difficult to be solubilized into a solution form.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injections for rapid onset of action when required to provide earliest result into the patient as well as can be used for formulation of different dosage forms like capsules, nasal sprays, gargles, gels, topical, ocular, otic, oral dosage forms etc. The solution may additionally contain preservatives and buffers for maintenance of pH. The solutions exhibit enhanced stability compared and are less toxic.

In accordance with the above:

In one embodiment the present invention provides pharmaceutical compositions of various pharmaceutical actives containing Diethylene glycol monoethyl ether or other alkyl derivatives thereof as a primary vehicle or solvent.

In another embodiment the present invention provides pharmaceutical compositions of various lipophilic and hydrophilic actives containing Diethylene glycol monoethyl ether or other alkyl derivatives thereof as a primary vehicle or solvent.

In yet another embodiment the present invention relates to use of Diethylene glycol monoethyl ether or other alkyl derivatives thereof as a primary vehicle or as a solvent in preparation of pharmaceutical compositions containing various pharmaceutical actives.

In still another embodiment the present invention relates to use of Diethylene glycol monoethyl ether or other alkyl derivatives thereof as a primary vehicle or as a solvent in preparation of pharmaceutical compositions containing various lipophilic and hydrophilic actives.

In another embodiment the present invention relates to utilization of Diethylene glycol monoethyl ether or other alkyl derivatives thereof as a primary vehicle or solvent for formulation of pharmaceutical actives which are difficult to solubilize in physiologically acceptable solvents.

In yet another embodiment the present invention relates to utilization of Diethylene glycol monoethyl ether or other alkyl derivatives thereof as a primary vehicle or solvent for formulation of lipophilic and hydrophilic actives which are difficult to solubilize in physiologically acceptable solvents.

In still another embodiment the present invention relates to utilization of Diethylene glycol monoethyl ether or other alkyl derivatives thereof as a primary vehicle or solvent for formulation of pharmaceutical actives which exhibit instability when compounded with an aqueous phase.

In another embodiment the present invention relates to utilization of Diethylene glycol monoethyl ether or other alkyl derivatives thereof as a primary vehicle or solvent for formulation of lipophilic and hydrophilic actives which exhibit instability when compounded with an aqueous phase.

In yet another embodiment the present invention relates to utilization of Diethylene glycol monoethyl ether or other alkyl derivatives thereof as a primary vehicle or solvent for formulation of pharmaceutical actives which are difficult to solubilize in physiologically acceptable solvents and require to be formulated as oily injections.

In still another embodiment the present invention relates to utilization of Diethylene glycol monoethyl ether or other alkyl derivatives thereof as a primary vehicle or solvent for formulation of lipophilic and hydrophilic actives which are difficult to solubilize in physiologically acceptable solvents and require to be formulated as oily injections.

In another embodiment the present invention relates to utilization of Diethylene glycol monoethyl ether or other alkyl derivatives thereof as a primary vehicle or solvent for formulation of pharmaceutical actives which are difficult to solubilize in physiologically acceptable solvents and require to be formulated as emulsions.

In still another embodiment the present invention Diethylene glycol monoethyl ether or other alkyl derivatives thereof is employed in an amount of 1% to 100% by weight of the pharmaceutical composition.

In yet another embodiment the present invention relates to utilization of Diethylene glycol monoethyl ether or other alkyl derivatives thereof as a primary vehicle or solvent for formulation of lipophilic and hydrophilic actives which are difficult to solubilize in physiologically acceptable solvents and require to be formulated as emulsions.

In still another embodiment the present invention relates to utilization of Diethylene glycol monoethyl ether or other alkyl derivatives thereof as a primary vehicle or solvent for formulation of pharmaceutical actives which are free from oil and related matters.

In another embodiment the present invention relates to utilization of Diethylene glycol monoethyl ether or other alkyl derivatives thereof as a primary vehicle or solvent for formulation of lipophilic and hydrophilic actives which are free from oil and related matters.

In yet another embodiment the present invention relates to utilization of Diethylene glycol monoethyl ether or other alkyl derivatives thereof as a primary vehicle or solvent for formulation of pharmaceutical actives which are less viscous, less dense and more transparent than oily injections containing such pharmaceutical actives.

In still another embodiment the present invention relates to utilization of Diethylene glycol monoethyl ether or other alkyl derivatives thereof as a primary vehicle or solvent for formulation of lipophilic and hydrophilic actives which are less viscous, less dense and more transparent than oily injections containing such lipophilic and hydrophilic actives.

In another embodiment the present invention relates to utilization of Diethylene glycol monoethyl ether or other alkyl derivatives thereof as a primary vehicle or solvent for formulation of pharmaceutical actives which results in less pain when injected compared to that caused by administration of oily injections containing such pharmaceutical actives.

In yet another embodiment the present invention relates to utilization of Diethylene glycol monoethyl ether or other alkyl derivatives thereof as a primary vehicle or solvent for formulation of lipophilic and hydrophilic actives which results in less pain when injected compared to that caused by administration of oily injections containing such lipophilic and hydrophilic actives.

In still another embodiment the present invention relates to utilization of Diethylene glycol monoethyl ether or other alkyl derivatives thereof as a primary vehicle or solvent for formulation of pharmaceutical actives which can be easily administered by doctors/physicians/nurses.

In another embodiment the present invention relates to utilization of Diethylene glycol monoethyl ether or other alkyl derivatives thereof as a primary vehicle or solvent for formulation of lipophilic and hydrophilic actives which can be easily administered by doctors/physicians/nurses.

In yet another embodiment the present invention provides pharmaceutical compositions of pharmaceutical actives containing or utilizing Diethylene glycol monoethyl ether or other alkyl derivatives thereof as a primary vehicle or solvent, which are easy to manufacture, do not involve any lengthy and tedious manufacturing steps, which are viable and economical.

In still another embodiment the present invention provides pharmaceutical compositions of lipophilic and hydrophilic actives containing or utilizing Diethylene glycol monoethyl ether or other alkyl derivatives thereof as a primary vehicle or solvent, which are easy to manufacture, do not involve any lengthy and tedious manufacturing steps, which are viable and economical.

In another embodiment the present invention provides pharmaceutical compositions of pharmaceutical actives containing or utilizing Diethylene glycol monoethyl ether or other alkyl derivatives thereof as a primary vehicle or solvent, which do not cause side effects; which do not cause pain, erythema, swelling at the site of injection; which do not cause damage to nerves, arteries or veins; and which does not require a test dose to be given to the patient prior to actual administration.

In yet another embodiment the present invention provides pharmaceutical compositions of lipophilic and hydrophilic actives containing or utilizing Diethylene glycol monoethyl ether or other alkyl derivatives thereof as a primary vehicle or solvent, which do not cause side effects; which do not cause pain, erythema, swelling at the site of injection; which do not cause damage to nerves, arteries or veins; and which does not require a test dose to be given to the patient prior to actual administration.

In still another embodiment the present invention provides pharmaceutical compositions of pharmaceutical actives containing or utilizing Diethylene glycol monoethyl ether or other alkyl derivatives thereof as a primary vehicle or solvent, which do not cause logistical difficulties when administered to a patient who is in employment; which does not have staffing and medicine storage issues; and which is not stigmatizing or coercive to a patient.

In another embodiment the present invention provides pharmaceutical compositions of lipophilic and hydrophilic actives containing or utilizing Diethylene glycol monoethyl ether or other alkyl derivatives thereof as a primary vehicle or solvent, which do not cause logistical difficulties when administered to a patient who is in employment; which does not have staffing and medicine storage issues; and which is not stigmatizing or coercive to a patient.

In yet another embodiment the present invention provides pharmaceutical compositions of pharmaceutical actives containing or utilizing Diethylene glycol monoethyl ether or other alkyl derivatives thereof as a primary vehicle or solvent, which do not contain stabilizers or preservatives in large amounts for maintaining the stability of the compositions.

In still another embodiment the present invention provides pharmaceutical compositions of lipophilic and hydrophilic actives containing or utilizing Diethylene glycol monoethyl ether or other alkyl derivatives thereof as a primary vehicle or solvent, which do not contain stabilizers or preservatives in large amounts for maintaining the stability of the compositions.

In another embodiment the present invention provides pharmaceutical compositions of pharmaceutical actives containing or utilizing Diethylene glycol monoethyl ether or other alkyl derivatives thereof as a primary vehicle or solvent, which do not cause skin and tissue trauma; muscle fibrosis and contracture; nerve palsies; paralysis; anaphylactic shock; formation of thrombosis in veins; thrombo phlebitis; and abscesses or gangrene, when administered intramuscularly.

In yet another embodiment the present invention provides pharmaceutical compositions of lipophilic and hydrophilic actives containing or utilizing Diethylene glycol monoethyl ether or other alkyl derivatives thereof as a primary vehicle or solvent, which do not cause skin and tissue trauma; muscle fibrosis and contracture; nerve palsies; paralysis; anaphylactic shock; formation of thrombosis in veins; thrombo phlebitis; and abscesses or gangrene, when administered intramuscularly.

In still another embodiment the present invention provides pharmaceutical compositions of pharmaceutical actives containing or utilizing Diethylene glycol monoethyl ether or other alkyl derivatives thereof as a primary vehicle or solvent, which does not require special facilities to maintain asceptic conditions for manufacturing such as crystallization, particle size reduction, wetting, sterilization etc.

In another embodiment the present invention provides pharmaceutical compositions of lipophilic and hydrophilic actives containing or utilizing Diethylene glycol monoethyl ether or other alkyl derivatives thereof as a primary vehicle or solvent, which does not require special facilities to maintain asceptic conditions for manufacturing such as crystallization, particle size reduction, wetting, sterilization etc.

In yet another embodiment the present invention provides pharmaceutical compositions of pharmaceutical actives containing or utilizing Diethylene glycol monoethyl ether or other alkyl derivatives thereof as a primary vehicle or solvent, wherein the stability of the compositions during the period between manufacture and use does not result in settlement of solids, caking, difficulty in redispersion etc.

In still another the present invention provides pharmaceutical compositions of lipophilic and hydrophilic actives containing or utilizing Diethylene glycol monoethyl ether or other alkyl derivatives thereof as a primary vehicle or solvent, wherein the stability of the compositions during the period between manufacture and use does not result in settlement of solids, caking, difficulty in redispersion etc.

In another embodiment the present invention provides pharmaceutical compositions of pharmaceutical actives containing or utilizing Diethylene glycol monoethyl ether or other alkyl derivatives thereof as a primary vehicle or solvent, wherein there is uniformity of dose at the time of administration and vials need not be shaken for uniformity prior to use.

In yet another embodiment the present invention provides pharmaceutical compositions of lipophilic and hydrophilic actives containing or utilizing Diethylene glycol monoethyl ether or other alkyl derivatives thereof as a primary vehicle or solvent, wherein there is uniformity of dose at the time of administration and vials need not be shaken for uniformity prior to use.

In still another embodiment the present invention provides pharmaceutical compositions of pharmaceutical actives containing or utilizing Diethylene glycol monoethyl ether or other alkyl derivatives thereof as a primary vehicle or solvent, which need not be applied as soon as possible to avoid settling in the syringe and do not cause an issue for the doctor/physician/nurse.

In another embodiment the present invention provides pharmaceutical compositions of lipophilic and hydrophilic actives containing or utilizing Diethylene glycol monoethyl ether or other alkyl derivatives thereof as a primary vehicle or solvent, which need not be applied as soon as possible to avoid settling in the syringe and do not cause an issue for the doctor/physician/nurse.

In yet another embodiment the present invention provides pharmaceutical compositions of pharmaceutical actives containing or utilizing Diethylene glycol monoethyl ether or other alkyl derivatives thereof as a primary vehicle or solvent, which exhibit enhanced physical stability in comparison to conventional compositions containing such pharmaceutical actives.

In still another embodiment the present invention provides pharmaceutical compositions of lipophilic and hydrophilic actives containing or utilizing Diethylene glycol monoethyl ether or other alkyl derivatives thereof as a primary vehicle or solvent, which exhibit enhanced physical stability in comparison to conventional compositions containing such lipophilic and hydrophilic actives.

In another embodiment the present invention provides pharmaceutical compositions of pharmaceutical actives containing or utilizing Diethylene glycol monoethyl ether or other alkyl derivatives thereof as a primary vehicle or solvent, which are versatile enough to be accepted as vehicles for use in various drug delivery systems.

In yet another embodiment the present invention provides pharmaceutical compositions of lipophilic and hydrophilic actives containing or utilizing Diethylene glycol monoethyl ether or other alkyl derivatives thereof as a primary vehicle or solvent, which are versatile enough to be accepted as vehicles for use in various drug delivery systems.

In still another embodiment the present invention provides pharmaceutical compositions of pharmaceutical actives containing or utilizing Diethylene glycol monoethyl ether or other alkyl derivatives thereof as a primary vehicle or solvent, which are safe and less toxic for various routes of administration.

In another embodiment the present invention provides pharmaceutical compositions of lipophilic and hydrophilic actives containing or utilizing Diethylene glycol monoethyl ether or other alkyl derivatives thereof as a primary vehicle or solvent, which are safe and less toxic for various routes of administration.

In yet another embodiment the present invention provides pharmaceutical compositions of pharmaceutical actives containing or utilizing Diethylene glycol monoethyl ether or other alkyl derivatives thereof as a primary vehicle or solvent, for use in parenteral, oral, dermal, nasal, and other dosage forms.

In still another embodiment the present invention provides pharmaceutical compositions of lipophilic and hydrophilic actives containing or utilizing Diethylene glycol monoethyl ether or other alkyl derivatives thereof as a primary vehicle or solvent, for use in parenteral, oral, dermal, nasal, and other dosage forms.

In another embodiment the present invention provides pharmaceutical compositions of pharmaceutical actives containing or utilizing Diethylene glycol monoethyl ether or other alkyl derivatives thereof as a primary vehicle or solvent, for use of administration via I.M and/or I.V route, oral, dermal, nasal, optic, and other routes of administration.

In yet another embodiment the present invention provides pharmaceutical compositions of lipophilic and hydrophilic actives containing or utilizing Diethylene glycol monoethyl ether or other alkyl derivatives thereof as a primary vehicle or solvent, for use of administration via I.M and/or I.V route, oral, dermal, nasal, optic, and other routes of administration.

In still another embodiment the present invention provides pharmaceutical compositions of pharmaceutical actives containing or utilizing Diethylene glycol monoethyl ether or other alkyl derivatives thereof as a primary vehicle or solvent, which also provides the function of a permeation enhancing agent.

In another embodiment the present invention provides pharmaceutical compositions of lipophilic and hydrophilic actives containing or utilizing Diethylene glycol monoethyl ether or other alkyl derivatives thereof as a primary vehicle or solvent, which also provides the function of a permeation enhancing agent.

In yet another embodiment the present invention provides pharmaceutical compositions of pharmaceutical actives containing or utilizing Diethylene glycol monoethyl ether or other alkyl derivatives thereof as a primary vehicle or solvent, which provides ease of application of the said pharmaceutical actives comparatively reduced pain at the site of injection via I.M and I.V route.

In still another embodiment the present invention provides pharmaceutical compositions of lipophilic and hydrophilic actives containing or utilizing Diethylene glycol monoethyl ether or other alkyl derivatives thereof as a primary vehicle or solvent, which provides ease of application of the said lipophilic and hydrophilic actives comparatively reduced pain at the site of injection via I.M and I.V route.

In Another embodiment the present invention provides pharmaceutical compositions of pharmaceutical actives containing or utilizing Diethylene glycol monoethyl ether or other alkyl derivatives thereof as a primary vehicle or solvent, which exist in different dosage forms with desired quality control and are especially free from toxicity problems encountered due to solvents.

In yet another embodiment the present invention provides pharmaceutical compositions of lipophilic and hydrophilic actives containing or utilizing Diethylene glycol monoethyl ether or other alkyl derivatives thereof as a primary vehicle or solvent, which exist in different dosage forms with desired quality control and are especially free from toxicity problems in the therapeutic dose of drugs and encountered due to solvents.

In still another embodiment the present invention provides pharmaceutical compositions of pharmaceutical actives containing or utilizing Diethylene glycol monoethyl ether or other alkyl derivatives thereof as a primary vehicle or solvent, which can be formulated into different dosage forms such as capsules, nasal sprays, gargles, dermal gels, and others, which, moreover, can be made into a soluble pellucid solution.

In Another embodiment the present invention provides pharmaceutical compositions of lipophilic and hydrophilic actives containing or utilizing Diethylene glycol monoethyl ether or other alkyl derivatives thereof as a primary vehicle or solvent, which can be formulated into different dosage forms such as capsules, nasal ocular, otic deliveries, gargles, dermal gels, and others, which, moreover, can be made into a soluble pellucid solution.

In yet another embodiment the present invention provides pharmaceutical compositions of pharmaceutical actives containing or utilizing Diethylene glycol monoethyl ether or other alkyl derivatives thereof as a primary vehicle or solvent, which are comparatively less toxic and at the same time would be excreted out easily without causing damage to any organ, especially kidney, as well as would not get accumulated in any part of the body.

In still another embodiment the present invention provides pharmaceutical compositions of lipophilic and hydrophilic actives containing or utilizing Diethylene glycol monoethyl ether or other alkyl derivatives thereof as a primary vehicle or solvent, which are non-toxic and at the same time would be excreted out easily without causing damage to any organ, especially kidney, as well as would not get accumulated in any part of the body.

In another embodiment the present invention provides pharmaceutical compositions of pharmaceutical actives containing or utilizing Diethylene glycol monoethyl ether or other alkyl derivatives thereof as a primary vehicle or solvent, which provides transparent and less viscous parenteral solutions.

In yet another embodiment the present invention provides pharmaceutical compositions of lipophilic and hydrophilic actives containing or utilizing Diethylene glycol monoethyl ether or other alkyl derivatives thereof as a primary vehicle or solvent, which provides transparent and less viscous parenteral solutions.

In still another embodiment the present invention provides pharmaceutical compositions of pharmaceutical actives containing or utilizing Diethylene glycol monoethyl ether or other alkyl derivatives thereof as a primary vehicle or solvent, which exhibit better bioavailability in comparison to conventional compositions containing such pharmaceutical actives.

In another embodiment the present invention provides pharmaceutical compositions of lipophilic and hydrophilic actives containing or utilizing Diethylene glycol monoethyl ether or other alkyl derivatives thereof as a primary vehicle or solvent, which exhibit better bioavailability in comparison to conventional compositions containing such lipophilic and hydrophilic actives.

In yet another embodiment the present invention provides pharmaceutical compositions of pharmaceutical actives containing or utilizing Diethylene glycol monoethyl ether or other alkyl derivatives thereof as a primary vehicle or solvent, wherein the said pharmaceutical actives are not milled or micronized.

In still another embodiment the present invention provides pharmaceutical compositions of lipophilic and hydrophilic actives containing or utilizing Diethylene glycol monoethyl ether or other alkyl derivatives thereof as a primary vehicle or solvent, wherein the said lipophilic and hydrophilic actives are not milled or micronized.

In another embodiment the present invention provides pharmaceutical compositions of pharmaceutical actives containing or utilizing Diethylene glycol monoethyl ether or other alkyl derivatives thereof as a primary vehicle or solvent, which preferably contains preservatives and buffers to maintain its pH.

In yet another embodiment the present invention provides pharmaceutical compositions of lipophilic and hydrophilic actives containing or utilizing Diethylene glycol monoethyl ether or other alkyl derivatives thereof as a primary vehicle or solvent, which preferably contains preservatives and buffers to maintain its pH.

DETAILED DESCRIPTION OF THE INVENTION

As mentioned hereinbefore, the primary object and embodiment of the present invention lies in providing pharmaceutical compositions of pharmaceutical or lipophilic/hydrophilic actives in desired pellucid clear solution form for their use in formulation of various dosage forms, which includes parenteral/injectable form for use as intramuscular and/or intravenous administration, as well as for use as a preformed solution/liquid for filling in and preparation of capsules, tablets, nasal sprays, gargles, ocular delivery, otic delivery applications and other dosage forms.

Further, as mentioned hereinbefore, the primary object and embodiment of the present invention is realized through utilization of Diethylene glycol monoethyl ether or other alkyl derivatives thereof as a primary vehicle or solvent in the formulation of pharmaceutical compositions comprising such pharmaceutical or lipophilic actives.

By definition, a pharmaceutical active, referred to herein in the specification is a substance that is biologically active. It is also commonly referred to as a Pharmaceutically Active Ingredient (API), a Drug Substance or a Bulk Active. It is the active ingredient which is utilized in formulation of pharmaceutical compositions or Drug Products of such actives.

By definition, a lipophilic active, referred to herein in the specification are compounds which exhibit "Lipophilicity", meaning the ability of such compounds to dissolve in fats, oils, lipids, and non-polar solvents such as hexane or toluene. Such compounds generally are poorly soluble or insoluble in water and therefore "Hydrophobic". Barring a few exceptions the terms "Lipophilic" and "Hydrophobic" are synonymous.

By definition, a hydrophilic active, referred to herein in the specification are compounds which exhibit "hydrophilicity", meaning the ability of such compounds to dissolve in water and polar solvents.

The pharmaceutical and/or lipophilic/hydrophilic actives of the present invention are drug substances belonging to various pharmacological or therapeutic classes. By way of illustration, which, however, is non-limiting and should not be construed as limiting the scope of the invention, such pharmacological or therapeutic classes can be selected from:
1. Gastrointestinal and Hepatobiliary System Drugs:
   This can include Antacids, Antireflux Agents, Antiulcerants, GIT Regulators, Antiflatulents, Anti-inflammatories, Antispasmodics, Antidiarrheals, Laxatives, Purgatives, Digestives, Cholagogues, Cholelitholytics, Hepatic Protectors, Anorectal Preparations, Antiemetics and other Gastrointestinal Drugs.
2. Cardiovascular and Hematopoietic System Drugs:
   This can include Cardiac Drugs, Anti-anginal Drugs, ACE Inhibitors/Direct Renin Inhibitors, Beta Blockers, Calcium Antagonists, Angiotensin II Antagonists, Diuretics, Antidiuretics, Peripheral Vasodilators and Cerebral Activators, Vasoconstrictors, Dyslipidaemic Agents, Haemostatics, Anticoagulants, Other Antihypertensives and other Cardiovascular Drugs.
3. Respiratory System Drugs:
   This can include Antiasthmatic and COPD Preparations, Cough and Cold Preparations, Nasal Decongestants and other Respiratory System Drugs
4. Central Nervous System (CNS) Drugs:
   This can include Anxiolytics, Hypnotics and Sedatives, Antidepressants, Antipsychotics, Anticonvulsants, Antiparkinsonian Drugs, Analgesics (Opioid & Non-Opioid) and Antipyretics, Non Steroidal Anti Inflammatory Drugs (NSAIDs) and other CNS Drugs.
5. Musculo-skeletal System Drugs
6. Hormones, Steroids and Contraceptive Agents
7. Anti-infective Drugs:
   This can include Systemic Antibiotics, Antifungals, Antivirals, Antimalarials, Antiamoebics, Antiprotozoal agents, Anti-tuberculars, Antibacterial Combinations, Macrolides and other anti-infectives
8. Oncology Drugs
9. Genito-urinary Drugs
10. Endocrine and Metabolic System Drugs
11. Vitamins and Minerals
12. Nutritional Drugs
13. Ophthalmic (Eye) Drugs
14. Drugs for Ear, Nose, Mouth/Throat
15. Dermatological Drugs
16. Anesthetics—Local and General
17. Allergy and Immune System Drugs
18. Antidotes, Detoxifying agents and Drugs used in Substance Dependence
19. Intravenous and other Sterile Solutions
20. Miscellaneous Drugs and Compounds As per the embodiments of the present invention, the following pharmaceutical and/or lipophilic actives or drugs or compounds, which, however, is non-limiting and should not be construed as limiting the scope of the invention, belonging to various pharmacological or therapeutic classes can be solubilized in Diethylene glycol monoethyl ether or other alkyl derivatives thereof to provide pharmaceutical compositions, which exhibit good physical stability.
1. Gastrointestinal and Hepatobiliary System Drugs:
   a) Antacids, Antireflux agents and Antiulcerants: Famotidine, Misoprostol, Pantoprazole, Rabeprazole, Domperidone, Omeprazole, Lansoprazole Dexlansoprazole etc.
   b) GIT Regulators, Antiflatulents and Anti-inflammatories: Mesalazine, Metoclopromide, Mosapride etc.
   c) Antispasmodics: Drotaverine
   d) Antidiarrheals: Loperamide
   e) Laxatives and Purgatives: Bisacodyl
   f) Cholagogues, Cholelitholytics and Hepatic Protectors: Metadoxine
   g) Antiemetics: Domperidone
   h) Other Gastrointestinal Drugs: Trifluoperazine
2. Cardiovascular and Hematopoietic System Drugs:
   a) Cardiac Drugs: Adenosine, Digoxin, Lidocaine, Propafenone etc.
   b) Anti-anginal Drugs: Diltiazem HCl, Nicorandil, Nifedipine etc.
   c) ACE Inhibitors/Direct Renin Inhibitors: Captopril, Enalapril, Fosinopril, Lisinopril, Losartan, Ramipril etc.
   d) Beta Blockers: Labetelol, Sotalol, Nebivolol, Amplodipine etc.
   e) Calcium Antagonists: Amplodipine Besylate, Lacidipine
   f) Diuretics: Acetazolamide, Spironolactone, Torasemide etc.
   g) Peripheral Vasodilators and Cerebral Activators: Isoxsuprine, Nimodipine etc.
   h) Dyslipidaemic Agents: Bezafibrate, Atorvastatin, Bezafibrate, Rosuvastatin, Lovastatin, Simvastatin, Somatostatin etc.
   i) Anticoagulants: Cilostazol
   j) Other Antihypertensives and other Cardiovascular Drugs: Doxazocin, Prazocin, Reserpine etc.
3. Respiratory System Drugs:
   a) Antiasthmatic and COPD Preparations: Beclomethazone, Beclonetasone, Budesonide, Fluticazone, Ipratomium Bromide etc.
   b) Cough and Cold Preparations: Codeine, Dextromethorphan, Mesna etc.
   c) Nasal Decongestants and other Respiratory System Drugs: Oxymetazoline
4. Central Nervous System (CNS) Drugs:
   a) Anxiolytics: Alprazolam, Buspirone, Chlordiazepoxide, Clobazem, Clonazepam, Diazepam, Lorazepam, Hydroxyzine, Pregabalin etc.
   b) Hypnotics and Sedatives: Midazolam, Nitrazepam etc.
   c) Antidepressants: Bupropion Hydrochloride, Clomipramine, Doxepin, Fluoxetine, Mianserin etc.
   d) Antipsychotics: Clozapine, Lamotrigine, Olanzapine, Quetiapine, Valproic acid etc.
   e) Anticonvulsants: Carbamazepine, Clonazepam, Clobazam, Diazepam, Lamotrigine, Levetiracetam Phenytoin, Pregabalin, Dimenhydrinate etc.
   f) Analgesics (Opioid & Non-Opioid) and Antipyretics: Buprenorphine, Pentazocin etc.
   g) Non Steroidal Anti Inflammatory Drugs (NSAIDs): Buprenorphine, Pentazocine, Aceclofenac, Indometacin, Ibuprofen, Ketorolac, Lornoxicam, Mefenamic acid, Nimesulide, Piroxicam, Tenoxicam, Flunarizine, Citicoline, Mecobalamin, Pyritinol, Piracetam, Leflunomide, Celecoxib, Eterocoxib, Tilmacoxib, Acetaminophen, Levosulpiride etc.
5. Musculo-skeletal System Drugs: Chloroquine, Allopurinol, Baclofen, Glycopyrronium Bromide, Thiocolchicoside Tizanidine, Neostigmine, Diacerein, Tolperisone, Eperisone etc.
6. Hormones, Steroids and Contraceptive Agents: Testosterone, Estradiol, Ethinyl estradiol, Mesterolone, Allylestrenol, Estrdiol, Hydroxy-Progesterone Caproate, Medroxy-Progesterone, Norethisterone, Progesterone, Betamethasone, Hydrocortisone, Methyl Prednisolone, Prednisolone, Triamcinolone, Clomifene, Octreotide, Nandrolone, Levonorgestrel etc.

7. Anti-infective Drugs:
   Systemic Antibiotics, Antifungals, Antivirals, Antimalarials, Antiamoebics, Antiprotozoal agents, Anti-tuberculars, Antibacterial Combinations, Macrolides and other anti-infectives: Fluconazole, Voriconazole Tobramycin, Cefoperazone, Cefotaxime, Cefprozil, Erthyromycin, Ciprofloxacin, Ofloxacin, Tetracycline, Metronidazole, Ornidazole, Rifampicin, Vancomycin, Cycloserine, Protionamide, Isoniazide, Clotrimazole, Fluconazole, Itraconazole, Griseofulvin, Ketoconazole, Terbinafine, Ketoconazole, Acyclovir, Ganciclovir, Levamisole, Mebendazole, Artemether, Artesunate, Hydroxychloroquine, Mefloquine, Metronidazole, Furazolidine, Artesunate, Arteether, Artemether etc.
8. Oncology Drugs: Dacarbazine, Doxorubicin, Vinblastine Sulphate, Bleomycin, Etoposide, Melphalan, Paclitaxel, Vincristine sulfate, Amifostine, Anastrazole, Leuprolide etc.
9. Genito-urinary Drugs: Miconazole, Methylergometrine, Tadalafil, Tamsulosin, Calcitriol etc.
10. Endocrine and Metabolic System Drugs: Orlistat, Alfacalcidol etc.
11. Vitamins and Minerals: Vitamin K, Cholecalciferol, Retinol, Other Vitamins A, D & E.
12. Miscellaneous Drugs and Compounds: Aldosterone receptor Antagonists—Eplerenone, Spironolactone etc As mentioned hereinbefore, the aforementioned pharmaceutical or lipophilic actives can be solubilized into Diethylene glycol monoethyl ether or other alkyl derivatives thereof to provide a clear and transparent stable liquid solution, which can be used as such directly for formulation of injectable solutions for parenteral delivery; or which can be matrixed with pharmaceutically acceptable adjuvants into a tablet form for oral administration; or else which can be use as a preformed solution/liquid for filling in and preparation of capsules, tablets, nasal sprays, gargles, dermal applications ocular, otic and other dosage forms. In such cases, the clear and transparent stable liquid solution can be either used as a single drug preparation or can be given in combination with other suitable drugs for the requisite pharmacological actions.

While the invention is primarily illustrated with respect to Diethylene glycol monoethyl ether, otherwise known also as 2-(2-Ethoxyethoxy)ethanol, CARBITOL™, DE Solvent, Diethylene glycol ethyl ether, Ethyldiglycol or Transcutol and having the structure shown below,

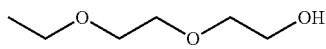

however, other alkyl derivatives can also be equally utilized in the present invention and a person skilled in the art would have no difficulty in embracing the other alkyl derivatives for working of the invention. Typical examples of other alkyl derivatives are Diethylene glycol monomethyl ether, Diethylene glycol mono-n-propyl ether, Diethylene glycol mono-iso-propyl ether, Diethylene glycol mono-n-butyl ether, Diethylene glycol mono-iso-butul ether, and Diethylene glycol mono-n-hexyl ether.

Diethylene glycol monoethyl ether is less viscous and safe. It has inherent viscosity of about 3.11 cps. It is soluble in water. The density of Diethylene glycol monoethyl ether is 0.985 to 0.991. Diethylene glycol monoethyl ether is less dense than water thereby making it easily flowable. As the compound has less viscosity it can be used for preparations of compositions which are having an easy syringability and thus advantageous to withdraw from vials or ampoules by the healthworkers. Further the same advantage offers doctors with its less painful impact and also less volume of liquid could be administered for the drug products in the therapeutic concentration through parenteral routes.

Of the various vehicles known in the art including various organic solvents, oils and oil-water mixtures for solubilizing the aforementioned pharmaceutical actives including lipophilic actives and poorly water soluble drugs and steroids, Diethyleneglycol monoethyl ether provides an efficient solubilizing activity and drug permeation activity which can avoid most, if not all the limitations/problems/concerns associated with utilization of the said vehicles known in the art for formulation of pharmaceutical compositions.

The wide range of pharmaceutical or lipophilic actives, described hereinbefore, namely the following—Antacids, Antireflux agents and Antiulcerants, GIT Regulators, Antiflatulents, Anti-inflammatories, Antispasmodics, Antidiarrheals, Laxatives, Purgatives, Cholagogues, Cholelitholytics, Hepatic Protectors, Anorectal Preparations, Antiemetics, and Other Gastrointestinal Drugs; Cardiac Drugs, Antianginal Drugs, ACE Inhibitors/Direct Renin Inhibitors, Beta Blockers, Calcium Antagonists, Angiotensin II Antagonists, Other Antihypertensives, Diuretics, Antidiuretics, Peripheral Vasodilators and Cerebral Activators, Vasoconstrictors, Dyslipidaemic Agents, Haemostatics, Anticoagulants and Other Cardiovascular Drugs; Antiasthmatic and COPD Preparations, Cough and Cold Preparations, Nasal Decongestants and other Respiratory System Drugs; Anxiolytics, Hypnotics and Sedatives, Antidepressants, Antipsychotics, Anticonvulsants, Antiparkinsonian Drugs, Analgesics (Opioid & Non-Opioid) and Antipyretics, NSAIDs and Other CNS Agents, Musculo-skeletal System Drugs, Hormones, Steroids and Contraceptive Agents, Antibiotics, Antifungals, Antivirals, Antimalarials, Antiamoebics, Antiprotozoal agents, Antituberculars, Antibacterial Combinations, Macrolides and other Anti infectives, Oncology Drugs, Drugs related to Genito-urinary, Endocrine & Metabolic System Drugs, Vitamins and Minerals, Nutrition Drugs belonging to Eye, Nose, Ear & Mouth/Throat, Dermatologicals, Anesthetics—Local and General, Drugs belonging to Allergy and Immune System, Antidotes, Detoxifying Agents & Drugs used in Substance Dependence, Intravenous and other Sterile Solutions and various Miscellaneous Therapeutic Category Drugs—showed highly selective solubility in the vehicle or solvent, Diethyleneglycol monoethyl ether or other alkyl derivatives thereof.

The selective vehicle or solvent, Diethylene glycol monoethyl ether or other alkyl derivatives thereof is typically employed in an amount of 25% to 30% by weight of the pharmaceutical composition containing the aforementioned pharmaceutical or lipophilic actives. The penetrating cum solubilization activity of Diethylene glycol monoethyl ether is very effective when such pharmaceutical compositions are used for their therapeutic use. The pharmaceutical compositions comprising Diethylene glycol monoethyl ether or other alkyl derivatives are found to provide better chemical and biological stability to the said compositions.

The pharmaceutical compositions containing the aforementioned pharmaceutical or lipophilic actives may in addition to Diethylene glycol monoethyl ether or other alkyl derivatives contain buffers, for maintenance of pH. Examples of suitable buffers that can be employed are 0.1 N Sodium hydroxide, Acetic acid, Sodium citrate, Potassium chloride, Sodium chloride, Citric acid, Sodium bicarbonate, L-Arginine, Tris buffers, Cholic acid Derivatives, Amino acid Derivatives etc.

The pharmaceutical compositions containing the aforementioned pharmaceutical or lipophilic actives may in addition to Diethylene glycol monoethyl ether or other alkyl derivatives contain preservatives, which are typically employed in an amount of 0.001% to 2% by weight of the composition. Examples of preservatives that can be used are Benzyl alcohol, Methyl paraben, Propyl paraben, Thiomerosol, Phenyl mercuric salts (acetate, borate, nitrate), Chlorobutanol, Meta-cresol etc. Typically Benzyl alcohol is employed in an amount of 0.01% to 2% by weight of the composition, Methyl paraben is employed in an amount of 0.18% to 0.2% by weight of the composition, Propyl paraben is employed in an amount of 0.01 to 0.02% by weight of the composition, and Thiomerosol is employed in an amount of 0.001% to 0.01% by weight of the composition. The preservatives also help in maintenance of the stability of the compositions.

The pharmaceutical compositions containing the aforementioned pharmaceutical or lipophilic actives may in addition to Diethylene glycol monoethyl ether or other alkyl derivatives contain antioxidants or chelating agents or stabilizers. Examples of antioxidants that can be employed are Ascorbic acid, Ascorbyl palmitate, Thioglycerol and its derivatives, Sodium bisulphate, Sodium metabisulphite, Sodium formaldehyde sulphoxylate, Thiourea, Ascorbic acid ester, BHT (Butylated hydroxyl toluene), Tocopherols etc. Typically Ascorbic acid is employed in an amount of 0.02% to 0.1% by weight of the composition, Ascorbyl palmitate is employed in an amount of 0.5% to 2% by weight of the composition, Sodium bisulphate is employed in an amount of 0.1% to 0.15% by weight of the composition, Sodium metabisulphite is employed in an amount of 0.1% to 0.15% by weight of the composition, Sodium formaldehyde sulphoxylate is employed in an amount of 0.1% to 0.15% by weight of the composition, Thiourea is employed in an amount of 0.004% to 0.005% by weight of the composition, Ascorbic acid ester is employed in an amount of 0.1% to 0.15% by weight of the composition, BHT is employed in an amount of 0.005% to 0.02% by weight of the composition, and Tocopherols are employed in an amount of 0.05% to 0.075% by weight of the composition. Chelating agents like Ethylene diamine tetraacetic acid in an amount of 0.01% to 0.075% by weight of the composition are typically employed and stabilizers like Maleic acid or Malate salts may be employed.

The pharmaceutical compositions containing the aforementioned pharmaceutical or lipophilic actives may in addition to Diethylene glycol monoethyl ether or other alkyl derivatives contain other appropriate adjuvants or excepients, based on the dosage forms.

The pharmaceutical compositions containing the aforementioned pharmaceutical or lipophilic actives may in addition to Diethylene glycol monoethyl ether or other alkyl derivatives contain other pharmaceutically acceptable co-solvents. Water can also be added in minimal quantity to make the compositions more fluidic.

The versatility of the selective solubilizing agent diethylene glycol monoethyl ether and a like solvent enables formulation for lipophilic actives which could be used as injectable both intravenously and intramuscularly use as well as for application in various pharmaceutical dosage compositions thereby providing for its diverse application of this drugs for treating diverse diseases and for alleviating the sickness of mammals effectively.

The wide range of the drugs that can be effectively solubilized by Diethylene glycol monoethyl ether or other alkyl derivatives and formulated into suitable pharmaceutical compositions or dosage forms are the following, which, however, is non-limiting as far as the scope of the invention, is concerned.

Class I: Pharmaceutical Actives or Drugs Which are Difficult to Solubilize

As mentioned hereinbefore, there are certain pharmaceutical actives or drugs, which are difficult to solubilize and often require toxic vehicles for solubilization and may further require unwanted excipients for formulation into suitable dosage forms.

Such pharmaceutical actives or drugs can be effectively solubilized by utilization of Diethylene glycol monoethyl ether or other alkyl derivatives as a primary vehicle or solvent, to provide clear, transparent, non hazy solutions of the said pharmaceutical actives or drugs in the said vehicle or solvent, which are further less viscous and are 'ready to use' for parenteral administration through I.V., I.M. or other routes of injection or can be used for formulation of various other dosage forms of the pharmaceutical actives or drugs, such as for example, capsules, tablets, nasal sprays, gargles, dermal applications, gels, ocular, otic, liquid oral dosage forms and other dosage forms. Further, when administered parenterally, the solutions are easily flowable, easily syringable, easy to inject and cause less pain at the site of the injection and are therefore, beneficial not only to the patients bit also to the doctors/physicians/nurses. Furthermore, the pharmaceutical compositions are safe and less toxic, when administered through various routes, especially if administered parenterally. In addition, utilization of Diethylene glycol monoethyl ether or other alkyl derivatives enhances the chemical and biological stability of the pharmaceutical actives or drugs and also offers a better permeation of such actives or drugs.

Diethylene glycol monoethyl ether or other alkyl derivatives offers comparatively less viscosity (of less than 7-8 cps if used alone in the composition and less than 15 cps if used as co solvents in few examples) if administered through parenteral routes.

The various pharmaceutical actives or drugs, belonging to this class, to name a few are the following, which again to reiterate is non-limiting as far as the scope of the invention, is concerned.

I.1) Progesterone (Steroids & Hormones)

Progesterone also known as P4 (pregn-4-ene-3, 20-dione) is a C-21 steroid hormone involved in the female menstrual cycle, pregnancy (supports gestation) and embryogenesis of humans and other species. Progesterone belongs to a class of hormones called progestogens, and is the major naturally occurring human progestogen. The molecular structure of progesterone is as:

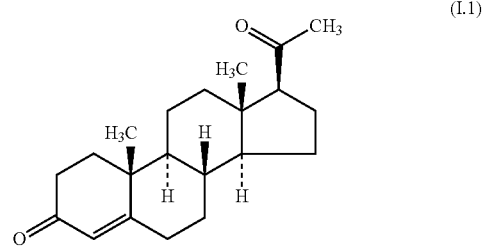

(I.1)

It is white crystalline powder insoluble in water. The solubility profile of Progesterone in water is <0.1 g/100 ml at 19° C. It is freely soluble in dehydrated alcohol, sparingly soluble in vegetable oils and acetone. It is available in micronized form as an oily intramuscular injection prepared in sesame oil according to USP which is viscous in nature and can be painful at the site of injection. It differs from other commonly used steroids in that it is irritating at the place of injection.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injections for rapid onset of action when required to provide earliest result into the patient as well as can be used for formulation of different dosage forms like capsules, gels, topical gels, vaginal suppository, liquid oral dosage forms etc. The solution may additionally contain preservatives and buffers for maintenance of pH.

I.2$_A$) Nandrolone Decanoate (Steroids & Hormones)

Nandrolone (19-nortestosterone, I.2) is an anabolic steroid that may be present naturally in the human body. Nandrolone is most commonly sold commercially as its decanoate ester and as a phenyl propionate ester.

Nandrolone decanoate (DI) is synthetic derivative of testosterone indicated for the management of the anemia of renal insufficiency and has been shown to increase hemoglobin and red cell mass. The chemical formula of Nandrolone decanoate is as Estr-4-en-3-one, 17-[(1-oxodecyl)oxy]-,(17b)-,17b-Hydroxyestr-4-en-3-one decanoate The molecular formula of decanoate ester is $C_{28}H_{44}O_3$ and the molecular structure is given as:

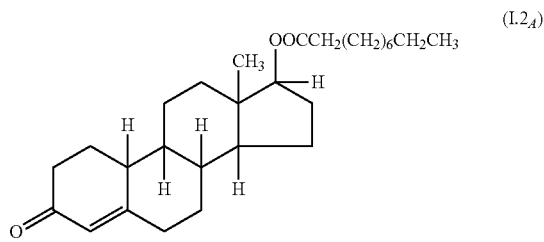

(I.2$_A$)

Nandrolone decanoate ($C_{28}H_{44}O_3$) occurs as a fine, white to creamy white, crystalline powder. It is odorless, or may have a slight odor. Nandrolone decanoate is soluble in chloroform, in alcohol, in acetone, and in vegetable oils. It is practically insoluble in water. As Nandrolone decanoate, it is available as a sterile oleaginous solution in which sesame oil is administered. It is available in dose of 100 mg/ml in which up to 10% of benzyl alcohol is used as solubilizer as well as preservative. While, benzyl alcohol can be used in 2% to 4% as preservative in parenterals but at 10% of concentration it shows anesthetics effect. While sesame oil makes the injection more viscous, this can be painful at the site of injection.

By utilizing the vehicle or solvent of the present invention solvent, Diethylene glycol monoethyl ether or other alkyl derivatives, a transparent, non hazy as well as less viscous solution is obtained, which can be useful as I.V. bolus injection or Depot I.M. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

I.2$_B$) Nandrolone Phenyl Propionate (Steroids & Hormones)

Nandrolone phenyl propionate is an I.M. injectable form of the anabolic steroid Nandrolone. It is chemically designated as 17b-hydroxyestr-4-en-3-one 17-(3-phenylpropionate) and the chemical structure is given as:

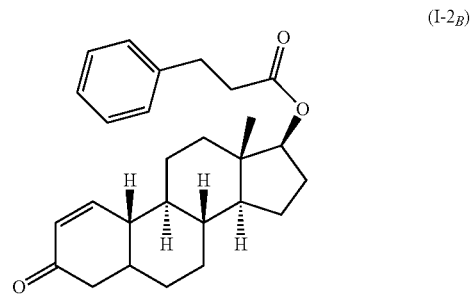

(I-2$_B$)

It is a white to creamy white, crystalline powder, practically insoluble in water. Nandrolone phenyl propionate is active for about a week. Esterified steroids are less polar than free steroids, and are absorbed more slowly from the area of injection. Once in the bloodstream, the ester is removed to yield free (active) 47aphtha47ol. Esterified steroids are designed to prolong the window of therapeutic effect following administration, allowing for a less frequent injection schedule compared to injections of free (unesterified) steroid. Nandrolone is not C-17 alpha alkylated, and not known to have hepatotoxic effects in healthy subjects. Nandrolone Phenyl Proprionate is available in select human human drug markets in compositions and dosage containing 25 mg/mL or 50 mg/ML of the steroid dissolved in oil.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injections for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

I.3, I.3$_A$, I.3$_B$) Testosterone and its Salt Forms i.e. Testosterone Enanthate and Testosterone Cypionate (Steroids & Hormones)

Testosterone is an anabolic steroid hormone which is also used in prevention of Osteoporosis. Its molecular formula is $C_{19}H_{28}O_2$ (M.W=288.4) with the following structure as:

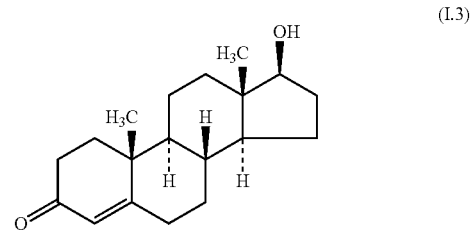

(I.3)

It is white crystalline or yellowish white crystals, practically insoluble in water, and fatty oils. It has low bioavailability with half-life of 2 to 4 hrs and metabolism occurs in liver, testis and prostate. It is useful in testosterone replacement therapy in male hypo gonadal disorders, and also improves type 2 diabetes.

Testosterone enanthate is a derivative of the primary endogenous androgen testosterone, for intramuscular administration. In their active form, androgens have a 17-beta-hydroxy group. Esterification of the 17-beta-hydroxy group increases the duration of action of testosterone; hydrolysis to free testosterone occurs in vivo.

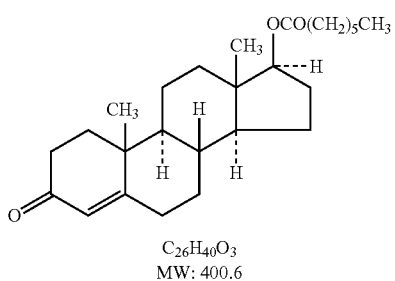

(I.3$_A$)

C$_{26}$H$_{40}$O$_3$
MW: 400.6

Testosterone enanthate (C$_{26}$H$_{40}$O$_3$) (M.W. 400.60) is a white or creamy white, crystalline powder. It is odorless or has a faint odor characteristic of heptanoic acid. It is insoluble in water, very soluble in ether and soluble in vegetable oils. Testosterone Enanthate Injection is a clear, colorless to pale yellow sterile oleaginous solution of testosterone enanthate for intramuscular use. Each mL contains: Testosterone Enanthate 200 mg, Chlorobutanol (Chloral derivative) 0.5% in Sesame Oil q.s.

Testosterone cypionate is the lipophilic active 17(beta)-cyclopentylpropionate ester of the androgenic hormone testosterone. It is a white or creamy white crystalline powder freely soluble in ether with the chemical formula is androst-4-en-3-one, 17-(3-cyclopentyl-1-oxopropoxy)-, (17β)-. Its molecular formula is C$_{27}$H$_{40}$O$_3$ with the molecular weight 412.61.

The structural formula is represented below:

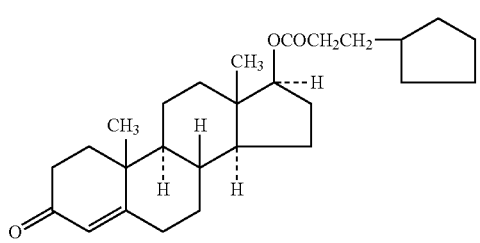

(I.3$_B$)

It is available in parenteral form in two strengths, 100 mg/ml and 200 mg/ml. It is recommended to inject the drug in the buttocks after every 7-12 days for maximum results. At a time, whole of testosterone will remain bound to the protein while only 2% will be available and is secreted in to the blood. It is indicated for replacement therapy in the male in conditions associated with symptoms of deficiency or absence of endogenous testosterone.

The ester forms are available as oil based depot type parenteral preparation in which sesame oil or cottonseed oil is used, which might cause pain as well as allergic reaction This may lead to abscess formation, sores and some skin infections. Moreover, a single site cannot be used for injection every time. Due to their bulkiness/viscous nature it may be difficult to syringe it.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injection for rapid onset of action when required to provide earliest result into the patient. The solution may additionally contain preservatives and buffers for maintenance of pH.

I.4) Norethisterone Enantate (Steroids & Hormones)

Norethisterone enantate is a synthetic progestin, contraceptive usually given through intragluteal route as a single injection in strength of 200 mg/ml. It continuously releases its progestin into the bloodstream over a period of eight weeks (2 months). A second and final injection may be given eight weeks after the first injection if necessary. Norethisterone enantate is only used as a short-term method of contraception in certain circumstances.

It is chemically designated as 17alpha-Ethynyl-19-nortestosterone 17-heptanoate and the molecular structure is given as:

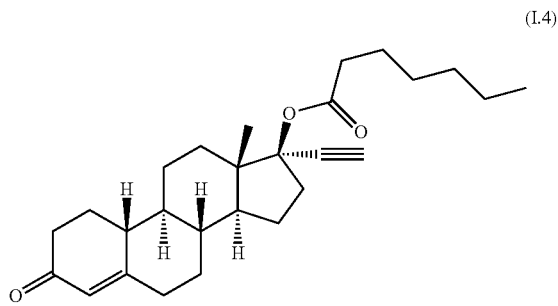

(I.4)

It is a white to creamy white, crystalline powder; practically insoluble in water; freely soluble in acetone, methanol, dehydrated ethanol, dioxane and ether; slightly soluble in light petroleum. According to U.S. Pat. No. 7,025,979, the invention shows a formulation for male contraception comprising a progestin possessing both estrogenic and androgenic properties is remarkably effective for spermatogenesis suppression in males. The progestin Norethisterone (NET), particularly its derivatives Norethisterone acetate and Norethisterone enanthate in sufficient doses induce oligozoospermia or azoospermia in males.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topicals, liquid oral dosage forms etc. The solution may additionally contain preservatives and buffers for maintenance of pH.

I.5) 17β Estradiol (Steroids & Hormones)

Estradiol (E2 or 17β-estradiol) is a sex hormone which is abbreviated E2 as it has two hydroxyl groups in its molecular structure. The chemical name of this lipophilic active is (17β)-estra-1, 3, 5(10)-triene-3, 17-diol with molecular formula and molecular structure is as:

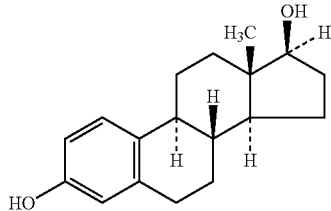

(I.5)

It is used, either as an injection or topically, in the treatment of inflammation, allergy, collagen diseases, asthma, adrenocortical deficiency, shock, and some neoplastic conditions. This hormone is available as salt form like Estradiol Benzoate, Estradiol Cypionate, Estradiol valerate in parenteral forms which are used in treatment of female hypogandism. These salts are sparingly soluble in oil like sesame oil so it may be chances of stability problem.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topicals, transdermal discs, intravaginal rings, liquid oral dosage forms etc. The solution may additionally contain preservatives and buffers for maintenance of pH.

I.6) Fulvestrant (Steroids & Hormones)

Fulvestrant is an estrogen receptor antagonist as a drug for treatment of hormone receptor-positive metastatic breast cancer in postmenopausal women with disease progression following anti-estrogen therapy.

The chemical name is 7-alpha-[9-(4,4,5,5,5-penta fluoropentylsulphinyl) nonyl]estra-1,3,5-(10)-triene-3,17beta-diol. The molecular formula is $C_{32}H_{47}F_5O_3S$ and its structural formula is:

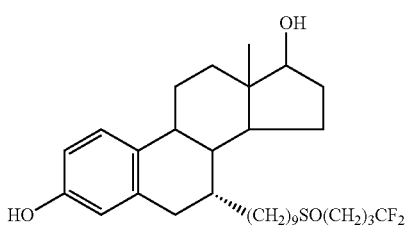

(I.6)

Fulvestrant is a white powder with a molecular weight of 606.77. It is available as injection for intramuscular administration. The solution for injection is a clear, colorless to yellow, viscous liquid. Fulvestrant is soluble in ethanol, DSMO, Dimethyl formamide and practically insoluble in water.

This injection contains up to 10% of benzyl alcohol which might act as an aesthetic level while castor oil USP is used as release rate modifier which can be viscous that can be painful at the time of injection and the solution might be appear yellowish color too. According to FDA drug approval summaries, injection site reaction and hot flashes were observed.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient. The solution may additionally contain preservatives and buffers for maintenance of pH.

In a similar way, Anabolic steroids like Boldenone Undecylanate, Drostanolone propionate, Trenbolone Acetate, Trenbolone Enanthate, Methenolone Enanthate, Methyl Testosterone can also be prepared as I.M and I.V. injectable forms by utilizing the vehicle or solvent of the present invention solvent, Diethylene glycol monoethyl ether or other alkyl derivatives to give a transparent, non hazy as well as less viscous solution.

I.7) Artemether (Antimalerial)

It is a methyl ether derivative of artemisinin, which is a peroxide lactone isolated from the Chinese antimalarial plant, *Artemisia annua*. It is also known as dihydroartemisinin methyl ether, but its correct chemical nomenclature is (+)-(3-alpha,5a-beta,6-beta,8a-beta, 9-alpha,12-beta,12aR)-decahydro-10-methoxy-3,6,9-trimethyl-3,12-epoxy-12H-pyrano(4,3-j)-1,2-benzodioxepin with the molecular structure as

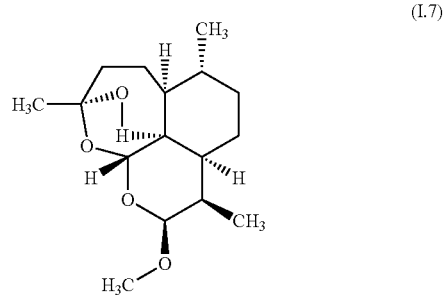

(I.7)

It is a white crystalline powder with a bitter taste; practically insoluble in water, soluble in chloroform, acetone, and alcohols. It is a relatively lipophilic and unstable drug. Artemether is highly effective against the blood schizonts of both malarial parasites *P. falciparum* and *P. vivax*. Its unique features are:

Unlike most other antimalarial, it lacks a nitrogen-containing heterocyclic ring system;

Is equally as effective as quinine in the treatment of severe malaria; and

Is as effective as quinine in the treatment of cerebral malaria.

It is available as I.M injection form at dose of 80 mg/mL for adult and accepted as 20 mg/ml for pediatric patients by WHO. The product available in the market is prepared in miglycol, Medium chain triglyceride oils which may be low viscous but are irritant at the site of injection.

By utilizing the vehicle or solvent of the present invention solvent, Diethylene glycol monoethyl ether or other alkyl derivatives, a transparent, non hazy solution is obtained, which can be useful as I.M as well as I.V. injections for rapid onset of action when required to provide earliest result into the patient. The solution may additionally contain preservatives and buffers for maintenance of pH. The solution can also be used for formulation of other dosage forms, such as capsules, gel, patches, liquid dosage forms etc.

I.8) Arteether (Antimalerial)

Arteether is the ethyl ether derivative of artemisinin, a natural product of the Chinese plant *Artemisia annua*. It is currently only used as a second line drug in severe cases of malaria as fast acting blood schizontocidal agent for *P. falciparum* malaria at the erythrocytic stage. The molecular formula is $C_{17}H_{28}O_5$ and molecular weight is 312.4. The molecular formula of Arteether is 10-Ethoxydecahydro-3,6, 9-trimethyl-3,12-epoxy-12H-pyrano[4,3-j]-1,2-benzodioxepin with molecular structure is given as:

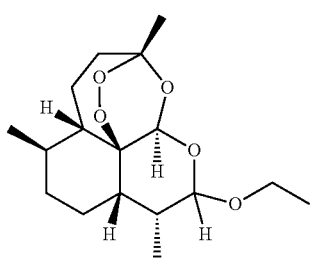

(I.8)

It is quite water insoluble, but very soluble in a variety of organic solvents. It is available in injection form in market as intramuscular application at the dose of 150 mg/2 ml.

In one of the parenteral formulation available in the market, it is manufactured by incorporation of ethyl oleate which is yellow color liquid, addition of alcohols ethyl alcohol, benzyl alcohol and group of preservatives which leads to high cost product as well as viscous formulation which can be irritant at site of injection. This problem can be solved by using the selected solvent in the present invention to prepare I.V. parenteral.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient. The solutions can be prepared in concentrations of 150 mg/ml or 75 mg/ml. The solution may additionally contain preservatives and buffers for maintenance of pH. The solution can also be used for formulation of other dosage forms, such as capsules.

I.9) Haloperidol (Antipsychotic)

Haloperidol is the first of the butyrophenone series of major antipsychotics. The chemical designation is 4-[4-(p-chlorophenyl)-4-hydroxypiperidino]-4'-fluorobutyrophenone and it has the following structural formula:

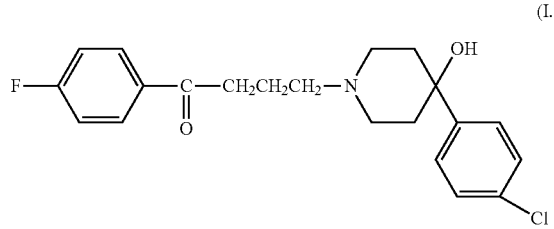

(I.9)

The product has very low solubility in water (1.4 mg/100 ml), but it is freely soluble in chloroform, benzene, methanol, acetone, and dilute acids. It is soluble in 0.1 N hydrochloric acid (3 mg/ml) with heating.

Haloperidol is available as a sterile parenteral form for intramuscular injection. The injection provides 5 mg haloperidol (as the lactate) and lactic acid for pH adjustment between 3.0-3.6. Haloperidol Injection is recommended for intramuscular administration only. Skin rash and injection site reaction has been found by use of this parenteral.

By utilizing the vehicle or solvent of the present invention solvent, Diethylene glycol monoethyl ether or other alkyl derivatives, not only a transparent, non hazy as well as less viscous solution is obtained, which can be useful as I.V. or I.M. injections for rapid onset of action when required to provide earliest result into the patient, but also the rashes at the site of injection is prevented. The solution can also be used for formulation of different dosage forms like capsules, tablets, nasal sprays, gargles, gels, topicals, liquid oral dosage forms etc. The solution may additionally contain preservatives and buffers for maintenance of pH.

I.10) Vitamin $D_3$ (Vitamins & Minerals)

Presently Cholecalciferol (Vitamin $D_3$) is available as oily viscous injectable which is painful when administered and needs to be modified into less viscous and painless injection.

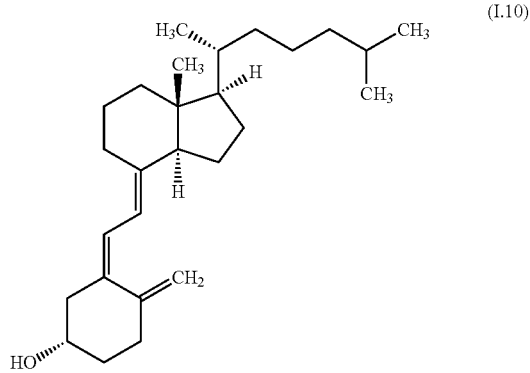 [SMILES: C=C1CC[C@H](O)C/C1=C/C=C1\CCC[C@]2(C)[C@@H]([C@H](C)CCCC(C)C)CC[C@@H]12]

(I.10)

By utilizing the vehicle or solvent of the present invention solvent, Diethylene glycol monoethyl ether or other alkyl derivatives, a transparent, non hazy as well as less viscous solution is obtained, which can be useful as I.M. injection [of 600,000 IU per ml and optionally containing preservatives and antioxidants] for rapid onset of action when required to provide earliest result into the patient. The solution can prevent issue damage and pain at the site of injection, caused by oily injections currently available in the market. I.V. infusion is also possible, since the safety of the same has been established. The solution is easily syringable and can be combined with calcium salts using water or mixed with co-solvents for combined therapy after homogenization. The solution can also be used for formulation of different dosage forms like capsules, tablets, nasal sprays, gargles, gels, topicals, liquid oral dosage forms etc. The solution may additionally contain preservatives and buffers for maintenance of pH.

A2) Medroxy Progesterone Acetate

Medroxyprogesterone acetate, also known as 17α-hydroxy-6α-methylprogesterone acetate, and commonly abbreviated as MPA, is a steroidal progestin, a synthetic variant of the human hormone progesterone. It is used as a contraceptive, in hormone replacement therapy and for the treatment of endometriosis as well as several other indications. It is chemically designated as 17α-hydroxy-6α-methylpregn-4-ene-3,20-dione acetate and molecular structure is:

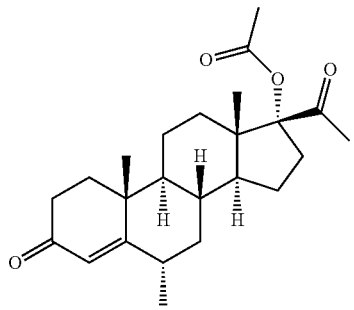

(A2)

MPA is a more potent derivative of its parent compound medroxyprogesterone. It is a white to off-white, odorless crystalline powder, stable in air, melting between 200° and 210° C. It is freely soluble in chloroform, soluble in acetone and in dioxane, sparingly soluble in alcohol and methanol, slightly soluble in ether and insoluble in water. It is available as Aqueous Suspension active by the parenteral and oral routes of administration. It is available as intramuscular injection in which each ml consists of 400 mg/ml MPA. The vehicle used as parenteral solvent is PEG 3350.

The viscosity of PEG 3350 is about 83 to 130 cps, which is more viscous and may be painful to patient at the time of injection. As it is available in suspension form, stability, particle size, and storage of the product are critical factors for handling.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injections for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

I.11) Allylestrenol (Steroids & Hormones)

It is a synthetic progestogen with progestational activity used to prevent threatened miscarriage, recurrent pregnancy loss and premature labor. In men, it has also been studied as a treatment for benign prostatic hyperplasia, with encouraging results. It is chemically denoted as (17β)-17-(prop-2-en-1-yl) estr-4-en-17-ol and the molecular structure is given as:

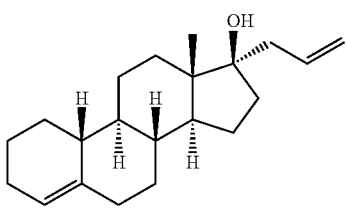

(I.11)

It is practically insoluble in water. According to U.S. Pat. No. 6,696,433, this sex steroid was prepared in injectable form by improving its solubility using beta cyclodextrin.

It is available in injectable form at dose of 250 mg/ml and as oral dosage form at dose of 5 mg per tablet in the market. By utilizing the vehicle or solvent of the present invention solvent, Diethylene glycol monoethyl ether or other alkyl derivatives, a transparent, non hazy as well as less viscous solution is obtained, which can be useful as I.M as well as I.V. injection for rapid onset of action when required to provide earliest result into the patient as well as can be used for formulation of different dosage forms like capsules, nasal sprays, gargles, gels, topicals, liquid oral dosage forms etc. The solution may additionally contain preservatives and buffers for maintenance of pH.

I.12, I.12$_A$) Etoricoxib and Tilmacoxib (Cox-2 Inhibitors)

Like any other COX-2 selective inhibitor, Eterocoxib selectively inhibits isoform 2 of the enzyme cyclooxygenase (COX-2). This reduces the generation of prostaglandins (PGs) from arachidonic acid. The chemical name of Etoricoxib is 5-chloro-6'-methyl-3-[4-(methylsulfonyl)phenyl]-2,3'-bipyridine with molecular structure as:

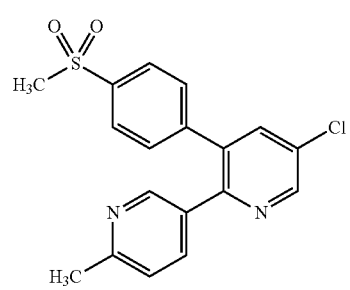

(I.12)

It is very low soluble in water about 3.3 mg/L. According to Indian Patent No. 146674, the invention was related to a clear, stable novel pharmaceutical preparation of selective cyclooxygenase II inhibitors (COX 2) inhibitors preferably in the parenteral form for the treatment of pain & inflammatory. In this invention, solvent Dimethyl Isosorbide (DMI) is used which was found to be irritant at site of application as well as during long term storage, there was possible crystal formation of the drug in the liquid.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, gels, patches, liquid oral dosage forms etc. The solution may additionally contain preservatives and buffers for maintenance of pH.

Other drugs under this category like Firocoxib, Mavacoxib, Robenacoxib, Cimicoxib that are used for veterinary can be also be compounded into parenteral preparation by utilization the vehicle or solvent of the present invention, Diethylene glycol monoethyl ether or other alkyl derivatives.

Newer drugs of this category like Tilmacoxib (I.12$_A$) which was found to be an effective chemo-preventive agent against rat experimental liver fibrosis can also be prepared as parenteral dosage form by using diethyleneglycol mono ethyl ether. The chemical name of Tilmacoxib is 4-(4-cyclohexyl-2-methyl-1,3-oxazol-5-yl)-2 fluorobenzenesulfonamide with molecular structure as:

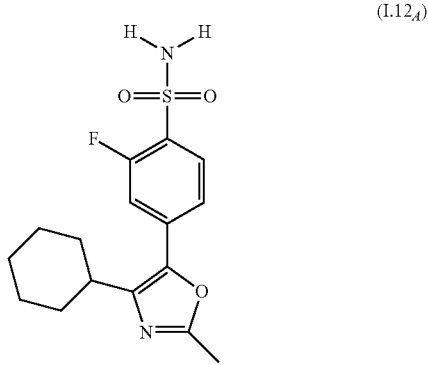 [SMILES: Cc1nc(C2CCCCC2)c(-c2ccc(S(N)(=O)=O)c(F)c2)o1]

(I.12$_A$)

Tilmacoxib is still new active without any dosage preparation available in the market.

Here also, by utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, gels, patches, liquid oral dosage forms etc. The solution may additionally contain preservatives and buffers for maintenance of pH.

I.13) Cyclosporine (Immunosuppressant)

Cyclosporine is an immunosuppressant drug widely used in organ transplantation to prevent rejection. It reduces the activity of the immune system by interfering with the activity and growth of T cells. Cyclosporine is a cyclic polypeptide immunosuppressant agent consisting of 11 amino acids. It is chemically designated as (E)-14,17,26,32-tetrabutyl-5-ethyl-8-(1-hydroxy-2-methylhex-4-enyl)-1,3,9,12,15,18,20,23,27-nonamethyl-11,29-dipropyl-1,3,6,9,12,15,18,21,24,27,30-undecaazacyclodotriacontan-2,4,7,10,13,16,19,22,25,28,31-undecaone and molecular structure is:

(I.13)

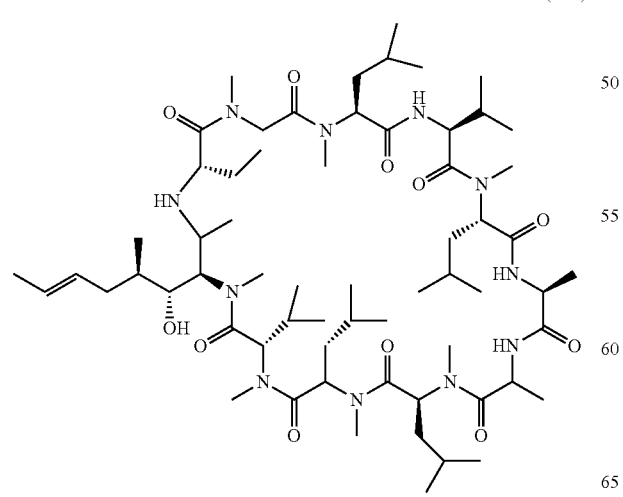

The drug exhibits very poor solubility in water, and, as a consequence, suspension and emulsion forms of the drug have been developed for oral administration and for injection, cyclosporine injection, USP, is available in a 5 mL sterile ampoule for I.V. administration in which Each mL contains: cyclosporine, USP 50 mg, Cremophor® EL (polyoxyethylated castor oil) 650 mg, alcohol about 32.9% by volume which must be diluted further with 0.9% Sodium Chloride Injection or 5% Dextrose Injection before use. As discussed earlier, Cremophor® EL was found to have acute anaphylactoid reaction and requires administration of antihistamines prior to the injection and thus the double injections cause discomfort to the patients.

By utilizing the vehicle or solvent of the present invention solvent, Diethylene glycol monoethyl ether or other alkyl derivatives, not only a transparent, non hazy as well as less viscous solution is obtained, which can be useful as I.V. or I.M. injections for rapid onset of action when required to provide earliest result into the patient, but also does not have the safety and toxicity issues associated with Cremophor® EL. The solutions can be prepared in concentrations of 25 mg/ml to 100 mg/ml. The solution can also be used for formulation of different dosage forms like capsules, tablets, liquid oral dosage forms etc. The solution may additionally contain preservatives and buffers for maintenance of pH.

I.14) Paclitaxel (Anticancer Agent)

Paclitaxel is a mitotic inhibitor used in cancer chemotherapy. When it was developed commercially by Bristol-Myers Squibb (BMS), the generic name was changed to Paclitaxel and the BMS compound is sold under the brand name Taxol®. In this formulation, Paclitaxel is dissolved in Cremophor EL and ethanol, as a delivery agent. Another formulation, in which paclitaxel is bound to albumin, is sold under the brand name Abraxane®, which is prepared using Nanotechnology and hence a costly technique, Paclitaxel is used to treat patients with lung, ovarian, breast, head and neck cancer, and advanced forms of Kaposi's sarcoma. Paclitaxel is also used for the prevention of restenosis.

Paclitaxel is chemically designated as (2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate and the molecular structure is given as:

(I.14)

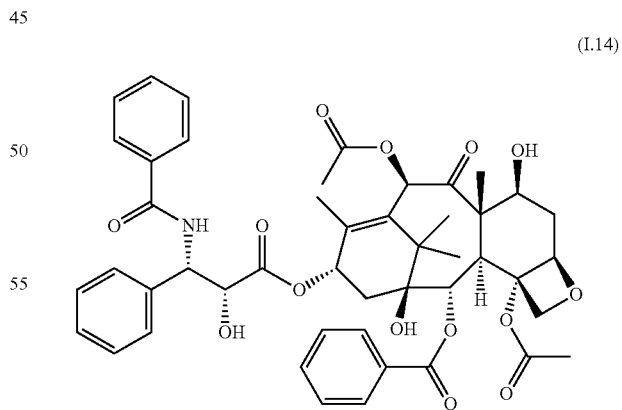

The nomenclature for Paclitaxel is structured on a tetracyclic 17-carbon (heptadecane) skeleton. Paclitaxel is a white to off-white crystalline powder with the empirical formula $C_{47}H_{51}NO_{14}$ and a molecular weight of 853.9. It is highly lipophilic, insoluble in water, and melts at around 216-217° C.

Paclitaxel Injection is a slightly yellow viscous solution. It is supplied as a nonaqueous solution intended for dilution with a suitable parenteral fluid prior to intravenous infusion. It is available in 30 mg (5 mL), 100 mg (16.7 mL), and 300 mg (50 mL) multidose vials. Each mL of sterile nonpyrogenic solution contains 6 mg paclitaxel, 527 mg of purified Cremophor® EL (polyoxyethylated castor oil) and 49.7% (v/v) dehydrated alcohol, USP. From the above formulation, it is easily to guess that how much painful would be the injection when given to the cancerous patient. It might be surprisingly advantage to prepare the injection of this highly lipophilic active by it's solubilizing in the present permeating enhancer without any reaction that might be possible to occur by Cremophor® EL.

It is now available and marketed as conjugation as a albumin complex. The technique to prepare the same is costly and is uneconomic and does not cater the need of the poor. Cancer is prevalent is various countries in vast majority of global population.

By utilizing the vehicle or solvent of the present invention solvent, Diethylene glycol monoethyl ether or other alkyl derivatives, not only a transparent, non hazy as well as less viscous solution is obtained, which can be useful as I.V. injections for rapid onset of action when required to provide earliest result into the patient, but also does not have the safety and toxicity issues associated with Cremophor® EL as well as does not involve the complex and expensive technology involved for making albumin based coplexes. The solution can also be used for formulation of different dosage forms like capsules, tablets, liquid oral dosage forms etc. The solution may additionally contain preservatives and buffers for maintenance of pH.

I.15) Piroxicam (Antirhuematic Actives for Musculo Skeletal System—Oxicams)

Oxicams are members of a class of NSAIDs that bind closely to plasma proteins. Most oxicams are unselective inhibitors of the cyclooxygenase (COX) enzymes, which includes Piroxicam. Its anti-inflammatory potency is similar to Indomethacin and analgesic action is greater than Aspirin. It has useful antipyretic property. Piroxicam is chemically designated as (8E)-8-[hydroxy-(pyridin-2-ylamino)methylidene]-9-methyl-10,10-dioxo-10λ6-thia-9-azabicyclo[4.4.0]deca-1,3,5-trien-7-one with molecular structure as:

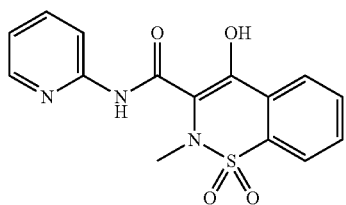

(I.15)

It is a white crystalline solid; sparingly soluble in water (23 mg/L at 22° C.), dilute acid and organic solvents; slightly soluble in alcohols and in aqueous alkalines. It is available as injection in dose of 20 mg/2 ml.

In U.S. Pat. No. 4,628,053; Invention relates to stabilized injection solutions of Piroxicam in which propylene glycol, ethanol and water as the solvent for parenteral administration which might be viscous and painful at the site of injection.

In U.S. Pat. No. 4,824,841, Invention relates to a process for the transformation of Piroxicam into an hydrated form suitable for Oral, topic or parenteral administration.

In U.S. Pat. No. 4,942,167, Aqueous pharmaceutical formulation containing lyophilized Piroxicam in Glycine as vehicle which is not transparent solution and stability can be issue.

In U.S. Pat. No. 5,420,124A, Invention relates to an injectable Piroxicam potassium composition which contains triethyleneglycol as a solvent and stabilizer.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topical, liquid oral dosage I.16) Clonazepam (Anticonvulsant)

Clonazepam is a benzodiazepine drug having anxiolytic, anticonvulsant, muscle relaxant, sedative, and hypnotic properties.

Clonazepam is classified as a high potency benzodiazepine. Clonazepam is a chlorinated derivative of nitrazepam. It is a light yellow crystalline powder. It has a molecular weight of 315.72 It is chemically designated as 5-(2-chlorophenyl)-7-nitro-2,3-dihydro-1,4-benzodiazepin-2-one and the molecular structure is given as:

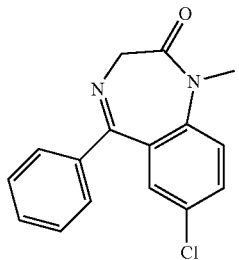

(I.16)

It is a light yellow crystalline powder insoluble in water, sparingly soluble in acetone and chloroform and slightly soluble in alcohol. It has a molecular weight of 315.72. Clonazepam was approved in the United States as a generic drug in 1997 and is now manufactured and marketed by several companies. Clonazepam is available as tablets and orally disintegrating tablets (wafers), oral solution (drops), as well as solution for injection or intravenous infusion. This injection is appearing as lightly greenish yellow solution.

For panic disorder, the initial recommended dose is 0.25 mg twice daily. This dose can be increased every three days in increments of 0.125-0.25 mg twice daily. The target dose for panic disorder is 1.0 mg per day, although some people benefit from doses up to a maximum of 4 mg per day. When a person stops taking Clonazepam, the drug should be gradually discontinued by decreasing the dose by 0.125 mg twice daily every three days.

Although, clonazepam is not FDA-approved for the treatment of post-traumatic stress disorder, doses in the range of 0.25-3 mg daily appears to help treat symptoms of this disorder. Daily dosages for the treatment of social phobia range from 1.0-2.5 mg, while the dosage to control mania may be as high as 10 mg daily.

By utilizing the vehicle or solvent of the present invention solvent, Diethylene glycol monoethyl ether or other alkyl derivatives, a transparent, non hazy as well as less viscous solution is obtained, which can be useful as I.V. injections for rapid onset of action when required to provide earliest result into the patient. The solution can also be used for formulation of different dosage forms like capsules, tablets, liquid oral dosage forms etc. The solution may additionally contain preservatives and buffers for maintenance of pH.

I.17) Diazepam (Anticonvulsant)

Diazepam is a benzodiazepine derivative chemically designated as 7-chloro-1,3-dihydro-1-methyl-5-phenyl-2H-1,4-benzodiazepin-2-one. It is a colorless crystalline compound, insoluble in water, with the following molecular structure:

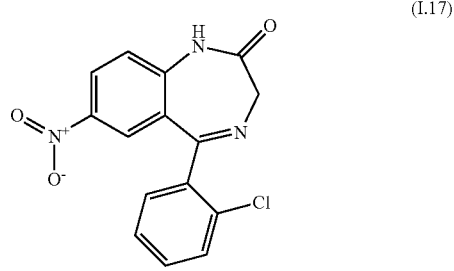 [SMILES: O=C1CN=C(c2ccccc2Cl)c2cc([N+](=O)[O-])ccc2N1]

(I.17)

Diazepam Injection, USP is a sterile, nonpyrogenic solution intended for intramuscular or intravenous administration. Each milliliter (mL) contains 5 mg diazepam; 40% propylene glycol; 10% alcohol; 5% sodium benzoate and benzoic acid added as buffers; and 1.5% benzyl alcohol added as a preservative. pH 6.6 (6.2 to 6.9). Solution may appear light yellow. Diazepam Injection is classified by the Drug Enforcement Administration as a schedule IV controlled substance. The usual recommended dose in older children and adults ranges from 2 mg to 20 mg IM or IV, depending on the indication and its severity. Diazepam Injection is injected deeply into the muscle while given through I.M. and through I.V., the solution may be injected slowly, taking at least one minute for each 5 mg (1 mL) given. This might be due to its viscosity.

Thus it is possible to produce less viscous, clear viable injectable with Diethylene glycol monoethyl ether.

By utilizing the vehicle or solvent of the present invention solvent, Diethylene glycol monoethyl ether or other alkyl derivatives, a transparent, non hazy as well as less viscous solution is obtained, which can be useful as I.V. or I.M. injections for rapid onset of action when required to provide earliest result into the patient. Since the solution is less viscous, it can be easily filtered aseptically and is easily syringable. The solution can also be used for formulation of different dosage forms like capsules, tablets, liquid oral dosage forms etc. The solution may additionally contain preservatives and buffers for maintenance of pH.

Class II: Pharmaceutical Actives or Drugs Which Have Stability Issues

As mentioned hereinbefore, there are certain pharmaceutical actives or drugs, which have inherent stability issues i.e. instability and often require complex and expensive technology for formulation of such actives into suitable stable dosage forms.

Typical example is that of pharmaceutical actives or drugs that are marketed as Lyophilized Powders or as a Dry Fill Powder and which requires reconstitution while injecting to the patient. The process of reconstitution in clinical practice is many times cumbersome due to fact that doctor and health workers are always conscious for injecting the clear liquid without leaving the trace of particles remaining as unsolubilized. Further, if the reconstituted clear liquid is kept over a shelf, commonly the drug decomposes due to instability or may increase the bioburden during storage. Further, compositions containing such pharmaceutical actives or drugs are costly to manufacture, as the processes involve lengthy and tedious technology. Due to the same, it is cost prohibitive and not beneficial to patients.

Such pharmaceutical actives or drugs can be effectively stabilized by utilization of Diethylene glycol monoethyl ether or other alkyl derivatives as a primary vehicle or solvent, to provide clear, transparent, non hazy solutions of the said pharmaceutical actives or drugs in the said vehicle or solvent, which are further less viscous and are 'ready to use' for parenteral administration through I.V., I.M. or other routes of injection or can be used for formulation of various other dosage forms of the pharmaceutical actives or drugs, such as for example, capsules, tablets, nasal sprays, gargles, dermal applications, gels, topicals, liquid oral dosage forms and other dosage forms. The solutions are easy to manufacture, do not involve lengthy and tedious manufacturing processes and are therefore, economical, viable and hence beneficial to patients. Further, when administered parenterally, the solutions are easily flowable, easily syringable, easy to inject and cause less pain at the site of the injection and are therefore, beneficial not only to the patients bit also to the doctors/physicians/nurses. Furthermore, the pharmaceutical compositions are safe and less toxic, when administered The various pharmaceutical actives or drugs, belonging to this class, to name a few are the following, which again to reiterate is non-limiting as far as the scope of the invention, is concerned.

II.1) Hydrocortisone Acetate (Steroids & Hormones)

Hydrocortisone is the main glucocorticoid secreted by the adrenal cortex. Its synthetic counterpart, Hydrocortisone acetate is a hormone used to treat local pain and swelling (inflammation) due to joint problems (e.g., arthritis, bursitis) or certain skin conditions (e.g., keloids, psoriasis). The chemical name for cortisone acetate is pregn-4-ene-3,11,20-trione, 21-(acetyloxy)-17-hydroxy and the molecular weight is 402.49. The structural formula is represented below:

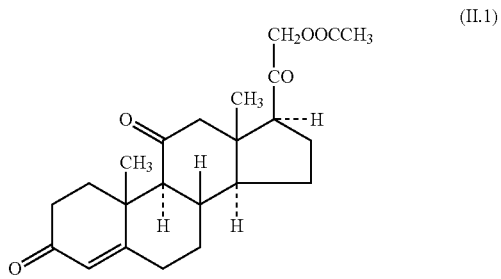

(II.1)

A white or almost white, crystalline powder; odourless, practically insoluble in water; slightly soluble in ethanol (~750 g/l). It is mostly available as tablet of strength 5 mg or 10 mg and as powder for solution in the market for I.M as well as I.V. injections as it is an insoluble molecule in water.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, gels, creams patches, liquid oral dosage forms etc. The solution may additionally contain preservatives and buffers for maintenance of pH.

II.2) 15-me-PGF$_{2\alpha}$: Carboprost (Steroids & Hormones)

15-me-PGF2alpha is as effective as natural PGF2alpha in inducing abortions during very early pregnancy. Carboprost induces contractions and can trigger abortion in early pregnancy. It also reduces postpartum bleeding. Chemically it is designated (Z)-7-[(3R,5S)-3,5-dihydroxy-2-[(E,3S)-3-hydroxy-3-methyloct-1-enyl]cyclopentyl]hept-5-enoic acid and chemical structure is given as:

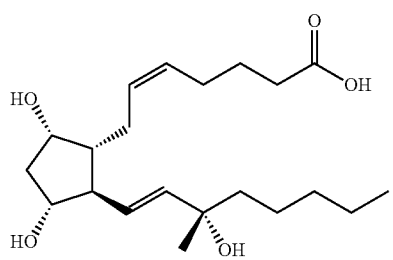

(II.2)

It is an Off-White Solid. Carboprost is a synthetic prostaglandin analogue of PGF2α (specifically, it is 15-methyl-PGF2α) with oxytocic properties.

It is available in market in form of the tromethamine salt of the (15S)-15 methyl analogue of naturally occurring prostaglandin F2α in a solution suitable for intramuscular injection. It contains sodium chloride and benzyl alcohol as solvent, which can cause hypersensitivity. Further, anaphylactic reaction, anaphylactic shock, anaphylactoid reaction and angiodema have been reported in patients. Furthermore, the use of benzyl alcohol in maximum amount in this sterile solution is associated with fatal "Gasping Syndrome" in premature patients.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, vaginal delivery like sponge bars, suppositories, liquid oral dosage forms etc. The solution may additionally contain preservatives and buffers for maintenance of pH.

II.3) Artesunate (Antimalarial)

Artesunate is an Artemisinin derivative with the antimalarial activity having molecular structure ($C_{19}H_{28}O_8$, M.W 384.4):

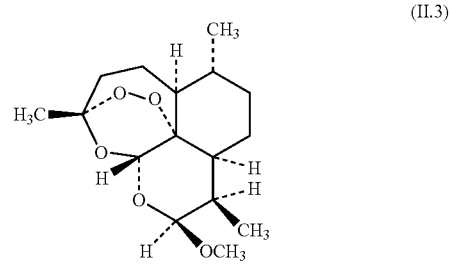 [SMILES: CO[C@H]1O[C@@H]2O[C@@]3(C)CC[C@H]4[C@H](C)CC[C@@H]([C@H]1C)[C@@]24OO3]

(II.3)

The IUPAC name of the drug is as: (3R,5aS,6R,8aS,9R,10S,-12R,12aR)-Decahydro-3,6,9-trimethyl-3,12-epoxy-12H-pyrano-[4,3-j]-1,2-benzodioxepin-10-ol hydrogen succinate. It is a white crystalline powder, slightly soluble in water.

According to WHO recommendation, Artesunate is the first option for the parenteral treatment of severe *falciparum* malaria, with the dose of 2.4 mg/kg intravenously or intramuscularly, repeated after 12 and 24 hours and then once daily thereafter.

To overcome the poor solubility of Artesunate in water a number of dosage forms and routes have been tried.

Several potent derivatives with more suitable pharmaceutical properties have been developed in which, the sodium salt of the hemmisuccinate ester i.e., sodium Artesunate which is soluble in water but have poor stability in aqueous solutions.

Artesunate is available in form of oral formulation, intramuscular formulation, intravenous formulation and suppositories. It is available as dry free powder to be reconstituted using sodium bicarbonate and water to prepare 6 mg/ml of liquid. This can cause problem of adverse reactions if not properly constituted with sodium bicarbonate as it leaves particulate matter and slight opalescence if the pharmaceutical active or drug is not highly pure.

A systemic review has suggested that intravenous Artesunate should be the drug of choice in adults with severe malaria, particularly in Asia.

Sodium Artesunate was also found to be used in control of schistosomaniasis. It is soluble in water but has poor stability in aqueous solution. The limitation of present product is its instability when composition is prepared using alkalinser like sodium bi carbonate By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient. The solution may additionally contain preservatives and buffers for maintenance of pH. The solution can also be used for formulation of other dosage forms, such as capsules.

II.4) Ergotamine Maleate (Oxytoxic)

Ergometrine maleate is a medicine which is used in bleeding after labour and inducing or enhancing labour. It is available as Ergometrine 500 micrograms/1 ml solution for injection ampoules when used in inducing labour. It is lipophilic in nature. The formulation is insoluble and often leads to coloration of liquid with the observed reduction in potency. It needs to be stabilized with antioxidants.

By utilizing the vehicle or solvent of the present invention solvent, Diethylene glycol monoethyl ether or other alkyl derivatives, a transparent, non hazy as well as less viscous solution is obtained, which can be useful as I.V. or I.M. injections for rapid onset of action when required to provide earliest result into the patient. The solution can also be used for formulation of different dosage forms like capsules, tablets, liquid oral dosage forms etc. The solution may additionally contain preservatives and buffers for maintenance of pH.

II.5, II.5$_A$) Lansoprazole and Dexlansoprazole (Proton Pump Inhibitors)

Lansoprazole (II.5) is a Proton Pump Inhibitor (PPI) in the same pharmacologic class as Omeprazole. It is available as 30 mg administered nasogastrically, effectively controls intragastric pH and is an alternative to I.V. Pantoprazole in patients who are unable to swallow solid dosage formulations. Lansoprazole is a racemate [1:1-mixture of the enantiomers Dexlansoprazole and Levolansoprazole].

Dexlansoprazole (II.5$_A$) is an enantiomerically pure active ingredient of a commercial drug as a result of the 'enantiomeric shift'. Dexlansoprazole was approved by the U.S. Food and Drug Administration (FDA) on Jan. 30, 2009. It's chemical name is (R)-(+)2-([3-methyl-4-(2,2,2-trifluoroethoxy)pyridin-2-yl]methylsulfinyl)-1H-benzo[d]imidazole with molecular structure of given as:

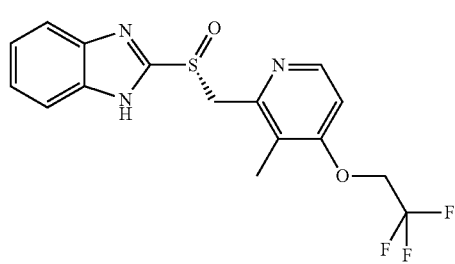

(II.5$_A$)

Dexlansoprazole is a white to nearly white crystalline powder which melts with decomposition at 140° C. Dexlansoprazole is freely soluble in dimethylformamide, methanol, dichloromethane, ethanol, and ethyl acetate; and soluble in acetonitrile; slightly soluble in ether; and very slightly soluble in water; and practically insoluble in hexane.

Dexlansoprazole is stable when exposed to light. Dexlansoprazole is more stable in neutral and alkaline conditions than acidic conditions.

According to US Patent Application No. US 2011/0028518 A1, Processes for the preparation of Dexlansoprazole, an amorphous form of Dexlansoprazole, a solid dispersion of amorphous Dexlansoprazole and a pharmaceutically acceptable carrier, and processes for their preparation is made. Dexlansoprazole is available as solid dosage form as capsule of 30 mg and 60 mg.

The solution of the sodium salt for ready-to-use administration is unstable in nature. This has been overcome by acidifying the solution to convert into a free acid form and then solubilizing the same in Diethylene glycol monoethyl ether or other alkyl derivatives to provide a transparent, non hazy solution is obtained, which can be useful as I.V. injection for rapid onset of action when required to provide earliest result into the patient. The solution may additionally contain preservatives and buffers for maintenance of pH. The solution shows good stability and can be used directly for parenteral use, obviating the need for lyophilization when metal salts are used. The solution can also be used for formulation of other dosage forms, such as capsules, tablets etc.

II.6) Fluconazole (Antifungal Agent)

Fluconazole also known as Diflucan®, is a triazole antifungal agent first described in UK Patent Application No. 2099818 (Pfizer Limited). It is used worldwide for the treatment of infections due to *Candida, Cryptococcus*, and other opportunistic yeasts or fungi. The drug is available as a tablet (50, 100, or 200 mg), as an oral suspension, and as an intravenous formulation (200 or 400 mg). When used in the treatment of invasive candidiasis, e.g., bloodstream infections, deep tissue sites, or other normally sterile site infections, Fluconazole is administered as an initial loading dose of 800 mg (oral or intravenous) followed by a daily maintenance dose of 400 mg (oral or intravenous). Fluconazole is designated chemically 2-(2,4-difluorophenyl)-1,3-bis (1H-1,2,4-triazol-1-yl)propan-2-ol with an empirical formula $C_{13}H_{12}F_2N_6O$ and molecular weight 306.3 The structural formula is given as:

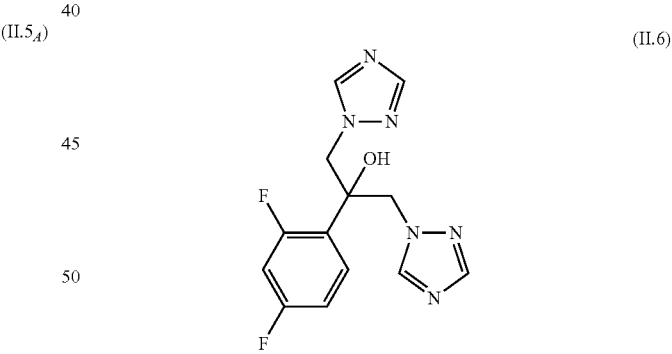

(II.6)

In a bulk powder form, it appears as a white crystalline powder, and it is very slightly soluble in water and soluble in alcohol.

Fluconazole injection, USP in 0.9% NaCl administered as intravenous infusion, is an iso osmotic solution containing 2 mg/ml of Fluconazole. It is initially administered double dose as loading dose to get earlier plasma steady state. Thus by the present art, this can be solved by making the formulation as I.V. bolus injection which may provide earlier plasma steady state concentration without increasing the loading dose. There are also chances of precipitation or cloudy solution formation in I.V. infusion as it is free from preservative can also be prevented by new formulation using suitable preservative and buffer maintaining stability of the product. Chances of air embolism or moisture may occur as I.V. infusion is packed in plastic container which might be due to plastic leaching.

By utilizing the vehicle or solvent of the present invention solvent, Diethylene glycol monoethyl ether or other alkyl derivatives, not only all the abovementioned problems are solves, but also a transparent, non hazy as well as less viscous solution is obtained, which can be useful as I.V. bolus injection or Depot I.M. injection for rapid onset of action when required to provide earliest result into the patient as well as can be used for formulation of different dosage forms like capsules, nasal sprays, gargles, gels, topical, liquid oral dosage forms, otic delivery systems etc. The solution may additionally contain preservatives and buffers for maintenance of pH.

II.7) Enalapril (ACE Inhibitor)

It is a prodrug that belongs to the angiotensin-converting enzyme (ACE) inhibitor class of medications. It is chemically designated as (2S)-1-[(2S)-2-{[(2S)-1-ethoxy-1-oxo-4-phenylbutan-2-yl]amino}propanoyl]pyrrolidine-2-carboxylic acid with chemical formula $C_{20}H_{28}N_2O_5$ and molecular structure:

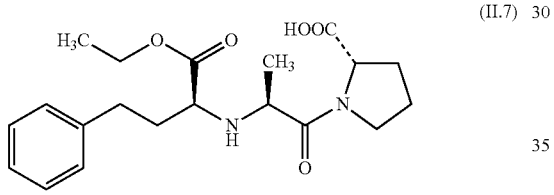

(II.7)

It is available as Enalaprilat (Enalapril Maleate) Injection, 1.25 mg per mL as I.V bolus or infusion.
HeartFailure
Adults PO Initial dosage is 2.5 mg twice daily. Usual dosage is 2.5 to 20 mg/day in 2 divided doses (max, 40 mg/day). Titrate doses upward as tolerated over a period of a few days or weeks. The max daily dose is 40 mg in divided doses.
Hypertension
Adults PO Initial dosage is 2.5 mg (patients on diuretics) to 5 mg (patients not on diuretics) per day. Titrate to desired BP control. Usual maintenance dosage is 10 to 40 mg/day in a single dose or 2 divided doses.

IV 1.25 mg over a 5-min period every 6 h. For patients at high risk of excessive hypotension, the starting dose should be 0.625 mg or less administered IV over a period of 5 min or more and preferably longer (up to 1 h).

By utilizing the vehicle or solvent of the present invention solvent, Diethylene glycol monoethyl ether or other alkyl derivatives, a transparent, non hazy as well as less viscous solution is obtained, which can be useful as I.V. bolus injection for rapid onset of action when required to provide earliest result into the patient as well as can be used for formulation of different dosage forms like capsules, tablets, liquid oral dosage forms etc. The solution may additionally contain preservatives and buffers for maintenance of pH.

II.8) Methocarbamol (CNS Depressant)

Methocarbamol is a carbamate derivative of guaifenesin, is a central nervous system (GNS) depressant with sedative and musculoskeletal relaxant properties. Methocarbamol is a white powder, sparingly soluble in water and chloroform, soluble in alcohol (only with heating) and propylene glycol, and insoluble in benzene and n-hexane. The available dose approved for human dose is Methocarbamol Tablets 500 mg, 750 mg, Methocarbamol Injection 100 mg/ml in 10 ml vials. It is a sterile, pyrogen-free solution intended for intramuscular or intravenous administration.

Each mL contains: Methocarbamol, USP 100 mg, polyethylene glycol 300, NF 0.5 mL, Water for Injection, USP q.s. The pH is adjusted, when necessary, with hydrochloric acid and/or sodium hydroxide. The chemical name of Methocarbamol is 3-(2-methoxyphenoxy)-1,2-propanediol 1-carbamate and has the empirical formula of C11H15NO5. Its molecular weight is 241.24. The structural formula is shown below:

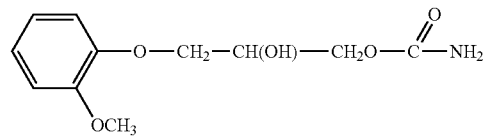

(II.8)

This injection consists of polyethylene glycol 300 as solvent. Polyethylene glycol 300 has been noted to in-crease preexisting acidosis and urea retention in humans with renal impairment. Solutions prepared for IV infusion should not be refrigerated as a precipitate may form. Because a haze or precipitate may form, all diluted intravenous solutions should be physically inspected before administration.

By utilizing the vehicle or solvent of the present invention solvent, Diethylene glycol monoethyl ether or other alkyl derivatives, not only the abovementioned stability issues are solved, but also a transparent, non hazy as well as less viscous solution is obtained, but also the nephrotoxicity associated with the prior art composition is avoided. The solutions remain clear without any precipitation even under refrigerated conditions. The solutions can be useful as I.V. injection for rapid onset of action when required to provide earliest result into the patient as well as can be used for formulation of different dosage forms like capsules, nasal sprays, gargles, gels, topical, liquid oral dosage forms, otic delivery systems etc. The solution may additionally contain preservatives and buffers for maintenance of pH.

II.9) Lignocaine (Anti-Arrhythmic Drug)

Lignocaine Injection belongs to two groups of medicines known as local anesthetics and antiarrhythmic drugs. It is injected as a dental anesthetic or as a local anesthetic for minor surgery and it is used intravenously for the treatment of ventricular arrhythmias Lignocaine is white crystalline powder, practically insoluble in water and freely soluble in ether. Lignocaine is chemically known as 2-(diethylamino)-N-(2,6-dimethylphenyl) acetamide and the molecular structure is given as:

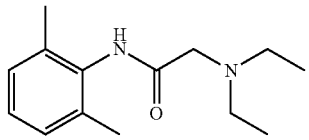

(II.9)

One of the injections available in the market contains Lignocaine Hydrochloride 1% or 2% as the active ingredient and Sodium Chloride and Water for Injections as the excipients. It does not contain a preservative. Lidocaine for infusion packed in PVC container has found to be having less content of lidocaine as result from ph dependent sorption onto the plastic.

Lidocaine is injected in form of HCl form, and by utilization the vehicle or solvent of the present invention, Diethylene glycol monoethyl ether or other alkyl derivatives, it is possible to use Lidocaine free base as such.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, nasal sprays, gargles, gels, topicals, liquid oral dosage forms etc. The solution may additionally contain preservatives and buffers for maintenance of pH.

II.10) Azithromycin (Antibiotic)

Azithromycin is an azalide, a subclass of macrolide antibiotics. Azithromycin is one of the world's best-selling antibiotics. It is derived from erythromycin, with a methyl-substituted nitrogen atom incorporated into the lactone ring, thus making the lactone ring 15-membered. This lipophilic active is chemically designated (3R,4S,5S,6R,7R,9R,11S,12R,13S,14S)-6-{[(2S,3R,4S,6R)-4-(dimethylamino)-3-hydroxy-6-methyloxan-2-yl]oxy}-14-ethyl-12,13-dihydroxy-4-{[(2R,4S,5S,6S)-5-hydroxy-4-methoxy-4,6-dimethyloxan-2-yl]oxy}-7-methoxy-3,5,7,9,11,13-hexamethyl-1-oxacyclotetradecane-2,10-dione and molecular structure is given as:

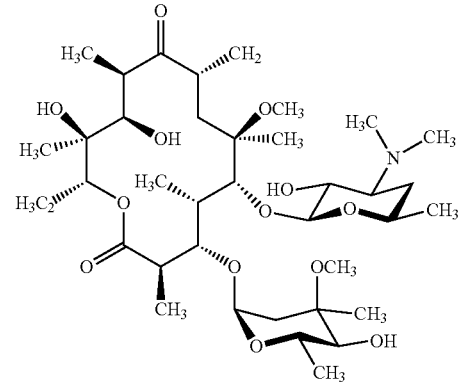

(II.10)

It is practically insoluble in water, freely soluble in methylene chloride and ethanol. It is available in Oral (capsule or suspension), intravenous, ophthalmic dosage form. For parenteral administration, Azithromycin (anhydrous) is available as sterile free dried powder (500 mg) for reconstitution with sterile water for injection.

By utilizing the vehicle or solvent of the present invention solvent, Diethylene glycol monoethyl ether or other alkyl derivatives, a transparent, non hazy as well as less viscous solution is obtained, which can be useful as I.V. or I.M. injections for rapid onset of action when required to provide earliest result into the patient as well as can be used for formulation of different dosage forms like capsules, tablets, liquid oral dosage forms etc. The solution may additionally contain preservatives and buffers for maintenance of pH.

II.11) Cardiac Glycoside: Digoxin (Anti-Arrhythmic Drug)

Digoxin is a purified cardiac glycoside extracted from the foxglove plant, *Digitalis lanata*. Its corresponding aglycone is digoxigenin, and its acetyl derivative is acetyldigoxin. Digoxin is widely used in the treatment of various heart conditions, namely atrial fibrillation, atrial flutter and sometimes heart failure that cannot be controlled by other medication. It is available as tablet form and also available as a 0.05 mg/ml oral solution and 0.25 mg/ml or 0.5 mg/ml injectable solution.

Digoxin is described chemically as (3β,5β,12β)-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]-12,14-dihydroxy-card-20(22)-enolide. Its molecular formula is $C_{41}H_{64}O_{14}$, its molecular weight is 780.95, and its structural formula is:

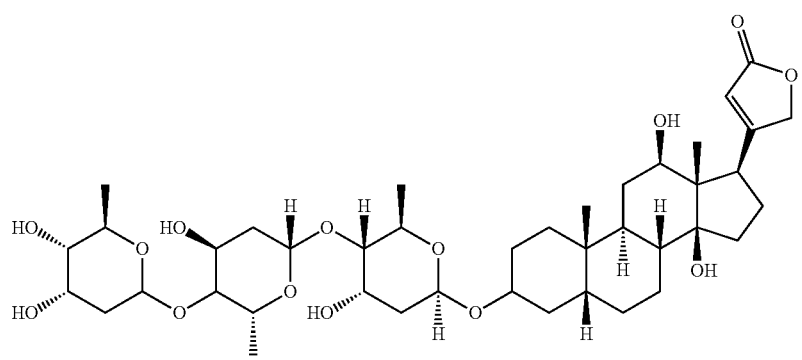

(II.11)

It is practically insoluble in water, freely soluble in equal amount of methylene chloride and methanol, slightly soluble in ethanol.

I.V. therapy may be better tolerated (less nausea); Digoxin has a very long distribution half-life into the cardiac tissue, which will delay its onset of action by a number of hours. The half-life is about 36 hours; digoxin is given once daily, usually in 125-μg or 250-μg doses. Digoxin is usually given by mouth, but can also be given by I.V. injection in urgent situations. It is available as a sterile solution of digoxin for intravenous or intramuscular injection. The vehicle contains 40% propylene glycol and 10% alcohol. The injection is buffered to a pH of 6.8 to 7.2 with 0.17% dibasic sodium phosphate and 0.08% anhydrous citric acid. Each 2-mL ampoule contains 500 meg (0.5 mg) Digoxin (250 meg [0.25 mg] per mL). Dilution is not required.

Intramuscular injection of Digoxin is extremely painful and offers no advantages unless other routes of administration are contraindicated. Thus this pain can be prevented by preparing parenteral for I.M/I.V by using the present selected solvent which will also increase onset of action as it will also act as permeation enhancer.

By utilizing the vehicle or solvent of the present invention solvent, Diethylene glycol monoethyl ether or other alkyl derivatives, not only a transparent, non hazy as well as less viscous solution is obtained, which can be useful as I.V. or I.M. injections for rapid onset of action when required to provide earliest result into the patient, but also the pain at the site of injection is prevented. The solution can also be used for formulation of different dosage forms like capsules, tablets, nasal sprays, gargles, gels, topicals, liquid oral dosage forms etc. The solution may additionally contain preservatives and buffers for maintenance of pH.

II.12) Dicyclomine (Gastrointestinal)

Dicyclomine is used to treat intestinal hypermotility and the symptoms of irritable bowel syndrome

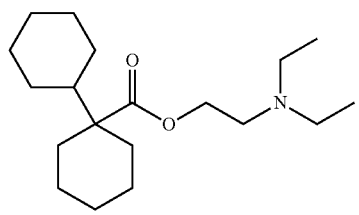

(II.12)

Dicyclomine hydrochloride occurs as a fine, white, crystalline, practically odorless powder with a bitter taste. It is soluble in water, freely soluble in alcohol and chloroform, and very slightly soluble in ether.

The solubility of dicyclomine in the present invention vehicle is observed in range of 1 to 20 mg/ml.

By utilizing the vehicle or solvent of the present invention solvent, Diethylene glycol monoethyl ether or other alkyl derivatives, not only a transparent, non hazy as well as less viscous solution is obtained, which can be useful as I.V. injections for rapid onset of action when required to provide earliest result into the patient, but also the pain at the site of injection is prevented. The solution can also be used for formulation of different dosage forms like capsules, tablets, liquid oral dosage forms etc. The solution may additionally contain preservatives and buffers for maintenance of pH. It can be also prepared and administered in combination with other drugs. Similarly, different drug combination of drug like Diclofenac with Dicyclomine can also be prepared in solution form for therapeutic use in required dose.

II.13) Paracetamol/Acetaminophen (Analgesic & Antipyrretic)

Paracetamol or Acetaminophen has analgesic and antipyretic properties and weak anti-inflammatory activity and is used in the symptomatic management of moderate pain and fever. It belongs to class 3 BCS drug. The structural formula of Paracetamol is given as:

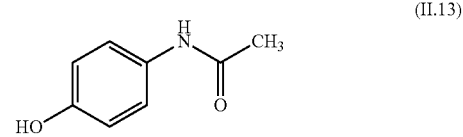

(II.13)

It is a white, crystalline powder. Acetaminophen is a synthetic, non-opiate, centrally acting analgesic derived from p-aminophenol. The full chemical name is N-acetyl-p-aminophenol. It is stable at a pH between 4 and 7 at 25° C. It is available in injection as i.v bolus, i.v infusion, tablet, syrup, suppository and as oral suspension.

According to U.S. Patent Application No. 2004/0247627 A1, this invention refers to ready-to-use highly stable paracetamol injectable solutions, prepared by mixing paracetamol, water, propylene glycol, and a citrate buffer (pH 4.5 to 6.5), and by heating said solution under preset conditions. This injection consists of about 20% of propylene glycol only co-solvent that shows the high viscous nature of the injection which may be painful for use. At long time period storage, there is formation of paracetamol polymers or benzoquinoneimines providing color to the solution which is unsafe for use due to decomposition.

In U.S. Application No. 20090215903, aqueous solution of paracetamol is prepared for its use by perfusion with a pH between 4.5 to 6.0. In this formulation, byproducts of sulfate, gluconate or fufural ions can be found in solution even in presence of antioxidant into the same formulation.

There is reported death of neonate due to use of preservative like benzyl alcohol used in Paracetamol injection.

Thus above problems can be obviated by using Diethylene glycol monoethyl ether to provide an alternate stable injection preventing the development of unwanted color of solution over time and preventing formation of any of byproducts as cited above.

It is possible to add other excipients while compounding in combination with other vehicles which are currently used in Paracetamol as infusion liquid to prevent various problems of high viscosity, stability, and impurity related matters.

By utilizing the vehicle or solvent of the present invention solvent, Diethylene glycol monoethyl ether or other alkyl derivatives, not only a transparent, non hazy as well as less viscous solution is obtained, which can be useful as I.V. and I.M. injections for rapid onset of action when required to provide earliest result into the patient, but also the pain at the site of injection is prevented. The solution can also be used for formulation of different dosage forms like capsules, tablets, liquid oral dosage forms, oral suspensions, suppositories, buccal delivery systems, sprays etc. The solution may additionally contain preservatives and buffers for maintenance of pH. It can be also prepared and administered in combination with other drugs.

The concentration range and fill volumes can be 50 mg/0.5 ml, 100 mg/0.5 ml, 200 mg/ml, 400 mg/2 ml, 600 mg/3 ml, 1000 mg/5 ml filled as ampoules similarly, vials of 5 ml containing 200 mg/ml, 10 ml vial containing 100 mg/ml, 20 ml vial containing 50 mg/ml, 50 ml vial containing 20 mg/ml, 100 ml vial containing 10 mg/ml dose of Paracetamol may be filled for convenient use of the medical practitioner. This ampoule and vial form can offer flexibility to medical professional for use as this can provide flexibility of dose as per patients need. These forms can be diluted online with saline solution and can be administered as a drip. A low dose of 50 mg/0.5 ml can be useful for use in neonates for reduction and monitoring of temperature in case of fever. Thus, this invention solubilizer can provide oil free painless low viscosity injectables of Paracetamol filled in ampoules, vials, blow fill ampoules, Prefilled Syringes for Intravenous and Intramuscular use for the use in Neonatal, Pediatric and Adult Patients.

II.14) Pentazocine (Analgesic Agent)

Pentazocine is a synthetically prepared prototypical mixed agonist-antagonist narcotic (opioid analgesic) drug of the benzomorphan class of opioids used to treat moderate to moderately severe pain. Pentazocine is sparingly soluble in water. Its salt form Pentazocine HCl as well as Pentazocine Lactate are also sparingly soluble in water. While lactate salt is prepared as injectable according USP and BP. Chemically, Pentazocine lactate is 1,2,3,4,5,6-hexahydro-6,11-dimethyl-3-(3-methyl-2-butenyl)-2,6-methano-3-benzazocin-8-ol lactate, a white, crystalline substance soluble in acidic aqueous solutions. The molecular structure of Pentazocine is

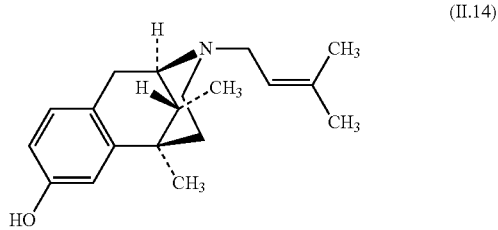 [SMILES: CC(C)=CCN1CC[C@@]2(C)c3cc(O)ccc3C[C@@H]1[C@@H]2C]

(II.14)

It is white powder practically insoluble in water; freely soluble in methylene chloride and soluble in ethanol (almost 96%).

The recommended single parenteral dose is 30 mg by intramuscular, subcutaneous, or intravenous route. This may be repeated every 3 to 4 hours. Total daily dosage should not exceed 360 mg. A single, intramuscular 30 mg dose has been most commonly administered. Severe injection site necrosis and sepsis has occurred with multiple injection of Pentazocine lactate.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, gels, patches, liquid oral dosage forms etc. The solution may additionally contain preservatives and buffers for maintenance of pH.

II.15, II.15$_A$) Fentanyl & Fenatyl Citrate (Analgesic Agents)

Fentanyl is a potent, synthetic narcotic analgesic with a rapid onset and short duration of action. It is a strong agonist at the μ-opioid receptors. Fentanyl is approximately 100 times more potent than morphine. Intravenous fentanyl is extensively used for anesthesia and analgesia, most often in operating rooms and intensive care units. It is chemically designated as N-(1-(2-phenylethyl)-4-piperidinyl)-N-phe-nylpropanamide and molecular structure is given as:

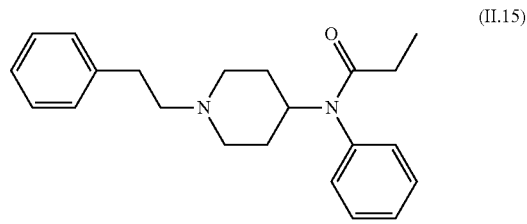 [SMILES: CCC(=O)N(c1ccccc1)C1CCN(CCc2ccccc2)CC1]

(II.15)

Fentanyl Citrate Injection, USP is a sterile, nonpyrogenic solution of Fentanyl citrate in water for injection. Fentanyl Citrate is a potent narcotic analgesic which is administered only by the intravenous or intramuscular routes of injection. Each milliliter contains fentanyl (as the citrate) 50 mcg (0.05 mg). It may contain sodium hydroxide and/or hydrochloric acid for pH adjustment. pH 4.7 (4.0 to 7.5). It is intended only for use as a single-dose injection.

Fentanyl Citrate, a white powder which is sparingly soluble in water, is chemically designated N-(1-phenethyl-4-piperidyl) propionanilide citrate (1:1). The molecular formula is $C_{22}H_{28}N_2O.C_6H_8O_7$ and the molecular weight is 528.60. Fentanyl Citrate has the following structural formula:

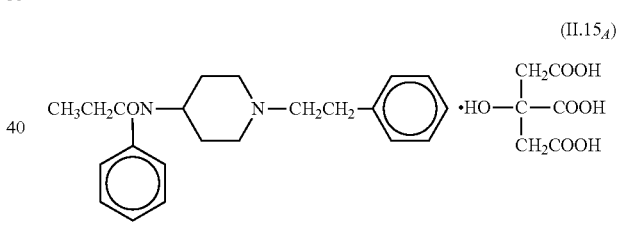

(II.15$_A$)

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, gels, patches, liquid oral dosage forms etc. The solution may additionally contain preservatives and buffers for maintenance of pH.

II.16) Prostaglandin E1/Alprostadil (Steroids & Hormones)

Alprostadil as the naturally occurring form of prostaglandin E1 (PGE1) and is designated chemically as (11α,13E,15S)-11,15-dihydroxy-9-oxoprost-13-en-1-oic acid. The molecular weight is 354.49.

Alprostadil is a white to off-white crystalline powder with a melting point between 115° and 116° C. Its solubility at 35° C. is 8000 micrograms per 100 milliliter double distilled water.

The structural formula of alprostadil is represented as:

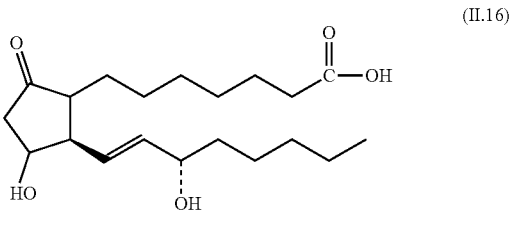 [SMILES: CCCCC[C@H](O)/C=C/[C@H]1C(O)CC(=O)C1CCCCCCC(=O)O]

(II.16)

It is available in market as a sterile freeze-dried powder for intracavernosal use in four sizes: 5, 10, 20 and 40 micro-grams per vial—When reconstituted as directed with 1 milliliter of bacteriostatic water for injection or sterile water, both preserved with benzyl alcohol, gives 1.13 milliliters of reconstituted solution. Each milliliter of this injection contains 5.4, 10.5, 20.5 or 41.1 micrograms of Alprostadil depending on vial strength, lactose, sodium citrate and benzyl alcohol. The deliverable amount of Alprostadil is 5, 10, 20 or 40 micrograms per milliliter because approximately 0.4 microgram for the 5 microgram strength, 0.5 microgram for the 10 and 20 microgram strengths and 1.1 microgram for the 40 microgram strength is lost due to adsorption to the vial and syringe. When necessary, the pH of Alprostadil for injection is adjusted with hydrochloric acid and/or sodium hydroxide before lyophilization.

By utilizing the vehicle or solvent of the present invention solvent, Diethylene glycol monoethyl ether or other alkyl derivatives, a transparent, non hazy solution is obtained, which can be useful as I.M as well as I.V. injection for rapid onset of action when required to provide earliest result into the patient. The solution may additionally contain preservatives and buffers for maintenance of pH. The solution can be filled in FFS or glass disposable syringes as well as there would be no loss of drug from the vial and syringe.

Proton Pump Inhibitors (PPIs)

Generally all the PPIs are manufactured as metal salts, the reason being for formation of suitable crystalline forms, ready to be formulated as lyophilized metal salts or by complexing with suitable stabilizing agents to avoid their degradation. The present inventors have found that if the acid form of the PPIs is isolated during manufacture the same acid form can be solubilized in Diethylene glycol monoethyl ether or other alkyl derivatives, to yield a clear and stable solution, which can be used directly as injectables or used for preparation of other dosage forms, suitable for oral administration.

The following examples illustrate the above mentioned findings, which should be construed as non-limiting and construed as also applicable for other drugs or compounds belonging to the same or different class, having similar stability limitations.

II.17) Omeprazole (Proton Pump Inhibitor)

Omeprazole is one of the most widely prescribed drugs internationally as Proton pump inhibitor in the treatment of dyspepsia, peptic ulcer disease (PUD), gastro esophageal reflux disease (GORD/GERD), laryngopharyngeal reflux (LPR) and Zollinger-Ellison syndrome. The chemical name of this drug is (RS)-2-([3-methyl-4-(2,2,2-trifluoroethoxy) pyridin-2-yl]methylsulfinyl)-1H-benzo[d]imidazole and molecular structure is as:

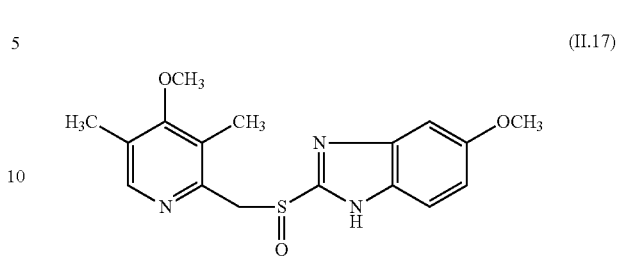

(II.17)

Omeprazole is a white to off-white crystalline powder that melts with decomposition at about 155° C. It is a weak base, freely soluble in ethanol and methanol, and slightly soluble in acetone and isopropanol and very slightly soluble in water. The stability of Omeprazole is a function of pH; it is rapidly degraded in acid media, but has acceptable stability under alkaline conditions.

It is available for use in injectable form (I.V.) in Europe, but not in the U.S. The injection pack is a combination pack consisting of a vial and a separate ampoule of reconstituting solution. Each 10 ml clear glass vial contains a white to off-white lyophilized powder consisting of Omeprazole sodium 42.6 mg equivalent to 40 mg of Omeprazole.

According to Patent No. KP 1019930009791, an Omeprazole injection is made by (a) dissolving Omeprazole or non-oral administrating omeprazole salt and other additives into distilled water; (b) adjusting pH 8.5-9.5 with N-methylglucamine or such buffer solution as 2-amino-2-hydroxymethyl-1,3-propanediol or the mixture of N-methylglucamine and potassium hydrogen phosphate in order to make it stable.

By utilizing the vehicle or solvent of the present invention solvent, Diethylene glycol monoethyl ether or other alkyl derivatives, a transparent, non hazy solution is obtained, which can be useful as I.V. injection for rapid onset of action when required to provide earliest result into the patient. The solution may additionally contain preservatives and buffers for maintenance of pH. The solution shows good stability and can be used directly for parenteral use, obviating the need for lyophilization when metal salts are used. The solution can also be used for formulation of other dosage forms, such as capsules, tablets etc.

II.18) Rabeprazole (Proton Pump Inhibitor)

Rabeprazole is an anti-ulcer agent used for Short-term treatment in healing and symptomatic relief of duodenal ulcers and erosive or ulcerative gastroesophageal reflux disease (GERD). The chemical name of this lipophilic active is (RS)-2-([4-(3-methoxypropoxy)-3-methylpyridin-2-yl]methylsulfinyl)-1H-benzo[d]imidazole with the following complex molecular structure that makes it insoluble in water:

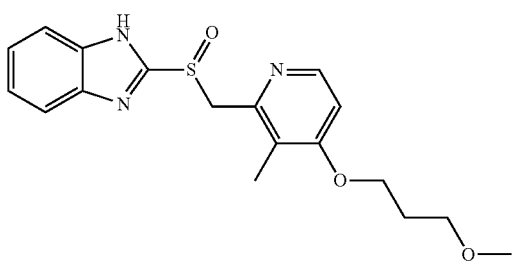

(II.18)

In market, it is mostly available in enteric coated tablet dosage form in 20 mg and 10 mg dose. The bioavailability is only 51% which can be increased by preparing its parenteral preparation in I.V formulation. While available I.V preparation consist of Rabeprazole sodium in freeze dried powder for reconstitute in 5 ml of sterile water. This available product may be time consuming and costly by process. So it may be possible to make easier I.V. parenteral preparation by dissolving this salt in our selected solvent Di ethylene glycol mono ethyl ether and alike solvents with preferable preservatives and tris buffers to maintain its pH near alkaline nature to maintain its stability in solution.

By utilizing the vehicle or solvent of the present invention solvent, Diethylene glycol monoethyl ether or other alkyl derivatives, a transparent, non hazy solution is obtained, which can be useful as I.V. injection for rapid onset of action when required to provide earliest result into the patient. The solution may additionally contain preservatives and buffers for maintenance of pH. The solution shows good stability and can be used directly for parenteral use, obviating the need for lyophilization when metal salts are used. The solution can also be used for formulation of other dosage forms, such as capsules—soft and hard gelating types, tablets, ready to use drops, syrups, buccal delivery systems, oral liquids etc.

II.19) Pantoprazole (Proton Pump Inhibitor)

Pantoprazole is a PPI with the actions and uses similar to those of Omeprazole.

It is given as the sodium salt but doses a expressed in terms of base. The molecular name of this drug is $C_{16}H_{14}F_2N_3NaO_4S$ with the molecular structure is as:

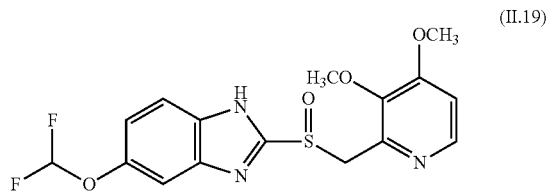 [SMILES: COc1ccnc(CS(=O)c2nc3cc(OC(F)F)ccc3[nH]2)c1OC]

(II.19)

Pantoprazole sodium 11.28 mg is equivalent to about 10 mg of Pantoprazole. It is given intravenously as the sodium salt, over 2 to 15 minutes, either as a slow injection or a short term infusion. For peptic ulceration or gastro-esophageal reflux disease, the recommended dose is 40 mg daily. This sodium salt form is available in form of lyophilized parenteral which is mostly off white in color.

The solution of the sodium salt for ready-to-use administration is unstable in nature. This has been overcome by acidifying the solution to convert into a free acid form and then solubilizing the same in Diethylene glycol monoethyl ether or other alkyl derivatives to provide a transparent, non hazy solution is obtained, which can be useful as I.V. injection for rapid onset of action when required to provide earliest result into the patient. The solution may additionally contain preservatives and buffers for maintenance of pH. The solution shows good stability and can be used directly for parenteral use, obviating the need for lyophilization when metal salts are used. The solution can also be used for formulation of other dosage forms, such as capsules capsules—soft and hard gelating types, tablets, ready to use drops, syrups, buccal delivery systems, oral liquids etc.

II.20) Lornoxicam (Antirhuematic Actives for Musculo Skeletal System—Oxicams)

It is a Non-steroidal Anti-inflammatory Drug (NSAID of the Oxicam) class with analgesic (pain relieving), anti-inflammatory and antipyretic (fever reducing) properties. It is available in oral and parenteral formulations. It is chemically designated as (3E)-6-chloro-3-[hydroxy(pyridin-2-ylamino)methylene]-2-methyl-2,3-dihydro-4H-thieno[2,3-e][1,2]thiazin-4-one 1,1-dioxide with molecular structure as

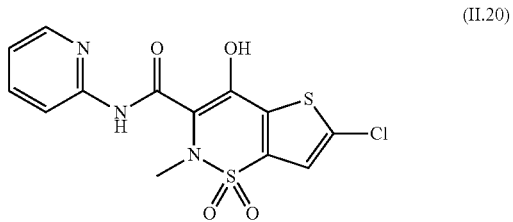 [SMILES: CN1C(C(=O)Nc2ccccn2)=C(O)c2sc(Cl)cc2S1(=O)=O]

(II.20)

It is slight yellow crystalline powder hardly soluble in water, slightly soluble in chloroform and methanol, very lightly soluble in methanol and Acetonitrile, soluble in DMSO.

PCT Application No. WO/1996/041646, discloses a pharmaceutical composition in the form of an aqueous solution or in the form of a product for reconstitution as an aqueous solution, for parenteral administration or ophthalmic administration, comprising lomoxicam or a pharmaceutically acceptable salt thereof and a cyclodextrin selected from the group consisting of hydroxypropylated or sulphoalkylated derivatives of alpha, beta or gamma cyclodextrin.

In Chinese Patent No. CN 101327193 A, the invention relates to Lornoxicam freeze-dried powder injection and a preparation method thereof. The freeze-dried powder injection comprises lornoxicam, mannite, tromethamine, EDTA and pH regulator.

The marketed one vial compositions contains 8 mg Lornoxicam, which provides 4 mg Lornoxicam per ml when reconstituted as recommended in water. It contains Mannitol, trometamol, disodium edentate. The manufacturing of the powder filling is costly process and reconstitution is tedious and not friendly process to the doctors.

Freeze dried product needs special care of storage for the stability of the product for reconstitute into parenteral solution. While inclusion of Lornoxicam into cyclodextrin can be costly in sense of process and may be nephrotoxic.

By utilizing the vehicle or solvent of the present invention solvent, Diethylene glycol monoethyl ether or other alkyl derivatives, not only all the abovementioned problems are solves, but also a transparent, non hazy as well as less viscous solution is obtained, which can be useful as I.V. bolus injection or Depot I.M. injection for rapid onset of action when required to provide earliest result into the patient as well as can be used for formulation of different dosage forms like capsules, nasal sprays, gargles, gels, topical, liquid oral dosage forms, otic delivery systems etc. The solution may additionally contain preservatives and buffers for maintenance of pH.

II.21) Etoposide (Anticancer Agent)

Etoposide is a semisynthetic derivative of podophyllotoxin used in the treatment of certain neoplastic diseases. It is 4'-demethylepipodophyllotoxin 9-[4,6-0-(R)-ethylidene-β-D-glucopyranoside]. It is very soluble in methanol and chloroform, slightly soluble in ethanol and sparingly soluble in water and ether. It is made more miscible with water by means of organic solvents. It has a molecular weight of 588.58 and a molecular formula of $C_{29}H_{32}O_{13}$ and the molecular structure is given as:

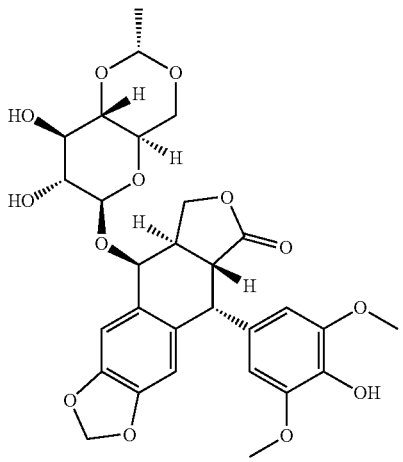

(II.21)

Etoposide Injection USP is available for intravenous use as 20 mg/mL solution in 100 mg (5 mL), 500 mg (25 mL), and 1 g (50 mL) sterile, multiple-dose vials. The pH of the clear, nearly colorless to yellow liquid is 3 to 4. Each mL contains 20 mg Etoposide USP, 2 mg citric acid, 30 mg benzyl alcohol, and 80 mg modified polysorbate 80/tween 80, 650 mg polyethylene glycol 300, and 30.5 percent (v/v) alcohol. Etoposide Injection available in market is been diluted prior to use with either 5% Dextrose Injection, or 0.9% Sodium Chloride Injection, to give a final concentration of 0.2 to 0.4 mg/mL. If solutions are prepared at concentrations above 0.4 mg/mL, precipitation may occur. The injection is viscous and gives pain at the site of injection. Further, it uses a cocktail of excipients, like PEG and Polysorbate 80, which are toxic.

By utilizing the vehicle or solvent of the present invention solvent, Diethylene glycol monoethyl ether or other alkyl derivatives, not only a transparent, non hazy as well as less viscous solution is obtained, which can be useful as I.V. injections for rapid onset of action when required to provide earliest result into the patient, but also does not result in pain at the site of injection. The solution can also be used for formulation of different dosage forms like capsules, tablets, liquid oral dosage forms etc. The solution may additionally contain preservatives and buffers for maintenance of pH.

II.22) Docetaxel (Anticancer Agent)

It is a semi-synthetic analogue of Paclitaxel (Taxol), an extract from the bark of the rare Pacific yew tree *Taxus brevifolia*. Docetaxel is a clinically well-established anti-mitotic chemotherapy medication. It is used mainly for the treatment of breast, ovarian, prostate, and non-small cell lung cancer.

Docetaxel is chemically designated as 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl) amino]-2-hydroxy-3-phenylpropanoate} and the molecular structure is given as:

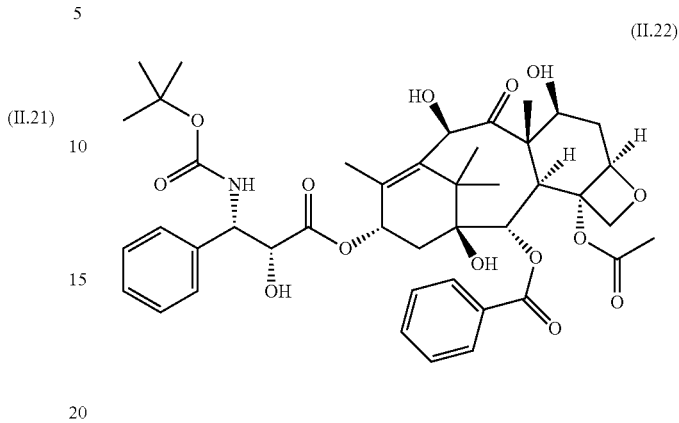

(II.22)

According to a 2005 article in the Journal, Drugs, Docetaxel is administered as a one-hour infusion every three weeks generally over a ten cycle course and Docetaxel is considered as more effective than Doxorubicin, Paclitaxel and Fluorouracil as a cytotoxic anti microtubule agent.

Docetaxel is a white to almost-white powder with an empirical formula of $C_{43}H_{53}NO_{14} \cdot 3H_2O$ and a molecular weight of 861.9. It is highly lipophilic and practically insoluble in water.

Docetaxel is a white powder and is the active ingredient available in 20 mg and 80 mg Taxotere single-dose vials of concentrated anhydrous docetaxel in polysorbate 80. It is pale yellow to brownish-yellow solution at 20 mg/mL concentration. Each mL contains 20 mg docetaxel (anhydrous) in 0.54 grams polysorbate 80 and 0.395 grams dehydrated alcohol solution.

Another formulation made available consist of one vial preparation in which all the composition of the above remains the same except the quantity of ethanol is decreased.

From the above marketed formulations, it is seen that it still contains high concentration of alcohol and Polysorbate 80. To obviate the use of above toxic vehicles, a solution prepared using Diethylene glycol monoethyl ether can be prepared in the suitable concentration and may be diluted to the desired concentration while performing infusion therapy.

By utilizing the vehicle or solvent of the present invention solvent, Diethylene glycol monoethyl ether or other alkyl derivatives, a transparent, non hazy as well as less viscous solution is obtained, which can be useful as I.V. injections for rapid onset of action when required to provide earliest result into the patient. The solution can also be used for formulation of different dosage forms like capsules, tablets, liquid oral dosage forms etc. The solution may additionally contain preservatives and buffers for maintenance of pH.

II.23) Leuprolide (Anticancer Agent)

Leuprorelin or Leuprolide acetate is a GnRH analog. Leuprolide acts as an agonist at pituitary GnRH receptors. Leuprolide may be used in the treatment of hormone-responsive cancers such as prostate cancer or breast cancer, estrogen-dependent conditions, to treat precocious puberty, and to control ovarian stimulation in In Vitro Fertilization (IVF).

The chemical name is 5oxo-L-prolyl-L-histidyl-L-tryptophyl-L-seryl-L-tyrosyl-D-leucyl-L-leucyl-L-arginyl-N-ethyl-L-prolinamide acetate (salt) and the molecular structure is given as:

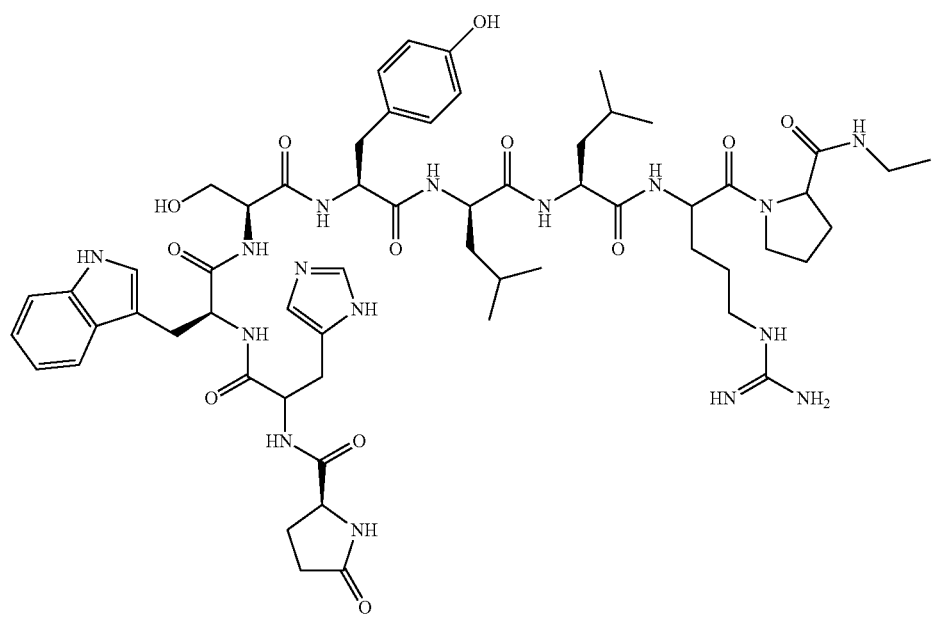

(II.23)

It is available as a slow-release implant or subcutaneous/intramuscular injection. It is available in a prefilled dual-chamber syringe containing sterile lyophilized microspheres which, when mixed with diluent, become a suspension intended as a monthly intramuscular injection. Leuprolide acetate is a synthetic nonapeptide analog of naturally occurring gonadotropin-releasing hormone (GnRH or LH-RH).

This suspension may have stability issue concern with viscousness that may painful too.

By utilizing the vehicle or solvent of the present invention solvent, Diethylene glycol monoethyl ether or other alkyl derivatives, a transparent, non hazy as well as less viscous solution is obtained, which can be useful as I.V. or I.M. injections for rapid onset of action when required to provide earliest result into the patient. The solution can also be used for formulation of different dosage forms like capsules, tablets, liquid oral dosage forms etc. The solution may additionally contain preservatives and buffers for maintenance of pH.

II.24) Clarithromycin (Antibiotic)

It is effective against a broad spectrum of gram-positive and gram-negative bacteria. It is used to treat respiratory tract infections and soft tissue infections. It is used to treat duodenal ulcer associated with *Helicobacter pylori* infections in combination with omeprazole. One common feature of clarithromycin appears to be the stability against acids. It is absorbed and diffused easily into tissues and phagocytes without being protected from gastric acids. It is more effective against certain gram-negative bacteria, such as *Legionella pneumophilae* than Erythromycin.

This lipophilic active is chemically designated as (3R,4S,5S,6R,7R,9R,11R,12R,13S,14R)-4-[(2,6-Dideoxy-3-C-methyl-3-O-methyl-a-L-ribo-hexopyranosyl)oxy]-14-ethyl-12,13-dihydroxy-7-methoxy-3,5,7,9,11,13-hexamethyl-6-[[3,4,6-trideoxy-3-(dimethylamino)-b-D-xylo-hexopyranosyl]oxy]oxacyclotetradecane-2,10-dione(6-O-methylerythromycin A) and molecular structure is given as:

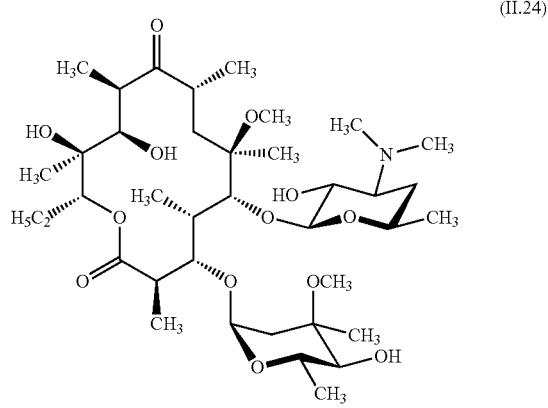

(II.24)

Clarithromycin is a white to off-white crystalline powder; insoluble in water; soluble in acetone, slightly soluble in alcohol and acetonitrile; administered orally.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution may additionally contain preservatives and buffers for maintenance of pH.

II.25) Voriconazole (Antifungal Agent)

Voriconazole is a triazole antifungal medication that is generally used to treat serious, invasive fungal infections and if has become the new standard of care in the treatment of invasive aspergillosis, which may occur in immune-compromised patients, including allogeneic BMT, other hematologic cancers, and solid organ transplants. The systemic name of this drug is (2R,3S)-2-(2,4-difluorophenyl)-3-(5-fluoropyrimidin-4-yl)-1-(1H-1,2,4-triazol-1-yl)butan-2-ol with the molecular structure as:

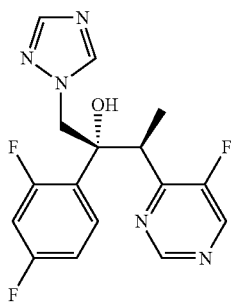

(II.25)

It is available as a lyophilized powder for solution for intravenous infusion, film-coated tablets for oral administration, and as a powder for oral suspension. It is available as I.V. parenteral containing a white lyophilized powder containing nominally 200 mg voriconazole and sulfobutyl ether beta-cyclodextrin sodium in a 30 mL Type 1 clear glass vial.

The beta-cyclodextrin derivatives are nephrotoxic. Thus there is a limitation of present formulation. The formulation requires costly technique of manufacturing for lyophilization and requires reconstitution. The practice to reconstitute is cumbersome to the health professional. Further stability of solution is an issue.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

II.26) Neuromuscular Blocking Agents

Various Neuromuscular agents like Vecuronium, Atracurium isomers like Cisatracurium, Doxacurium, Tubocurarine, Pipecuronium, Rocuronium, Pancuronium etc. are available in market as lyophilized product as well as ready to use injectables.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

II.27) Ibuprofen (Anti-Inflammatory)

Presently Ibuprofen injections are available as drug with arginine comlexation as 200 mg/2 ml and 400 mg/4 ml The use of arginine is very high and the drug to arginine ratio is 1:1 which adds up the cost and close monitoring of manufacturing and its therapeutic effect.

Often the muscular phlebiits is observed after its use in the clinical trials.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topical, liquid oral dosage forms etc. The injections can be prepared in the desired strengths of 200 mg and 400 mg/ml. The solution may additionally contain preservatives and buffers for maintenance of pH.

Class III: Pharmaceutical Actives of Drugs Which are Available in the Form of Suspensions and are Very Difficult to be Solubilized into a Solution Form As mentioned hereinbefore, there are certain pharmaceutical actives or drugs, which are very difficult to solubilize into a solution form and have further stability issues i.e. instability and often require complex and expensive technology for formulation of such actives into suitable stable dosage forms, especially suspension forms.

Drugs that are present in oily or aqueous liquid form have solubility problems as well as various physical as well as chemical issues when incorporated in the formulation. They are also prepared using difficult manufacturing process. Such formulations are found to cake on standing in addition to phase separation which is common problems of suspension form. Stabilization of the emulsion formulation is a consistent problem and challenge to pharmaceutical scientists.

Currently available formulations in the market are associated with multitude of problems as cited below.

1) Costly technology:

The process involved in their preparation uses complex technologies to maintain it as suspension form. Hence, there are difficulties in their manufacturing and maintaining of consistency of the formulation.

The suspensions during the manufacturing requires process controls and checks to maintain uniformity of the particle size in the preparations and for their stability for the intended forms during the end use.

2) Manufacturing problems: Difficulties in stabilizing the suspensions.

The suspension should remain homogenous on storage. The suspension often causes agglomeration and thus becomes nonhomogenious.

The emulsions are not user friendly to the Doctors. Health professionals always prefer clear solution for the parenteral administration.

Such pharmaceutical actives or drugs can be effectively stabilized by utilization of Diethylene glycol monoethyl ether or other alkyl derivatives as a primary vehicle or solvent, to provide clear, transparent, non hazy solutions of the said pharmaceutical actives or drugs in the said vehicle or solvent, which are further less viscous and are 'ready to use' for parenteral administration through I.V., I.M. or other routes of injection or can be used for formulation of various other dosage forms of the pharmaceutical actives or drugs, such as for example, capsules, tablets, nasal sprays, gargles, dermal applications, gels, topicals, liquid oral dosage forms and other dosage forms. The solutions are easy to manufacture, do not involve lengthy and tedious manufacturing processes and are therefore, economical, viable and hence beneficial to patients. Further, when administered parenterally, the solutions are easily flowable, easily syringable, easy to inject and cause less pain at the site of the injection and are therefore, beneficial not only to the patients bit also to the doctors/physicians/nurses. Furthermore, the pharmaceutical compositions are safe and less toxic, when administered The various pharmaceutical actives or drugs, belonging to this class, to name a few are the following, which again to reiterate is non-limiting as far as the scope of the invention, is concerned.

III.1, III.1$_A$) Prednisolone & Prednisolone Acetate (Steroids & Hormones)

Prednisolone is a synthetic glucocorticoid, a derivative of cortisol. It is used to treat a variety of inflammatory and auto-immune conditions. It is the active metabolite of the drug prednisone.

It is a white, hygroscopic, crystalline powder and it shows polymorphism. It is very slightly soluble in water, soluble in alcohol and sparingly soluble in acetone. The IUPAC name of this drug is (11β)-11,17,21-trihydroxypregna-1,4-diene-3,20-dione and the chemical structure is given as:

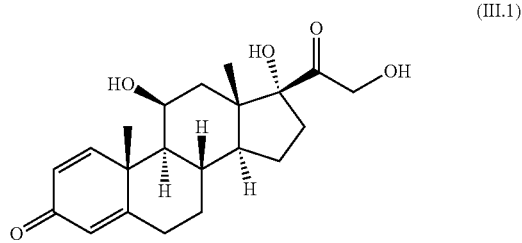

(III.1)

It is available in various salt forms as Prednisolone acetate, Prednisolone sodium succinate, Prednisolone disodium phosphate, Prednisolone Tebutate. In market, Prednisolone acetate is available as an injectable suspension.

Prednisolone acetate is a white crystalline powder. It is practically insoluble in water and slightly soluble in alcohol. The chemical name of this salt is 11β,17,21-Trihydroxypregna-1,4-diene-3,20-dione 21-acetate and the chemical structure is given as:

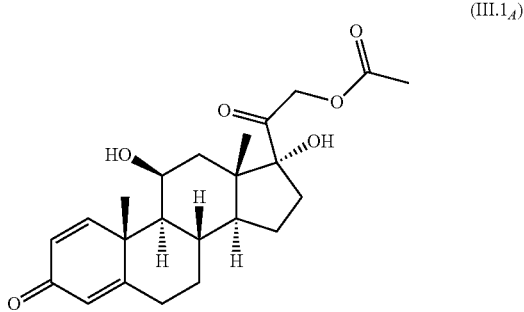

(III.1$_A$)

In the market, Prednisolone acetate is available as 25 mg/ml aqueous white suspension for injection which contains water for injection, Sodium chloride for injection, benzyl alcohol, sodium carboxymethylcellulose, Polysorbate 80, with sodium hydroxide or hydrochloric acid as pH adjuster.

This suspension requires good micronization of the drug (thus maintaining the particle size) and thus in all possibility of caking on storage particularly at low temperatures. Further phase separation on long storage can also occur. It is also prepared using costly methods.

By utilizing the vehicle or solvent of the present invention solvent, Diethylene glycol monoethyl ether or other alkyl derivatives, a transparent, non hazy solution is obtained, which can be useful as I.V. injection for rapid onset of action when required to provide earliest result into the patient. The solution may additionally contain preservatives and buffers for maintenance of pH. The solution shows good stability and can be used directly for parenteral use, obviating the need for lyophilization when metal salts are used. The solution can also be used for formulation of other dosage forms, such as capsules, tablets, eye drops, ear drops etc.

III.2) Methyl Prednisolone (Steroids & Hormones)

Methylprednisolone is a synthetic glucocorticoid or corticosteroid drug. It is a variant of prednisolone, methylated at carbon 6 of the B ring. The molecular structure of this lipophilic active is as:

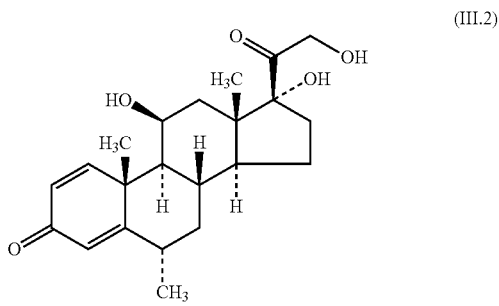

(III.2)

Methylprednisolone is typically used for its anti-inflammatory effects. Methylprednisolone occurs as a white to practically white, odorless, crystalline powder. It is sparingly soluble in alcohol, in dioxane, and in methanol, slightly soluble in acetone, and in chloroform, and very slightly soluble in ether. It is practically insoluble in water.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injection for rapid onset of action when required to provide earliest result into the patient as well as can be used for formulation of different dosage forms like capsules, nasal sprays, gargles, gels, topicals, liquid oral dosage forms etc. The solution may additionally contain preservatives and buffers for maintenance of pH.

III.2$_A$) Methyl Prednisolone Acetate (Steroids & Hormones)

Methyl Prednisolone acetate is an anti-inflammatory glucocorticoid available as intramuscular, intra-articular, soft tissue or intralesional injection. It is available in three strengths: 20 mg/Ml; 40 mg/ml; 80 mg/ml. The chemical name for methylprednisolone acetate is pregna-1, 4-diene-3, 20-dione, 21 (acetyloxy)-11,17-dihydroxy-6-methyl-, (6α, 11β)—and the molecular weight is 416.51. The structural formula is represented below:

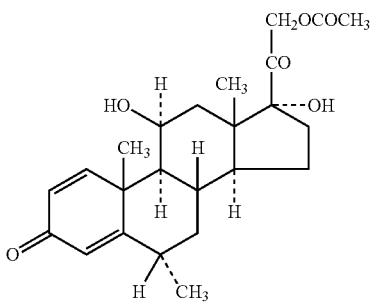

(III.2$_A$)

It is available as sterile aqueous suspension so the stability of such product may be issue for long time storage. Polyethylene glycol used in the product increases the viscosity of the formulation (Gibaldi's Drug Delivery System in Pharmaceutical Care, Page No. 117) which may be also an issue concern with the pain to patient at the site of application.

As it is available in suspension form, stability, particle size, and storage of the product are critical factors for handling. By utilizing the vehicle or solvent of the present invention solvent, Diethylene glycol monoethyl ether or other alkyl derivatives, a transparent, non hazy as well as less viscous solution is obtained, which can be useful to use as I.M as well as I.V. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

III.3) Medroxy Progesterone Acetate (Steroids & Hormones)

Medroxyprogesterone acetate, also known as 17α-hydroxy-6α-methylprogesterone acetate, and commonly abbreviated as MPA, is a steroidal progestin, a synthetic variant of the human hormone progesterone. It is used as a contraceptive, in hormone replacement therapy and for the treatment of endometriosis as well as several other indications. It is chemically designated as 17α-hydroxy-6α-methylpregn-4-ene-3,20-dione acetate and molecular structure is:

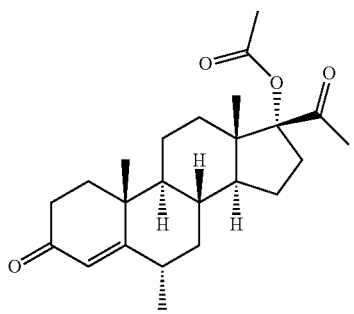

(III.3)

MPA is a more potent derivative of its parent compound Medroxyprogesterone. It is a white to off-white, odorless crystalline powder, stable in air, melting between 200° and 210° C. It is freely soluble in chloroform, soluble in acetone and in dioxane, sparingly soluble in alcohol and methanol, slightly soluble in ether and insoluble in water. It is available as Aqueous Suspension active by the parenteral and oral routes of administration. It is available as intramuscular injection in which each ml consists of 400 mg/ml MPA. The vehicle used as parenteral solvent is PEG 3350.

The viscosity of PEG 3350 is about 83 to 130 cps which is more viscous and is painful to a patient at the time of injection. As it is available in suspension form, stability, particle size, storage of the product are required to be monitored.

By utilizing the vehicle or solvent of the present invention solvent, Diethylene glycol monoethyl ether or other alkyl derivatives, a transparent, non hazy as well as less viscous solution is obtained, which can be useful to use as I.M as well as I.V. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

III.4) Triamcinolone Acetonide (Steroids & Hormones)

Triamcinolone acetonide is ester form of triamcinolone, a synthetic glucocorticoid corticosteroid with marked anti-inflammatory action. The chemical name for triamcinolone acetonide is 9-Fluoro-11β,16α,17,21-tetrahydroxypregna-1,4-diene-3,20-dione cyclic 16,17acetal with acetone. Its structural formula is:

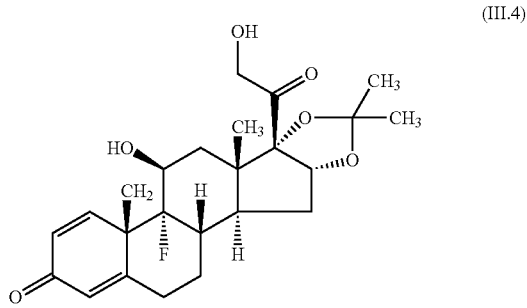

(III.4)

It is white to off-white crystalline powder, practically insoluble in water but soluble in alcohol and chloroform. It is available in a sterile aqueous suspension form in 40 mg dose in the market for intramuscular application. During administration of this product, many precautions have to be taken. Before using the vial is to be shaken to ensure a uniform suspension. During syringability, ruling out of clumping or granular appearance of the suspension before withdrawing into syringe is necessary. After withdrawal, injection is to be applied as soon as possible before it starts settling in the syringe. The entire problems are always an issue for a physician.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

III.5) Stanozolol (Steroids & Hormones)

Stanozolol is a synthetic anabolic steroid derived from dihydrotestosterone. It has been approved by the FDA for human use. Unlike most injectable anabolic steroids, 28aphtha28ol is not esterified and is sold as an aqueous suspension, or in oral tablet form. Thus this aqueous suspension can be prepared as clear viable I.M injectable preparation by using present art solvent. It is chemically designated as 1S,3As,3Br,5As,10As,10Bs,12As)-1,10a,12a-trimethyl-1,2,3,3a,3b,4,5,5a,6,7,10,10a,10b,11,12,12a-hexadecahydrocyclopenta [5,6]106aphtha[1,2-f]indazol-1-ol with chemical structure as:

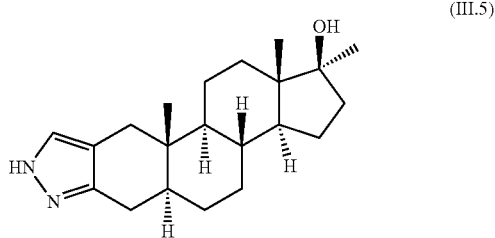

(III.5)

It is white crystal practically insoluble in water; soluble 1 in 41 of alcohol, 1 in 74 of chloroform, and 1 in 370 of ether; soluble in dimethylformamide; slightly soluble in acetone and ethyl acetate.

It is available as suspension. It is presented most commonly as a 50 mg/mL injection or a 5 mg tablet. However, recently 100 mg/mL versions have become available. A common dosage can be 10-25 mg/day orally and 25-50 mg daily injected. The suspension might have stability related problem on long storage; it is also required to maintain the particle size.

By utilizing the vehicle or solvent of the present invention solvent, Diethylene glycol monoethyl ether or other alkyl derivatives, a transparent, non hazy as well as less viscous solution is obtained, which can be useful as I.M as well as I.V. injection for rapid onset of action when required to provide earliest result into the patient. The solution may additionally contain preservatives and buffers for maintenance of pH. The same solution may be employed for other dosage forms for example, like capsule form.

III.6) Propofol (Hypnotic Agent)

Propofol is a short-acting, intravenously administered hypnotic agent. Its uses include the induction and maintenance of general anesthesia, sedation for mechanically ventilated adults, and procedural sedation. The chemical name of Propofol is 2,6-diisopropylphenol with molecular structure given as:

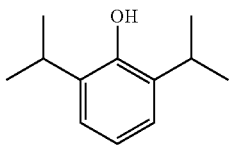

(III.6)

It is light yellow liquid, very slightly soluble in water, miscible with hexane and with methanol.

Propofol has been referred to as "milk of amnesia" because of the milk-like appearance of its intravenous preparation. The currently available preparation is 1% propofol, 10% soybean oil, and 1.2% purified egg phospholipid (like LIPOVA-E120) as an emulsifier, with 2.25% of glycerol as a tonicity-adjusting agent, and sodium hydroxide to adjust the pH. It also contains EDTA, a common chelation agent, that also acts alone (bacteriostatically against some bacteria) and synergistically with some other antimicrobial agents. Newer generic formulations contain sodium metabisulfite or benzyl alcohol as antimicrobial agents. Propofol emulsion is a highly opaque white fluid due to the scattering of light from the tiny (~150 nm) oil droplets that it contains. Thus from the above problem, milk of amnesia might be removed by using the present invention solvent using preferable preservatives and buffer with efficient process without any lyophilization for the drug and making cost effective product.

Doctors always prefer to use clear liquid to avoid any extraneous material directly injected into veins. The presently available injection has a difficulty in maintaining the particle size and also prohibitive for multiple uses because of the composition is rich in nitrogen to support microbial growth.

The cited problems in emulsion formulations can be overcome by formulating the drug using Diethylene glycol monoethyl ether in strength of 1 mg to 500 mg/ml and can administered with suitable adjuvants to directly infused in the infusion bag after modifying suitably and modified drug delivery system can be developed.

Viscosity of propofol is less than 5 cps.

By utilizing the vehicle or solvent of the present invention solvent, Diethylene glycol monoethyl ether or other alkyl derivatives, a transparent, non hazy as well as less viscous solution is obtained, which can be useful as I.V. bolus injection or Depot I.M. injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

III.7) Clevidipine Butyrate (Calcium Channel Blocker)

It is a dihydropyridine L-type calcium channel blocker. It is used to achieve the desired reduction in blood pressure. It is chemically designated as O3-(butanoyloxymethyl) O5-methyl (4R)-4-(2,3-dichlorophenyl)-2,6-dimethyl-1,4-dihydropyridine-3,5 dicarboxylate and molecular structure is given as

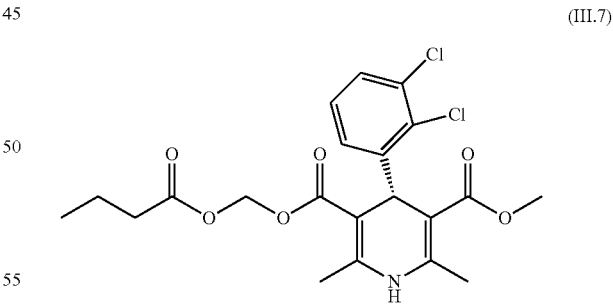

(III.7)

Clevidipine is practically insoluble in water and is generally formulated in an oil-in-water emulsion. Clevidipine butyrate is rapidly distributed and metabolized, resulting in an ultra-short half-life. So it is prepared in form of I.V injection. But the available marketed product is a sterile, milky-white opaque emulsion in a vial containing 0.5 mg/mL of Clevidipine butyrate for intravenous use as an infusion centrally or peripherally. The maximum recommended dose is 32 mg/h. It is a single-use parenteral product that contains phospholipids and can support the growth of micro organisms. Thus there are chances of contamination as well as stability problem of such emulsion when stored for a long time. Constant quality check on particle size, microbial load, caking and phase separation are required.

By utilizing the vehicle or solvent of the present invention solvent, Diethylene glycol monoethyl ether or other alkyl derivatives, a transparent, non hazy as well as less viscous solution is obtained, which can be useful as I.V. injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.8) Vitamin K (Vitamins & Minerals)

It belongs to a group of structurally similar, fat-soluble vitamins that the human body needs for posttranslational modification of certain proteins required for blood coagulation, and in metabolic pathways in bone and other tissue. They are 2-methyl-1,4-naphthoquinone (3-) derivatives. This group of vitamins includes two natural Vitamins: Vitamin $K_1$ (Phytomenadione) and Vitamin $K_2$ (Menaquinone). Vitamin $K_1$ is available as injectable emulsion through I.V., I.M. and S.C. (Subcutaneous) in the market, while Vitamin $K_2$ (MK) type is made orally available to mammals by natural dietary source.

Vitamin $K_1$: Phytomenadione is a Vitamin, which is a clear, yellow to amber, viscous, odorless or nearly odorless liquid. It is insoluble in water, soluble in chloroform and slightly soluble in ethanol. It has a molecular weight of 450.70.

Phytomenadione is 2-methyl-3-phytyl-1,4-naphthoquinone. Its empirical formula is $C_{31}H_{46}O_2$ and its structural formula is:

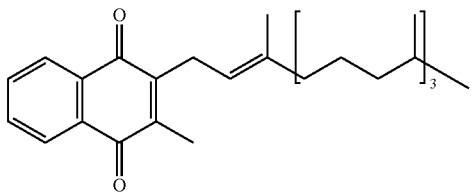

(III.8)

Vitamin K1 Injection (Phytomenadione Injectable Emulsion, USP) is a yellow, sterile, nonpyrogenic aqueous dispersion available for injection by the intravenous, intramuscular and subcutaneous routes. Each milliliter contains phytomenadione 2 or 10 mg, polyoxyethylated fatty acid derivative, dextrose, hydrous in water for injection; benzyl alcohol added as preservative. It may contain hydrochloric acid for pH adjustment. pH is 6.3 (range of 5.0 to 7.0).

This is an available emulsion which is yellow in color while it might be high cost process to provide desired particle size dispersion, thus stability can be issue. Thus a clear pellucid parenteral solution can be prepared by using the present invention solvent diethylene glycol monoethyl ether with addition of suitable preservatives and antioxidant as Phytomenadione is oxygen sensitive.

By utilizing the vehicle or solvent of the present invention solvent, Diethylene glycol monoethyl ether or other alkyl derivatives, a transparent, non hazy as well as less viscous solution is obtained, which can be useful as I.V. or I.M. injections for rapid onset of action when required to provide earliest result into the patient. The solution can also be used for formulation of different dosage forms like capsules, tablets, liquid oral dosage forms etc. The solution may additionally contain preservatives and buffers for maintenance of pH.

Analgesic Agents: (NSAIDs as Well as Narcotic Analgesics)

The Non-steroidal anti-inflammatory drugs (NSAIDs) has a wide range and they are available both in non-prescription and prescription mode. The major groups of NSAIDs which can be used to prepare parenteral I.V bolus as well as I.M preparations utilizing the vehicle or solvent of the present invention, Diethylene glycol monoethyl ether or other alkyl derivatives are given below:

Salicylic acid group: Aspirin (acetyl salicylic acid); Choline magnesium trisalicylate, Diflunisal and salsalate Propionic acid group: Fenoprofen, Flurbiprofen, Ibuprofen, Ketoprofen, Naproxen, and Oxaprozin; Acetic and acid group: Aceclofenac, Indomethacin, Sulindac, and Tolmetin; Fenamic acid group: Meclofenamate and Mefenamic acid; Napthylalkenone group: Nabumetone; Pyamocarboxylic acid group: Etodolac; Pyrrole group: Ketorolac.

The injections of NSAIDs can be prepared alone or in combination with other drugs for therapeutic purpose i.e, presently approved drugs can be made available in combination with other drugs combined to produce a clear injectables wherein wholly Diethylene glycol monoethyl ether up to 100% or can be used in varying concentration with other co-solvents without causing any physical changes like color change, crystal formation, etc.

Injection form is more advantageous over oral form of the compound as serum concentration of oral NSAID is lesser because of intestinal metabolism of the drug. Dry powder injectable NSAID needs to be lyophilized and then reconstituted before use. The process is costly and cumbersome. So, the present art is helpful to provide clear parenterals obviating above difficulties.

III.9) Aceclofenac (NSAID)

Aceclofenac is a non-steroidal anti-inflammatory drug (NSAID) used for the relief of pain and inflammation in rheumatoid arthritis, osteoarthritis and ankylosing spondylitis. Aceclofenac is the glycolic acid ester of diclofenac. The systemic name of this NSAID is 2-[2-[2-[(2,6-dichlorophenyl)amino]phenyl]acetyl]oxyacetic acid with the molecular structure as

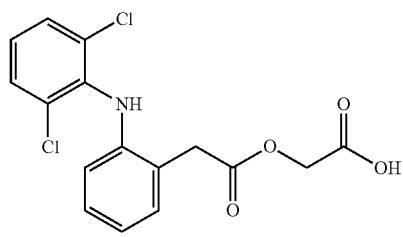

(III.9)

It is white crystalline powder practically insoluble in water, freely soluble in acetone, soluble in alcohol.

Aceclofenac is present as I.V bolus in market as dose of 150 mg per ml in which vehicles like Polyethylene glycol, TCLS01 solvent, Arginine solution for lyophilized Active are used.

In WO 2006054315 B1, the invention relates to nonaqueous liquid parenteral aceclofenac formulation in which propylene glycol was used as injectable vehicle which is viscous in nature (58.1 cps) that can be painful at the site of injection.

In Indian Patent Application No. 67/BOM/99, use of dimethyl isosorbide as a parenteral solvent in Aceclofenac injection was found to be irritant and pain full at site of injection.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, nasal sprays, gels, topicals, liquid oral dosage forms etc. The solution may additionally contain preservatives and buffers for maintenance of pH.

III.10) Ethinylestradiol (Steroids & Hormones)

Ethinyl estradiol is a derivative of 17β-estradiol (E2), the major endogenous estrogen in humans. It is an orally bioactive estrogen used in many formulations of combined oral contraceptive pills. It is one of the most commonly used medications for this purpose.

It is chemically denoted as 19-nor-17α-pregna-1,3,5(10)-trien-20-yne-3,17-diol with molecular structure as:

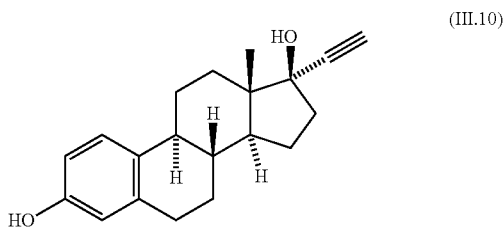

(III.10)

It is a white to slightly yellowish white, crystalline powder, odourless, practically insoluble in water; freely soluble in ethanol (~750 g/l) TS; soluble in acetone and dioxan.

It is available in the market as 0.5 mg and 1 mg of Ethinyl estradiol oral tablet. Most combination birth control pills today contain between 20 meg (low dose pills) to 30/35 meg of Ethinyl estradiol.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, liquid oral dosage forms etc. The solution may additionally contain preservatives and buffers for maintenance of pH.

III.11) Terbinafine (Antifungal Agent)

Terbinafine hydrochloride is a synthetic allylamine antifungal. It is highly lipophilic in nature. It prevents conversion of squalene to lanosterol, ergosterol cannot be synthesized. This is thought to change cell membrane permeability; causing fungal cell lysis. Terbinafine hydrochloride is a white fine, crystalline powder that is freely soluble in methanol and dichloromethane, soluble in ethanol, and slightly soluble in water. It is chemically designated as [(2E)-6,6-dimethylhept-2-en-4-yn-1-yl](methyl)(naphthalen-1-ylmethyl)amine with the molecular structure given as:

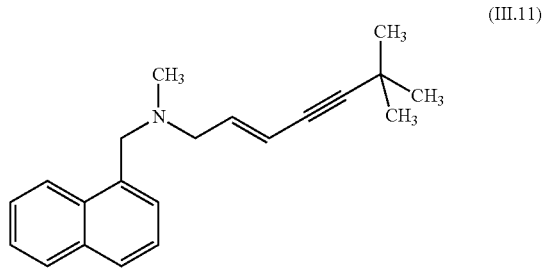 [SMILES: CN(C/C=C/C#CC(C)(C)C)Cc1cccc2ccccc12]

(III.11)

As a 1% cream or powder it is used for superficial skin infections. Oral 250 mg tablets are often prescribed for the treatment of onychomycosis of the toenail or fingernail due to the dermatophyte Tinea unguium. It is also available as gel. The drug accumulates in the skin tissues and in nails after ingestion or dermal application to have localized effect. It might be possible to formulate parenteral I.V Bolus for rapid onset of action by the present art.

By utilizing the vehicle or solvent of the present invention solvent, Diethylene glycol monoethyl ether or other alkyl derivatives, a transparent, non hazy as well as less viscous solution is obtained, which can be useful as I.V. bolus injection for rapid onset of action when required to provide earliest result into the patient as well as can be used for formulation of different dosage forms like capsules, nasal sprays, gargles, gels, topical, liquid oral dosage forms etc. The solution may additionally contain preservatives and buffers for maintenance of pH.

III.12) Roxythromycin (Antibiotic)

Roxythromycin is a semi-synthetic macrolide antibiotic. It is used to treat respiratory tract, urinary and soft tissue infections.

This lipophilic active is chemically designated as (3R,4S, 5S,6R,7R,9R,11S,12R,13S,14R)-6-[(2S,3R,4S,6R)-4-d-3-hydroxy-6-methyloxan-2-yl]oxy-14-ethyl-7,12,13-trihydroxy-4-[(2R,4R,5S,6S)-5-hydroxy-4-methoxy-4,6-dimethyloxan-2-yl]oxy-10-(2-methoxyethoxymethoxyimino)-3,5,7,9,11,13-hexamethyl-1-oxacyclotetradecan-2-one and molecular structure is given as:

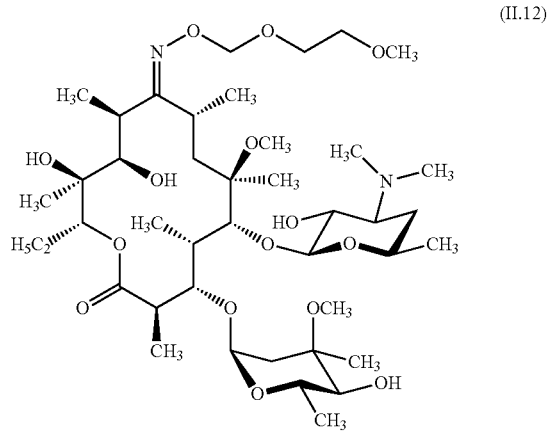

(II.12)

It is soluble in ethanol and acetone, methanol and ethyl ether dissolved, almost insoluble in water; 2, the water solubility: 0.1 g dissolved in 30 ml water.

By utilizing the vehicle or solvent of the present invention solvent, Diethylene glycol monoethyl ether or other alkyl derivatives, a transparent, non hazy as well as less viscous solution is obtained, which can be useful as i.V. or I.M. injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.13) Spironolactone (Aldosterone Receptor Antagonist)

Spironolactone is a potassium-sparing diuretic (water pill) that prevents your body from absorbing too much salt and keeps your potassium levels from getting too low. It is practically insoluble in water about 22 mg/L at 25° C. It is used to diagnose or treat a condition in which you have too much aldosterone in your body. It is chemically designated as 17-hydroxy-7α-mercapto-3-oxo-17α-pregn-4-ene-21-carboxylie acid, γ-lactone acetate and the molecular structure is:

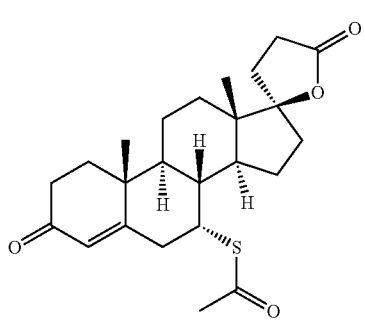

(III.13)

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.14) Eplerenone (Aldosterone Receptor Antagonist)

Eplerenone is an aldosterone antagonist used as an adjunct in the management of chronic heart failure. It is similar to the diuretic spironolactone, though it is much more selective for the mineralocorticoid receptor in comparison (i.e., does not possess any antiandrogen, progestogen, or estrogenic effects), and is specifically marketed for reducing cardiovascular risk in patients following myocardial infarction. It is chemically designated as pregn-4-ene-7,21-dicarboxylic acid, 9,11-epoxy-17-hydroxy-3-oxo, γ-lactone, methyl ester (7α, 11α, 17α) and molecular structure is

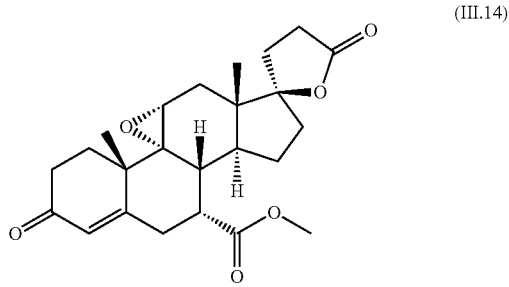

(III.14)

Eplerenone is an odorless, white to off-white crystalline powder. It is very slightly soluble in water, with its solubility essentially pH-independent. The octanol/water partition coefficient of eplerenone is approximately 7.1 at pH 7.0. These drugs are mostly available in market as oral tablet. This both actives are possible to be formulated as a parenteral for unconscious patient.

By utilizing the vehicle or solvent of the present invention solvent, Diethylene glycol monoethyl ether or other alkyl derivatives, a transparent, non hazy as well as less viscous solution is obtained, which can be useful as I.V. or I.M. injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.15) Amlodipine Besylate (Calcium Channel Blocker)

It is a long-acting calcium channel blocker. Amlodipine besylate, USP is chemically described as 3-Ethyl-5-methyl (±)-2-[(2-aminoethoxy) methyl] 4-(2-chlorophenyl)-1,4-di-hydro-6-methyl-3,5-pyridinedicarboxylate, mono benzene sulphonate. Its molecular formula is $C_{20}H_{25}ClN_2O_5 \cdot C_6H_6O_3S$ and its structural formula is:

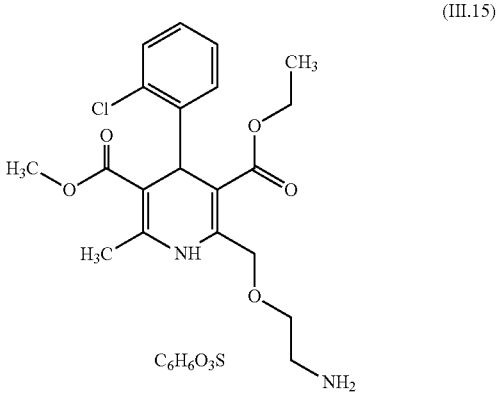 [SMILES: CCOC(=O)C1=C(COCCN)NC(C)=C(C(=O)OC)C1c1ccccc1Cl ; "C6H6O3S"]

(III.15)

It is slightly soluble in water. It is available as oral tablet in dose of 2.5, 5 and 10 mg and as capsule as per USP. According to 14 reports from FDA, it was found to have swelling at site of injection might be due to use of viscous solvents.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution further avoids swelling at the site of injection. The solution may additionally contain preservatives and buffers for maintenance of pH.

III.16) Barnidipine Hydrochloride (Calcium Channel Blocker)

It is found to be safer antihypertensive agent used to provide hypotension effect in patient. It is chemically designated as 3-(3R)-1-benzylpyrrolidin-3-yl 5-methyl 2,6-dimethyl-4-(3-nitrophenyl)-1,4-dihydropyridine-3,5-dicarboxylate and molecular structure is

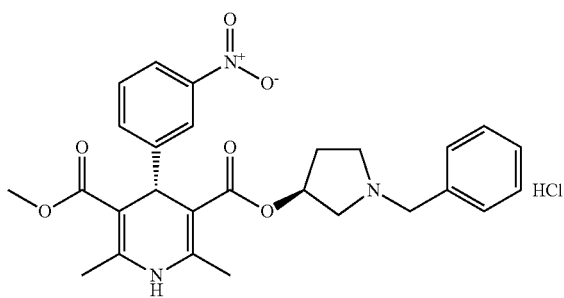

(III.16)

It is a light yellow crystalline powder which is insoluble in water while soluble in DMSO and methanol. This product is available in capsule form in dose strength of 5, 10, 15 mg.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.17) Benidipine Hydrochloride (Calcium Channel Blocker)

It is a new hypertensive agent i.e., dihydropyridine calcium channel blocker for the treatment of high blood pressure, licensed in Japan for oral administration. It is chemically known as O5-methyl O3-[(3R)-1-(phenyl methyl) piperidin-3-yl] 2,6-dimethyl-4-(3-nitrophenyl)-1,4-dihydropyridine-3,5-dicarboxylate and its molecular structure is given as:

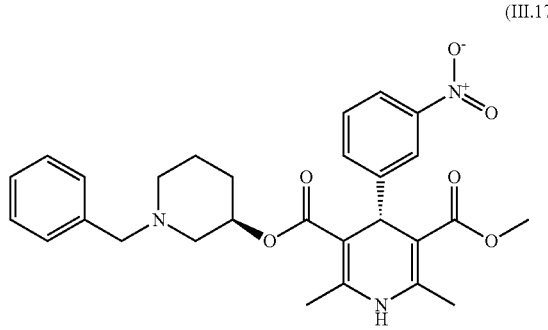

(III.17)

It is occurs as a yellow crystalline powder. It is very soluble in formic acid, soluble in methanol, sparingly soluble in ethanol and practically insoluble in water.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.18) Nifedipine (Calcium Channel Blocker)

Nifedipine is a dihydropyridine calcium channel blocker. Its main uses are as an anti-anginal and antihypertensive, It is chemically designated as Dimethyl 2,6-dimethyl-4-(2-nitrophenyl)-1,4-dihydropyridine-3,5-dicarboxylate and molecular structure is.

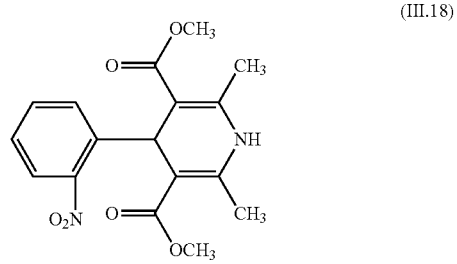 [SMILES: COC(=O)C1=C(C)NC(C)=C(C(=O)OC)C1c1ccccc1[N+](=O)[O-]]

(III.18)

It has a molecular weight of 346.3, practically insoluble in water. It is available as capsules are formulated as soft gelatin capsules for oral administration, each containing 10 mg Nifedipine, in which glycerin and PEG is used as inert excipients.

According to Chinese Patent No. 94110139, this invention refers to a Nifedipine injection belonged to calcium antagonist. It is prepared, by involving Nifedipine, polyvinyl pyrrolidone, alcohol for injection at ratio of formulation required to obtain the product.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution may additionally contain preservatives and buffers for maintenance of pH.

III.19) Cilnidipine (Calcium Channel Blocker)

Cilnidipine is the novel calcium antagonist accompanied with L-type and N-type calcium channel blocking function. Due to its N-type calcium-channel blocking properties, it has more advantages compared to conventional calcium-channel blockers. It has lower incidence of Pedal edema, one of the major adverse effects of other calcium channel blockers. Cilnidipine has similar blood pressure lowering efficacy as compared to Amlodipine. The chemical name of this active is O3-(2-methoxyethyl) O5-[(E)-3-phenylprop-2-enyl] 2,6-dimethyl-4-(3-nitrophenyl)-1,4-dihydropyridine-3,5-dicarboxylate and the molecular structure is given as:

(III.19)

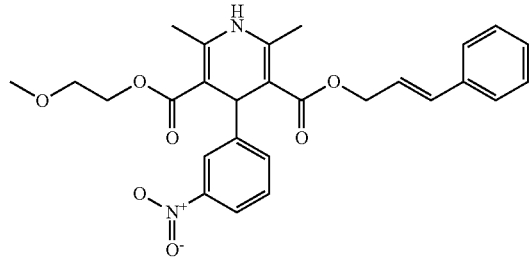

It is available in marketed as oral tablet in dose of 5 mg, 10 mg, and 40 mg. This medication works by inhibiting the action of angiotensin receptors, thereby helping to control hypertension.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, liquid oral dosage forms etc. The solution may additionally contain preservatives and buffers for maintenance of pH.

Other Calcium Channel Blockers like Darodipine, Nimodipine, Nisoldipine, Nitrendipine, Felodipine, Nicardipine, and Isradipine can also be formulated into clear pellucid solutions for I.V. or I.M. injections utilizing the vehicle or solvent of the present invention, Diethylene glycol monoethyl ether or other alkyl derivatives.

III.20) Captopril

It is an angiotensin-converting enzyme (ACE) inhibitor used for the treatment of hypertension and some types of congestive heart failure. Captopril was the first ACE inhibitor developed. It is chemically designated as (2S)-1-[(2S)-2-methyl-3-sulfanylpropanoyl] pyrrolidine-2-carboxylic acid and molecular structure is:

(III.20)

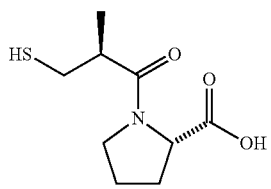

It is easily soluble in water but might get converted into salt form so I.V form might be not developed yet till now. Small intravenous bolus injections of captopril may appear to be effective rapidly and can be well tolerated in moderate to severe essential hypertension. Short-term intravenous administration seems to predict the response to chronic oral captopril therapy. Thus by the present art, I.V bolus parenteral can be prepared by first converting this active into acid form which is then solubilize in diethylene glycol monoethyl ether.

By utilizing the vehicle or solvent of the present invention solvent, Diethylene glycol monoethyl ether or other alkyl derivatives, a transparent, non hazy as well as less viscous solution is obtained, which can be useful as I.V. bolus injection or Depot I.M. injection for rapid onset of action when required to provide earliest result into the patient as well as can be used for formulation of different dosage forms like capsules, nasal sprays, gargles, gels, topical, liquid oral dosage forms, otic delivery systems etc. The solution may additionally contain preservatives and buffers for maintenance of pH.

Other commercially available ACE inhibitors like Ramipril, Fosinopril, Zofenopril, Perindopril, Quinapril, Lisinopril etc., which are lipophilic in nature can also be formulated by utilizing the vehicle or solvent of the present invention solvent, Diethylene glycol monoethyl ether or other alkyl derivatives, a transparent, non hazy as well as less viscous solution is obtained, which can be useful as I.V. bolus injection or Depot I.M. injection for rapid onset of action when required to provide earliest result into the patient as well as can be used for formulation of different dosage forms like capsules, nasal sprays, gargles, gels, topical, liquid oral dosage forms, otic delivery systems etc. The solution may additionally contain preservatives and buffers for maintenance of pH.

III.21) Celecoxib

Celecoxib is a sulfonamide NSAID and selective COX-2 inhibitor used in the treatment of osteoarthritis, rheumatoid arthritis, acute pain. The chemical name of celecoxib is with molecular structure as:

(III.21)

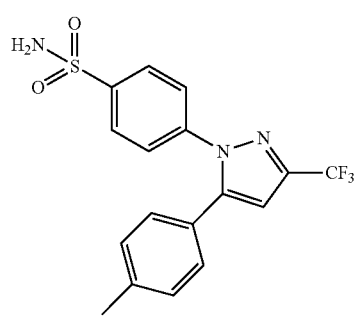

It is soluble in DMSO at 200 mg/mL; soluble in ethanol at 100 mg/mL; very poorly soluble in water; Celecoxib is available by prescription in capsule form and as I.V bolus parenteral in market. The pain relief offered by celecoxib is similar to that offered by paracetamol.

The prior art indicates that such injections are prepared and marketed using Dimethyl Isosorbide which is painful at the site.

Celecoxib is soluble in Diethylenglycol monoether ether and with other cosolvents like dimethyl isosorbide in minimum quantity To overcome the problem of pain and irritancy at site of injections the I.V/I.M Injection of Etoricoxib and Celecoxib is prepared by dissolving 60, 90, 120 mg/ml solution and 100 mg/ml/200 mg/ml in Diethylene glycol monoethyl ether with antioxidant and preservative respectively.

It offers an advantage of less painful, less viscous free flowing easily syringable liquid. It offers a quick onset of action.

By utilizing the vehicle or solvent of the present invention solvent, Diethylene glycol monoethyl ether or other alkyl derivatives, a transparent, non hazy as well as less viscous solution is obtained, which can be useful as I.V. injection for rapid onset of action when required to provide earliest result into the patient as well as can be used for formulation of different dosage forms like capsules, gels, patches, liquid oral dosage forms etc. The solution may additionally contain preservatives and buffers for maintenance of pH.

III.22) Isoxsuprine Hydrochloride (Anti-Arrhythmic Drug)

It is beta-adrenergic agonist that causes direct relaxation of uterine and vascular smooth muscle. Its vasodilating actions are greater on the arteries supplying skeletal muscle than on those supplying skin. It is used in the treatment of peripheral vascular disease and in premature labor. The chemical name of this lipophilic active is 4-[1-hydroxy-2-(1-phenoxypropan-2-ylamino) propyl] phenol hydrochloride. Isoxsuprine hydrochloride occurs as a white odorless, crystalline powder, having a bitter taste. It has a following structural formula:

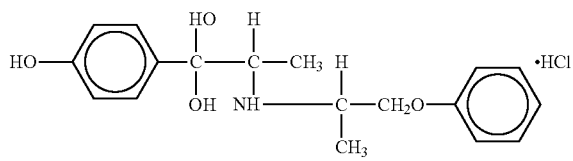

(III.22)

It is marketed as Tablet form of dose strength 20 mg and as parenteral infusion as well as I.M parenteral of 5 mg/ml. An intravenous infusion is prepared by dilution of the injection in an appropriate quantity of 5% dextrose injection, 5% dextrose in 0.45% sodium chloride injection, or 5% dextrose in 0.23% sodium chloride injection. Dilution in 0.9% sodium chloride injection is not recommended because of the risk of pulmonary edema. Because of the risk of hypotension and tachycardia, single intramuscular doses greater than 10 mg are not recommended.

By utilizing the vehicle or solvent of the present invention solvent, Diethylene glycol monoethyl ether or other alkyl derivatives, a transparent, non hazy as well as less viscous solution is obtained, which can be useful as injections for rapid onset of action when required to provide earliest result into the patient as well as can be used for formulation of different dosage forms like capsules, tablets, nasal sprays, gargles, gels, topicals, liquid oral dosage forms etc. The solution may additionally contain preservatives and buffers for maintenance of pH.

III.23) Drugs Related to Ophthalmic Suspension (Ocular) and Otic Suspension

Drugs that are prepared for ophthalmic as well as otic suspensions can also be formulated as clear pellucic solutions, which are further transparent, non hazy and less viscous by utilization of the vehicle or solvent of the present invention solvent, Diethylene glycol monoethyl ether or other alkyl derivatives.

In the prior art formulations the particles in the suspension have a tendency of sedimentation and aggregation. If administered in to the tissues, often lead to irritation and embolism (e.g. Eye drops having suspended particles can cause irritation to mucosal membrane of eyes causing pain and discomfort to the patients, embolism which is caused due to particles infused as I.V.

The preparations using Diethylene glycol monoethyl ether or other alkyl derivatives are clear limpid, free from particulate matter and devoid of particle agglomeration.

Table-I provides Drugs belonging to different pharmacological or therapeutic classes which can also be formulated as clear pellucic solutions, which are further transparent, non hazy and less viscous by utilization of the vehicle or solvent of the present invention solvent, Diethylene glycol monoethyl ether or other alkyl derivatives.

TABLE 1

Drugs Available as Opthalmic Suspensions and Otic Suspensions

| Code | Drug & Therapeutic Category | Chemical Structure & Chemical Name | Solubility Profile | Formalations Available in the Market & their Problems |
|---|---|---|---|---|
| | | Ophthalmic Suspensions | | |
| III.23$_A$ | Brinzolamide Carbonic Anhydrase Inhibitor | | Insoluble in water, very soluble in methanol and soluble in ethanol. Solubility in Diethylene glycol monoethyl ether is 55.35 mg/ml. | As a Sterile, Aqueous Suspension of Brinzolamide which has been formulated to be readily suspended and slow settling, following shaking. It has a pH of approximately 7.5 and and osmolality of 300 mOsm/kg, 1% (10 mg/ml) opthalmic suspension Settling Problem of Suspension |
| III.23$_B$ | Difluprednate Anti-inflammatory Corticosteroid | | Very low solubility in water | Sterile Preserved Opthalmic Emulsion for the Treatment of Inflammation and Pain associated with Ocular Surgery. 0.05% is a Sterile, Topical Anti-inflammatory Corticosteroid for Ophthalmic use.D ifluprednate 0.5 mg (0.05%); INACTIVE: Boric acid, Castor oil, Glycerin, Polysorbate 80, Water for injection, Sodium acetate, Sodium EDTA, Sodium hydroxide (to adjust the pH to |

TABLE 1-continued

Drugs Available as Opthalmic Suspensions and Otic Suspensions

| Code | Drug & Therapeutic Category | Chemical Structure & Chemical Name | Solubility Profile | Formalations Available in the Market & their Problems |
|---|---|---|---|---|
| | | | | 5.2 to 5.8). The emulsion is essentially isotonic with a tonicity of 304 to 411 mOsm/kg. PRESERVATIVE: Sorbic acid 0.1%. Settling Problems and Unwanted Chemicals like Castor Oil being used |
| III.23$_C$ | Fluorometholone Acetate Anti-inflammatory Corticosteroid | 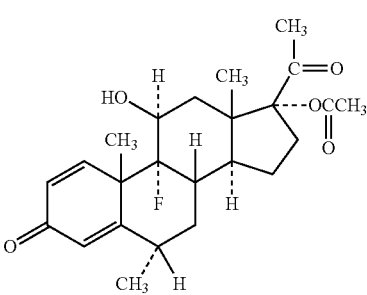 | Freely soluble in chloroform and acetone, soluble in ethanol, very slightly soluble in water | Opthalmic Suspension (not for injection) Flarex (Fluorometholone Acetate Ophthalmic Suspension) Sterile Each mL contains: Active: Fluorometholone acetate 1 mg (0.1%). Preservative: Benzalkonium chloride 0.01%. Inactives: Sodium chloride, Monobasic sodium phosphate, Edetate disodium, Hydroxyethyl cellulose, Tyloxapol, Hydrochloric acid and/or Sodium hydroxide (to adjust pH), and purified water. The pH of the Suspension is approximately 7.3, with an Osmolality of approximately 300 mOsm/kg. Partile Size Control and Irritation if Agglomeration occurs. |
| III.23$_D$ | Loteprednol Anti-inflammatory Corticosteroid | 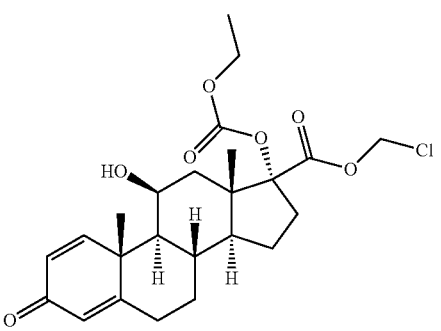 | Soluble in DMSO 34%, in 0.83% ethanol, 0.2241% propylene glycol, 8 µg per lt in water. | Sterile, Topical Anti-inflammatory Corticosteroid The active ingredient is Loteprednol Etabonate. Each ml contains 5 mg (0.5%) Loteprednol Etabonate. The other ingredients are Disodium Edetate, Glycerol, Povidone, Purified Water and Tyloxapol. Benzalkonium Chloride (0.01%) is added as a preservative. Sodium Hydroxide and/or Hydrochloric Acid are added to adjust the pH. Suspension and Particle Size Controls. |
| III.23$_E$ | Besifloxacin Antibacterial | 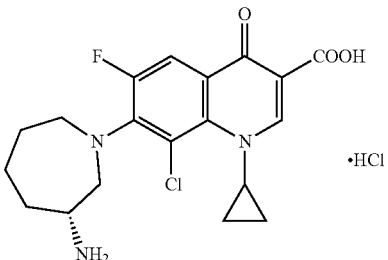 | Sparingly soluble in methanol, Sparingly soluble in water (1 mg/mL), DMSO (<1 mg/mL) | 0.6% Suspension: Opthalmic Suspension formulated with DuraSite Technology 6.63 mg Besifloxacin Hydrochloride equivalent to 6 mg Besifloxacin Base (6 mg/ml) Suspension and Control on Particles |

TABLE 1-continued

Drugs Available as Opthalmic Suspensions and Otic Suspensions

| Code | Drug & Therapeutic Category | Chemical Structure & Chemical Name | Solubility Profile | Formalations Available in the Market & their Problems |
|---|---|---|---|---|
| III.23$_F$ | Loteprednol Etabonate + Tobramycin Anti-inflammatory Corticosteroid + Antibiotic | 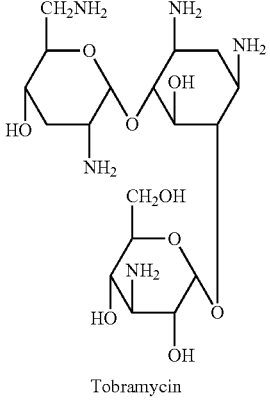<br>Tobramycin | Solubility of Tobramycin: Soluble in water; very slightly soluble in 100% ethanol. Solubiltiy in Diethylene glycol monoethyl ether: 25 mg/ml Solubiltiy in Diethylene glycol monoethyl ether: 3 mg/ml | Ocular Steroid Suspension Each mL contains: Actives: Loteprednol Etabonate 5 mg (0.5%) and Tobramycin 3 mg (0.3%). Inactives: Edetate Disodium, Glycerin, Povidone, Purified Water, Tyloxapol, and Benzalkonium Chloride 0.01% (preservative). Sulfuric Acid and/or Sodium Hydroxide may be added to adjust the pH to 5.7-5.9. The suspension is essentially isotonic with a tonicity of 260 to 320 mOsm/kg. The control on particle size is a consistent problem for both the drugs |
| III.23$_G$ | Brimonidine + Brinzolamide Carbonic Anhydrase Inhibitor + Antiglaucoma Agent | 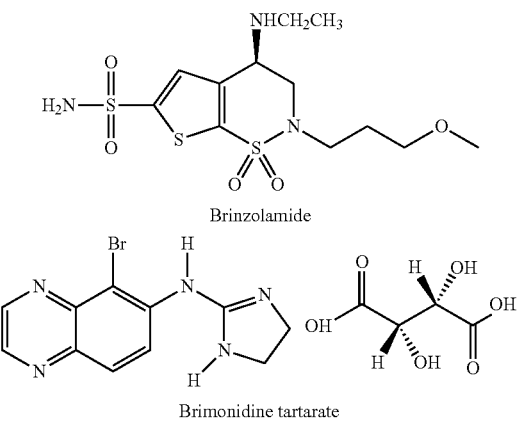<br>Brinzolamide<br><br>Brimonidine tartarate | Brinzolamide: insoluble in water, very soluble in methanol and soluble in ethanol. Brimonidine tartarate: soluble in water (34 mg/mL) at pH 6.5 | Opthalmic Suspension (1%/0.2%) 10 mg/ml Brinzolamide 2 mg/ml Brimonidine Tartarate Particle Size Control is essential |
| III.23$_H$ | Rimexolone Glucocorticoid Steroid | 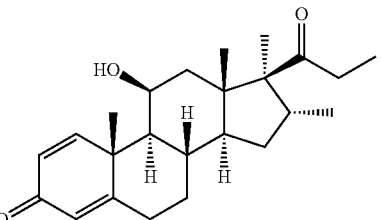 | Very slightly soluble in water; freely soluble in chloroform; soluble in ethyl acetate and in methanol | 1% Opthalmic Suspension Control on Particle Size is essential |
| III.23$_I$ | Sulfacetamide + Prednisolone Acetate Antibacterial + Corticosteroid | 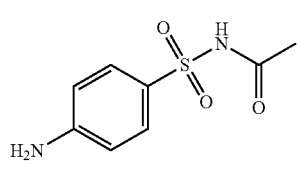<br>Sulphactamide | Sulfacetamide: Water-soluble <0.01 g/100 mL at 16° C. | Opthalmic Suspension 10% Sulfacetamide 0.2% Prednisolone Acetate Control on Particle Size |

TABLE 1-continued

Drugs Available as Opthalmic Suspensions and Otic Suspensions

| Code | Drug & Therapeutic Category | Chemical Structure & Chemical Name | Solubility Profile | Formalations Available in the Market & their Problems |
|---|---|---|---|---|
| III.23$_J$ | Tobramycin + Dexamethasone Antibiotic + Steroid | 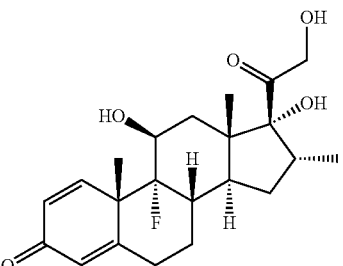<br>Dexamethasone | 3 mg/ml Tobramycin 1 mg/ml Dexamethasone | Opthalmic Suspension (0.3%/0.1%) Control on Particle Size |
| III.23$_K$ | Neomycin Sulphate + Polymixin B Sulphate + Dexamethasone Antibiotic + Glucocorticoid | 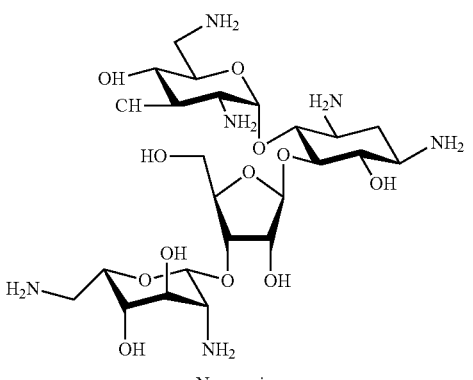<br>Neomycin | Each gram contains: Neomycin sulphate: 3.5 mg Polymixin B sulphate: 10.000 unit Dexamethasone: 0.1% (1 mg) | As an anti-infective Steroid combination as Sterile Topical Ointment (3.5 g Sterile Ointment in an aluminium tube) Control on Particle Size |
| III.23$_L$ | Nepafenac NSAID | 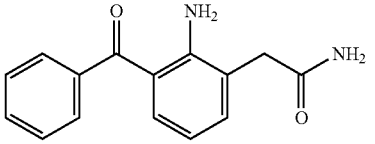 [SMILES: NC(=O)Cc1cccc(C(=O)c2ccccc2)c1N] | Soluble in DMSO and Methanol Solubility in diethyleneglycol mono ethyl ether is found<br><br>upto 2 mg/ml | Each mL contains: Active: Nepafenac 0.1% Inactives: Mannitol, Carbomer 974P, Sodium chloride, Tyloxapol, Edetate disodium, Benzalkonium chloride 0.005% (Preservative), Sodium<br><br>hydroxide and/or Hydrochloric acid to adjust pH and purified water, USP. Control on Particle Size |
| III.23$_M$ | Betaxolol Hydrochloride Beta$_1$ Receptor Blocker | 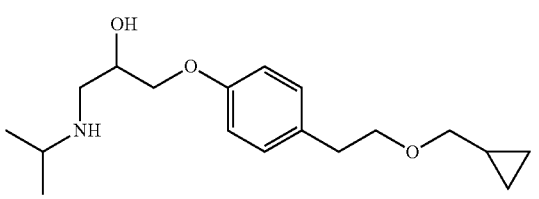 [SMILES: CC(C)NCC(O)COc1ccc(CCOCC2CC2)cc1] | Freely soluble in water, ethanol, chloroform, and methanol. | Opthalmic Solution/Drops Betaxolol Hydrochloride 0.5% Opthalmic Solution/Drops- Falcon Pharmaceuticals Each 5.6 mg Betaxolol Hydrochloride equivalent to Betaxolol base 5 mg Control on Particle Size |

TABLE 1-continued

Drugs Available as Opthalmic Suspensions and Otic Suspensions

| Code | Drug & Therapeutic Category | Chemical Structure & Chemical Name | Solubility Profile | Formalations Available in the Market & their Problems |
|---|---|---|---|---|

Otic Suspensions

| III.23$_N$ | Ciprofloxacin & Dexamethasone Antibacterial + Glucocorticoid | 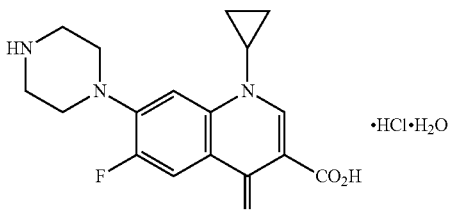<br>Ciprofloxacin HCl | Ciprofloxacin: Soluble in water; slightly soluble in methanol R; very slightly soluble in ethanol (~750 g/l) TS; practically insoluble in acetone R and dichloromethane R. | Sterile Otic Suspension (Ciprofloxacin 0.3% and Dexamethasone 0.1%) Ciprofloxacin Hydrochloride (equivalent to 3 mg Ciprofloxacin Base), 1 mg Dexamethasone Control on Particle Size |

Class IV: Drugs Belonging to Other Therapeutic Categories

Table-II provides Drugs belonging to different pharmacological or therapeutic classes which can also be formulated as clear pellucic solutions, which are further transparent, non hazy and less viscous by utilization of the vehicle or solvent of the present invention solvent, Diethylene glycol monoethyl ether or other alkyl derivatives. The solutions can be useful as I.V. or I.M. injections for rapid onset of action when required to provide earliest result into the patient, but also does not have the safety and toxicity issues associated with Cremophor® EL. The solution can also be used for formulation of different dosage forms like capsules, tablets, liquid oral dosage forms etc. The solution may additionally contain preservatives and buffers for maintenance of pH.

TABLE II

Drugs Belonging to Different Pharmacological or Therapeutic Classes

| Code | Drug & Therapeutic Category | Chemical Structure & Chemical Name | Solubility Profile | Form Available In The Market |
|---|---|---|---|---|
| IV.1 | Vinpocetine An inhibitor of Ca$^{2+}$/CaM-PDE with Neuroprotective properties | 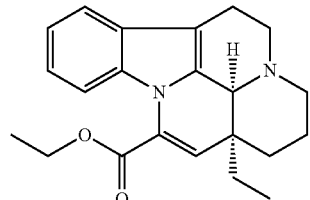<br>(3α,16α)-Eburnamenine-14-carboxylic acid ethyl ester | Soluble in DMSO, DMF, ethanol, acetic acid, acetone, and chloroform. Insoluble in water. | As an Oral, I.V. as Supplement |
| IV.2 | Itraconazole Triazole Antifungal Agent | 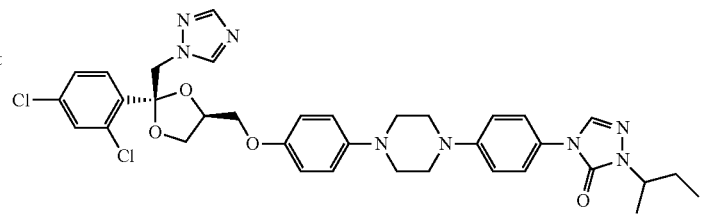<br>(2R,4S)-rel-1-(butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-1H-1,2,4-triazol-5-one | Soluble in organic solvents such as DMSO and dimethyl formamide. Insoluble in water. | Available as Capsules or as an Oral Solution |

TABLE II-continued

Drugs Belonging to Different Pharmacological or Therapeutic Classes

| Code | Drug & Therapeutic Category | Chemical Structure & Chemical Name | Solubility Profile | Form Available In The Market |
|---|---|---|---|---|
| IV.3 | Nimodipine Potent L-type Ca2+ Channel Antagonist | 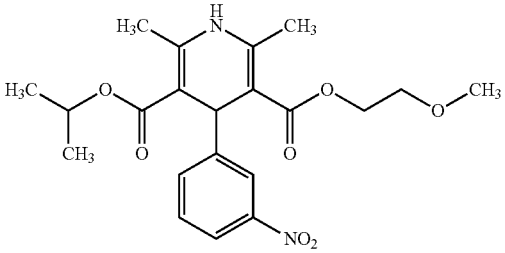<br>3-(2-methoxyethyl) 5-propan-2-yl 2,6-dimethyl-4-(3-nitrophenyl)-1,4-dihydropyridine-3,5-dicarboxylate | Soluble in methanol. Insoluble in water and beta cyclodextrin | As Film Coated Tablet, Intravenous Injection |
| IV.4 | Ezetimibe Anti-hyperlipidemic | 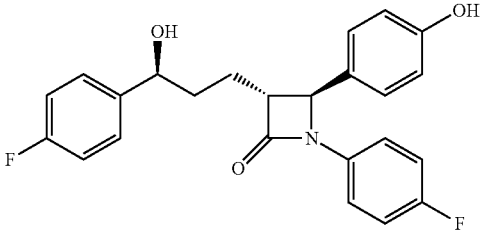<br>(3R,4S)-1-(4-fluorophenyl)-3-[(3S)-3-(4-fluorophenyl)-3-hydroxypropyl]-4-(4-hydroxyphenyl)azetidin-2-one | Freely to very soluble in ethanol, methanol, and acetone and practically insoluble in water. | As Tablet of 10 mg. |
| IV.5 | Valproic acid Anticonvulsant and Mood-stabilizing Agent | 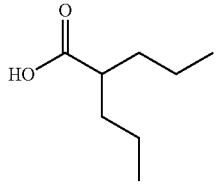<br>2-Propylpentanoic acid | A colorless liquid with a characteristic odor. It is slightly soluble in water (1.3 mg/mL) and very soluble in organic solvents. | As 250 mg of Soft Elastic Capsule, Enteric Coated Capsule, Syrup Solution, I.V. Injectable Form. |
| IV.6 | Bexarotene Antineoplastic Agent | 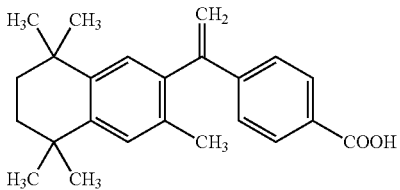<br>4-[1-(5,6,7,8-tetrahydro-3,5,5,8,8-pentamethyl-2-naphthalenyl) ethenyl] benzoic acid | Insoluble in water and slightly soluble in vegetable oils and ethanol, USP | As 75 mg of Soft Gelatin Capsule, Topical Soft Gel. |
| IV.7 | Tretinoin Anti-acne Drug | 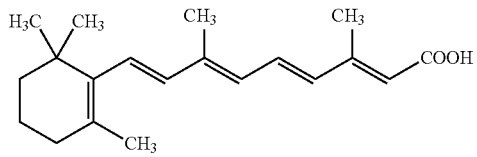<br>Retinoic acid | Insoluble in water | As Cream or Gel of 30, 45, 60 mg, 30 ml Liquid Solution; Soft Capsule of 10, 20, 30, 40 mg. Tablet |

TABLE II-continued

Drugs Belonging to Different Pharmacological or Therapeutic Classes

| Code | Drug & Therapeutic Category | Chemical Structure & Chemical Name | Solubility Profile | Form Available In The Market |
|---|---|---|---|---|
| IV.8 | Loperamide Anti-diarrheal | 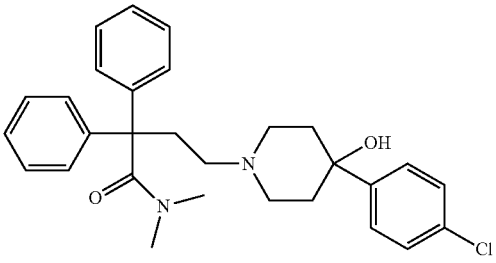<br>4-[4-(4-chlorophenyl)-4-hydroxypiperidin-l-yl]- N,N-dimethyl-2,2-diphenylbutanamide | Yellow powder insoluble in water | A Tablet, Capsule, and Liquid to be taken by mouth |
| IV.9 | Melphalan Alkylating Agent | 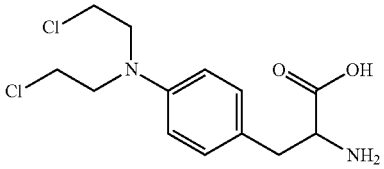<br>3-(p-(bis(2-chloroethyl)amino)phenyl)-1-alanine; 3(p-(bis(2-chloroethyl)amino)phenyl)-1-alanine | <0.1 g/100 mL at 22° C., 95% ethanol and 1 drop 6 N HCl: 0.05 g/mL | 50 MG Injectable Vial, 2 mg Tablet. |
| IV.10 | Tadalafil PDE5 Inhibitor | 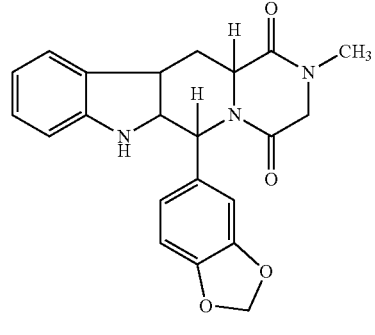 | Insoluble in water and very slightly soluble in ethanol | As almond shaped Tablet. |
| IV.11 | Loxapine (Loxapine Succinate) Antipsychotic | 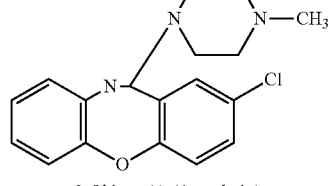<br>2-Chloro-11-(4-methyl-1-piperazinyl)dibenz[6,f][1.4]oxazepine | Sparingly soluble in H2O, freely soluble in DMS | Available as Capsule |
| IV.12 | Amilsulpride Antipshycotic | 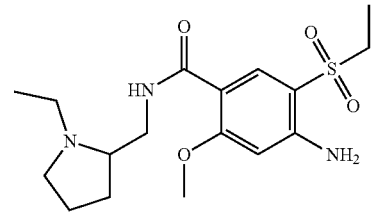<br>(RS)-4-amino-N-[(l-ethylpyrrolidin-2-yl)methyl]-5-ethylsulfonyl-2-methoxy-benzamide | Practically insoluble in water, sparingly soluble in ethanol, soluble in methanol and freely soluble in dichloromethane | Available as Tablet and 100 mg/ml Solution Form. |

TABLE II-continued

Drugs Belonging to Different Pharmacological or Therapeutic Classes

| Code | Drug & Therapeutic Category | Chemical Structure & Chemical Name | Solubility Profile | Form Available In The Market |
|---|---|---|---|---|
| IV.13 | Tacrolimus Antibiotic | 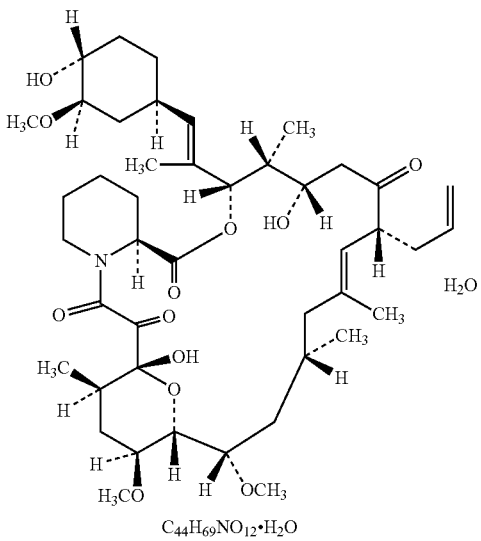<br>$C_{44}H_{69}NO_{12} \cdot H_2O$ | Insoluble in water, freely soluble in ethanol, and very soluble in methanol and chloroform. | Available as Capsule & 5 mg/ml Injection. |
| IV.14 | Doxorubicin Anticancer Agent | 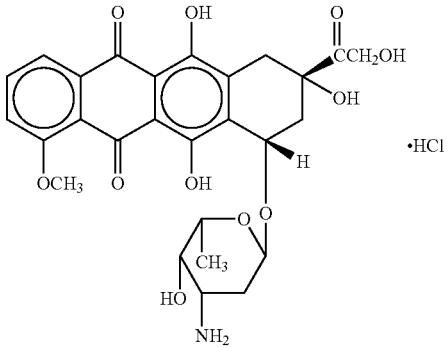<br>(8S,10S)-10-[(3-Amino-2,3,6-trideoxy-a-L-lyxo-hexopyranosyl)-oxy]-8-glycoloyl-7,8,9,10-tetrahydro-6,8,11-trihydroxy-1-methoxy-5,12-naphthacenedione hydrochloride | Soluble in DMSO at 100 mg/mL; very poorly soluble in ethanol; soluble in water at 10 mg/mL with slight warming. | Available as 2 mg/ml Multidose Vials & as Lyophilized Powder. |
| IV.15 | Olanazapine Antipsycotic | 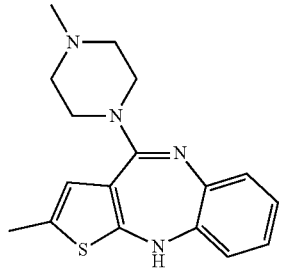<br>2-methyl-4-(4-methyl-1-piperazinyl)-10H-thieno[2,3-b][1,5]benzodiazepine | Olanzapine is soluble in organic solvents such as ethanol, DMSO, and dimethyl formamide, which should be purged with an inert gas. The solubility of olanzapine in these solvents is approx. 1, 16, and 20 mg/ml, respectively. | As Yellow Lyophilized Powder for Injection. |

TABLE II-continued

Drugs Belonging to Different Pharmacological or Therapeutic Classes

| Code | Drug & Therapeutic Category | Chemical Structure & Chemical Name | Solubility Profile | Form Available In The Market |
|---|---|---|---|---|
| IV.16 | Fluticasone Propionate Corticosteroid | 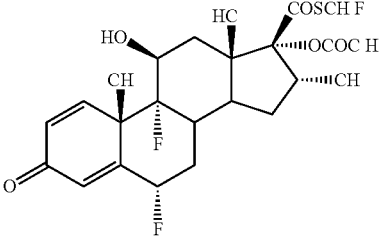<br>S-(fluoromethyl)6α,9-difluoro-11β-17-dihydroxy-16α-methyl-3-oxoandrosta-1,4-diene-17β-carbothioate, 17-propionate | It is practically insoluble in water, freely soluble in dimethyl sulfoxide and dimethylformamide, and slightly soluble in methanol and 95% ethanol. Solubility in Diethylene glycol monoethyl ether is 14.7 mg/ml. | Available as 50 mcg Nasal spray. |

In addition to the above, various other drugs for treating AIDS, Rare Diseases, Neglected diseases such as Tuberculosis, Malaria etc. can also be made into clear, transparent and non hazy solutions by utilizing the vehicle or solvent of the present invention solvent, Diethylene glycol monoethyl ether or other alkyl derivatives. Such solutions can be useful as injections for rapid onset of action when required to provide earliest result into the patient. The solution can also be used for formulation of different dosage forms like capsules, tablets, nasal sprays, gels, topics, liquid oral dosage forms etc. The solutions can also be used for preparation of nano solutions.

EXAMPLES

The following Examples illustrate the invention in detail, which should not be construed as limiting the scope of the invention.

Example 1: Solubility

The solubility of various pharmaceutical actives, belonging to the three classes, referred to hereinbefore in Diethylene glycol monoethyl ether are summarized in Table-III.

TABLE III

The Solubility of various Pharmaceutical Actives in Diethylene Glycol Monoethyl Ether

| Code | Pharmaceutical Active | Solubility in Diethylene Glycol Monoethyl Ether |
|---|---|---|
| Class I: Drugs which are Difficult to Solubilize | | |
| I.1 | Progesterone | 50 mg/ml |
| I.2$_A$ | Nandrolone Decoanate 100 mg/ml | 100 mg/ml |
| I.2$_B$ | Nandrolone Phenyl Propionate | 71.42 mg/ml |
| I.3$_A$ | Testosterone Enanthate | 55.50 mg/ml |
| I.3$_B$ | Testosterone Cypionate | 45.45 mg/ml |
| I.6 | Fulvestrant | 58.80 mg/ml |
| I.7 | Artemether | 100 mg/ml |

TABLE III-continued

The Solubility of various Pharmaceutical Actives in Diethylene Glycol Monoethyl Ether

| Code | Pharmaceutical Active | Solubility in Diethylene Glycol Monoethyl Ether |
|---|---|---|
| I.8 | Arteether | 80 mg/ml |
| I.9 | Haloperidol | 8.30 mg/ml |
| I.10 | Vitamin D3 | 30 mg/ml |
| I.12 | Etoricoxib | 200 mg/ml |
| I.13 | Cyclosporine | 50 mg/ml |
| I.14 | Paclitaxel | 23.80 mg/ml |
| I.15 | Piroxicam | 15 mg/ml |
| Class II: Drugs which have Stability Issues | | |
| II.3 | Artesunate | 100 mg/ml |
| II.9 | Lignocaine | 200 mg/ml |
| II.10 | Azithromycin | 83 mg/ml |
| II.12 | Dicyclomine Hydrocloride | 20 mg/ml |
| II.13 | Paracetamol | 66.66 mg/ml |
| II.16 | Prostaglandin E$_1$ (Alprostadil) | 50 mg/ml |
| II.19 | Pantoprazole | 80 mg/ml |
| II.21 | Etoposide | 30 mg/ml |
| II.22 | Docetaxel | 55 mg/ml |
| II.25 | Voricanozole | 83 mg/ml |
| II.27 | Ibuprofen | 400 mg/ml |
| Class III: Those which are Available in the Form of Suspensions and are very Difficult to be Solubilized into a Solution Form | | |
| III.1 | Prednisolone | 11.11 mg/ml |
| III.2 | Methyl Prednisolone | 30 mg/ml |
| III.4 | Triamcinolone Acetonide | 15 mg/ml |
| III.9 | Aceclofenac | 150 mg/ml |
| III.11 | Terbinafine | 16.66 mg/ml |
| III.21 | Celecoxib | 71.42 mg/ml |
| III.23$_A$ | Brinzolamide | 55.55 mg/ml |
| III.23$_D$ | Loteprednol | 25 mg/ml |
| III.23$_L$ | Nepafenac | 2 mg/ml |
| III.23$_M$ | Betaxolol Hydrochloride | 27.77 mg/ml |

TABLE III-continued

The Solubility of various Pharmaceutical Actives in Diethylene Glycol Monoethyl Ether

| Code | Pharmaceutical Active | Solubility in Diethylene Glycol Monoethyl Ether |
|---|---|---|
| IV.1 | Vinpocetine | 12 mg/ml |
| IV.11 | Loxapine Succinate | 31.25 mg/ml |
| IV.12 | Amilsulpride | 25 mg/ml |
| IV.15 | Olanazapine | 45 mg/ml |
| IV.16 | Fluticasone Propionate | 14.70 mg/ml |

Example 2: Progesterone (I.1)

| Sr. No | Ingredients | Quantity/ml |
|---|---|---|
| 1 | Progesterone | 100 mg |
| 2 | Benzyl Alcohol | 20% |
| 3 | Diethylene Glycol Monoethyl Ether | q.s. up to 1 ml |

The maximum solubility of Progesterone in Diethylene glycol monoethyl ether was found to between 0.1 to 50 mg/ml while its solubility in Benzyl alcohol was found up to 100 mg/ml. Progesterone is dissolved in solution of 20% Benzyl alcohol giving a clear solution and add Diethylene glycol monoethyl ether with constant stirring and make the volume up to 100 ml with Diethylene glycol monoethyl ether. The clear colourless liquid has viscosity of 3.86 cps. This solution is filled in 3 ml clear glass vial.

Similarly, 2 g to 12 g of drug is dissolved in 100 ml Diethylene glycol monoethyl ether to give a clear solution for use in therapeutic concentration as a parenteral form. The same may be filled in vial or ampoules, PFS.

Optionally, it can be mixed with preservative like benzyl alcohol in the range of about 2% to 4% for filling in multi dose container or the Liquid prepared can be used for the preparation of pessaries for vaginal delivery by successfully matrixing with suitable excipients.

Other adjuvant may be used optionally with water in sufficient quantity to keep the solution pellucid as well as physically and chemically stable.

The non aqueous solution can be filled in capsule or aqueous or non aqueous liquid can be employed for their use in other oral delivery system.

Stability Study Data for Progesterone Injection 100 mg/ml:

The stability study of this formulation containing 100 mg/ml Progesterone and tested by the validated method was found to be satisfactory.

The viscosity of the comparator brand is 4.9 cps

Example 3: Nandralone Decanoate (I.2$_A$)

The solubility profile of Nandrolol decanoate with Diethylene glycol monoethylether is about 1 to 100 mg/ml.

| Sr. No. | Name of Ingredients | Qty/ml | Qty/ml | Qty/ml |
|---|---|---|---|---|
| 1 | Nandrolone Decanoate | 100 mg | 25 mg | 25 mg |
| 2 | Benzyl Alcohol | 2% | 2% | 2% |
| 3 | BHA | 1 mg | 1 mg | 0.3 mg |
| 4 | BHT | 1 mg | 1 mg | 0.3 mg |
| 5 | Vitamin E Acetate | 1 mg | 1 mg | 1 mg |
| 6 | Diethylene Glycol Monoethyl Ether | q.s | q.s | q.s |

Weigh accurately Nandrolone Decanoate under cool & dark place & take clean vessel. Add Diethylene glycol monoethyl ether into this and stir vigorously to dissolve Nandrolone Decanoate until a clear solution is obtained. Add BHA, BHT & Vit. E. acetate, stir vigorously to dissolve it in Diethylene glycol monoethyl ether.

Make up the volume up to 100 ml. using Diethylene glycol monoethyl ether. Solution is filtered by 0.45 micron filter 0.22μ & filled in 1 ml clear glass ampoules with nitrogen flushing & stability.

The resultant solution gives a concentration of Nandrolone Decanoate.

The stable solution of Nandrolone Decanoate in the concentration of 25 mg and 100 mg/ml can be prepared which has viscosity of 3.485 cps. as compared to only injection which has more than 19 cps. The new composition solution is painless while administering in the tissues.

Clear solution of Nandrolone decanoate 100 mg/ml injection or 25 mg/ml injection is obtained. The viscosity of this final solution was found about 3.485 cps.

The dispensing & manufacturing process should be completed into cool & dark place because Nandrolone Decanoate is a hormonal drug and sensitive to light, moisture, & Temperature.

Thus, 1 mg to 100 mg of drug injection can be prepared using Diethylene glycol monoethyl ether and may be filled in ampoules or vials.

| Sr. No. | Tests | Specification | Initial | 40° C./ 75% RH/ 1 M | 40° C./ 75% RH/ 2 M | 25° C./ 60% RH/ 3 M | 30° C./ 65% RH/3 M | 40° C./ 75% RH/ 3 M | 25° C./ 60% RH/ 6 M | 30° C./ 65% RH/6 M | 40° C./ 75% RH/6 M | 25° C./ 60% RH/9 M | 30° C./ 65% RH/9 M |
|---|---|---|---|---|---|---|---|---|---|---|---|---|---|
| 1 | Description | | | Clear Colourless Solution | | | | | | | Yellowish Colour Clear | Clear Colourless Solution | |
| 2 | Assay UV (%) | 92.5 to 107.5 | 103.00 | 103.00 | 103.50 | 101.06 | 99.90 | 102.10 | 102.50 | 99.30 | 96.20 | 100.12 | 99.37 |

The preservative like benzyl alcohol, solubilizers and antioxidants added keeps the solution pellucid, physically and chemically stable.

Stability Study Data for Nandrolone Decanoate Injection 100 mg/ml:

| Sr. No. | Tests | Specification | Initial | 40° C./ 75% RH/1 M | 40° C./ 75% RH/2 M | 25° C./60% RH/3 M | 30° C./65% RH/3 M | 40° C./75% RH/3 M | 25° C./60% RH/6 M | 30° C./65% RH/6 M | 40° C./75% RH/6 M |
|---|---|---|---|---|---|---|---|---|---|---|---|
| 1 | Description | | | | | Clear Colourless Solution | | | | | Slight Pale Yellowish Clear |
| 2 | Assay (%) | 90-110 | 100.71 | 102.81 | 102.83 | 102.81 | 101.22 | 101.00 | 99.14 | 99.25 | 98.29 |

Stability Study Data for Nandrolone Decanoate Injection 25 mg/ml:

| Sr. No. | Tests | Specification | Initial | 40° C./75% RH/1 M | 25° C./60% RH/3 M | 30° C./65% RH/3 M | 40° C./75% RH/3 M |
|---|---|---|---|---|---|---|---|
| 1 | Description | | | | Clear Colourless Solution | | |
| 2 | Assay (%) | 90-110 | 101.95 | 101.69 | 103.21 | 102.79 | 101.59 |

The stability study of Nandrolone Decanoate injection of both dose strength 25 mg/ml and 100 mg/ml are found to be in the acceptable range.

Example 4: Testosterone Cypionate (I.3$_B$)

The solubility of testosterone cypionate in Diethylene glycol monoethyl ether was found to be 50 mg/ml with viscosity less than 7 cps.

2.5 g to 5 g of drug is dissolved in 100 ml Diethylene glycol monoethyl ether to give a clear solution.

The stable injections are filled in ampoules or vials or PFS for ready use.

The final concentration can be given to the doctors after filling in ampoules and vials for it therapeutic application to the doctors, for the parenteral application.

The solution may be optionally filled in the desired concentration in caps for oral delivery or for preparing the composition for applying as gel.

The liquid may optionally have preservative like benzyl alcohol in concentration of about 2% to 6% antioxidants in butylated hydroxyl anisole or butylated hydroxy toluene may be added, which keeps the solution pellucid as well as physically and chemically stable.

Example 5: Artemether ((I.7)

| | | Example No. | | |
|---|---|---|---|---|
| Sr. No. | Name of Ingredients | 1 Qty/ml | 2 Qty/ml | 3 Qty/ml |
| 1 | Artemether | 80 mg | 80 mg | 80 mg |
| 2 | Benzyl alcohol | 2% v/v | 2% | 2% |
| 3 | BHA | — | 1 mg | 0.2 mg |
| 4 | BHT | — | 1 mg | 0.2 mg |
| 5 | Vitamin E Acetate | 0.25 mg | 1 mg | 1 mg |
| 6 | Diethylene Glycol Monoethyl Ether | Q.s | Q.s | Q.s |
| 7 | Molecular Sieve for Drying | — | — | 25 mg |

The viscosity of the final solution of Artemether Injection 80 mg/ml was found about 3.322 cps.

4 g to 10 g of drug is dissolved in 100 ml Diethylene glycol monoethyl ether to give a clear solution.

The necessary antioxidants and preservatives like Butylated hydroxyl anisole, Butylated hydroxyl toluene, Tocopherol acetate and Benzyl alcohol is added. The solution is found to be stable and can be easily administered by I.M. or I.V. route for desired therapeutic purpose.

The achieved concentration may be filled in ampoules, PFS or vials to be used by the doctors.

Suitable preservatives like benzyl alcohol and antioxidants like, thioglycerol and ascorbyl palmitate may be optionally added, which keeps the solution pellucid physically and chemically stable.

The final clear solution is filled into clear glass vial of 5 ml volume as well as can be filled into ampoules or prefilled syringes.

Stability Study Data of Artemether Injection 80 mg/ml:

| Sr No. | Test | Initial | 1M/40° C. | 2M/40° C. |
|---|---|---|---|---|
| 1 | Descrpition | | Clear Colourless Solution | |
| 2 | Assay, Limit 90 to 110% | 104.84 | 100.35 | 98 |

The injections can be administered through I.M. or I.V. route

The stability data of Artemether injection prepared using Diethylene glycol monoethyl ether solvent was found in the accepted range.

Example 6: Arteether (I.8)

The solubility range for α, β-Arteether in Diethylene glycol monoethyl ether was observed about 1 to 76.74 mg/ml.

| Sr. No | Name of Ingredient | Qty/ml |
|---|---|---|
| 1 | α, β Arteether | 75 mg |
| 2 | Benzyl alcohol | 4% |
| 3 | Vitamin E Acetate | 1 mg |
| 4 | Diethylene Glycol Monoethyl Ether | q.s |

7.5 g of drug is taken in a flask to dissolve in 100 ml Diethylene glycol monoethyl ether to give therapeutically suitable preservative and antioxidants are added to give clear solution ready to be used as a composition after filtering aseptically in an ampoule or vial for use as injection which can be administered through I.M. and I.V. The viscosity of the liquid is found to be 2.85 cps as compared to oily injection which has more than 39 cps.

Optionally, preservatives like Benzyl alcohol in the concentration from 1% to 10% may be added with adding anti oxidants like Vitamin E acetate, BHA, BHT and other available antioxidants in the acceptable range.

Additionally, adjuvants may be added in pharmaceutically acceptable concentration to stabilize the liquid for its use directly or by matrixing in the suitable excipients to give suitable oral delivery composition.

The final solution of α,β Arteether 75 mg/ml injection have viscosity of about 2.85 cps. It can be packed into vials or 2 ml ampoule or prefilled syringes in therapeutic concentrations and in desired volumes.

As the viscosity is less, same can be administered safely without any pain as compared to presently available oily injection which has viscosity of more than 35 cps Stability Study Data for α,β Arteether 75 mg/ml Injection:

| Sr. No. | Tests | Specification | Initial | 40° C./75% RH/1 M | 40° C./75% RH/ 2 M | 25° C./ 60% RH/ 3 M | 30° C./ 65% RH/ 3 M | 40° C./ 75% RH/ 3 M | 25° C./ 60% RH/6 M | 30° C./ 65% RH/6 M | 40° C./ 75% RH/6 M | 25° C./ 60% RH/9 M | 30° C./ 65% RH/9 M |
|---|---|---|---|---|---|---|---|---|---|---|---|---|---|
| 1 | Description | | | | | Clear colourless solution | | | | | | | |
| 2 | Assay (%) | 90-110 | 101.10 | 100.84 | 100.24 | 101.62 | 100.91 | 98.42 | 98.75 | 101.13 | 101.50 | 99.63 | 99.86 |

Stability study of α,β Arteether 75 mg/ml injection prepared in Diethylene glycol monoethyl ether was performed according to ICH guidelines and all the test were found in acceptable criteria.

Example 7: Etoricoxib (I.12)

Etoricoxib was found to be soluble in Diethylene glycol monoethyl ether in range of 1 to 200 mg/ml.

| Sr. No | Name of Ingredient | Qty/ml |
|---|---|---|
| 1 | Etoricoxib | 90 mg |
| 2 | Benzyl Alcohol | 4% |
| 3 | Diethylene Glycol Monoethyl Ether | q.s |

The same is novel delivery otherwise is not available in market as injections.

1 g to 20 g of drug is dissolved in 100 ml Diethylene glycol monoethyl ether to give a clear solution. Preservative like Benzyl alcohol in varying concentration can be added.

Herein, the therapeutic concentration of drug is prepared in concentration of 90 mg/ml in Diethylene glycol monoethyl ether. It has viscosity 3.70 cps. The injection being less viscous easily syringable and can be easily administered in the tissues through I.M or I.V. route.

The achieved concentration may be useful for its application as injections filled in ampoules, PFS and or filled in hard filled caps/soft gel or suitably compounded as Roll On composition or for dermal delivery to give stable formulation. Other additives may be added to incorporate the same as tablets or for oral liquid with combining in aq liquid with buffering agents and pH adjusting buffers like Tris buffer, acids or alkali.

Stability Study Data of Etoricoxib Injection 90 mg/ml:

| Sr. No. | Tests | Specification | Initial | 40° C./75% RH/1 M | 40° C./75% RH/2 M | 25° C./60% RH/3 M | 30° C./65% RH/3 M | 40° C./75% RH/3 M | 25° C./60% RH/6 M |
|---|---|---|---|---|---|---|---|---|---|
| 1 | Description | | | | Clear Yellow Coloured Solution | | | | |
| 2 | Assay (%) (%) | 90-110% | 100.23 | 99.0 | 100.60 | 101.94 | 102.20 | 102.80 | 100.54 |
| 3 | Impurity (%) | Single: 0.5 Total: 2.0 | | | | Not Determined | | | |

| Sr. No. | 30° C./65% RH/6 M | 40° C./75% RH/6 M | 25° C./60% RH/9 M | 30° C./65% RH/9 M | 25° C./60% RH/12 M | 30° C./65% RH/12 M |
|---|---|---|---|---|---|---|
| 1 | | | Clear Yellow Coloured Solution | | | |
| 2 | 99.52 | 100.23 | 100.24 | 100.63 | 100.63 | 100.55 |
| 3 | Not Determined | | Single: 0.29 Total: 0.69 | Single: 0.298 Total: 0.7 | Single: 0.299 Total: 0.681 | Single: 0.326 Total: 0.724 |

The stability study was carried out for Etoricoxib injection 90 mg/ml and was found to be satisfactory with acceptable. Assay range and no impurities were detected. Thus, the trial of new formulation of Etoricoxib injection 90 mg/ml in Diethylene glycol monoethyl ether indicate the solution stability and ready to use for therapy.

The viscosity of the liquid prepared in Diethylene glycol monoethyl ether is found to be 3.70 cps.

Etoricoxib gel is prepared with composition as below for dermal application.

Composition of Etoricoxib Gel 10 mg

| Sr. No | Ingredients | Qty/ml |
|---|---|---|
| 1 | Etoricoxib IH | 10 mg |
| 2 | Propylene Glycol IP | 250 mg |
| 3 | Diethylene Glycol Monoethyl Ether | 100 mg |
| 4 | Ethanol IP | 200 mg |
| 5 | Tocopheryl Phosphate Hydrolyste (TPM) IH | 10 mg |
| 6 | Sepineo P600 IH | 50 mg |
| 7 | Purified Water IP | Qs up to 1.0 gm |

Stability Study Data of Etoricoxib Gel 10 mg:

| Sr. No | Test | Initial | After 1M 40° C. | After 3M 40° C. |
|---|---|---|---|---|
| 1 | Description | White to off white colour, semisolid, homogeneous | White to off white colour, semisolid, homogeneous viscous | White to off white colour, semisolid, homogeneous viscous Gel. |
| 2 | pH | 4.09 | Not done | Not Done |
| 3 | Viscosity | 48614 cps | Not done | Not Done |
| 4 | Assay, Limits 90 to | 99.83 | 101.06 | 97.33 |
| 5 | Impurity NMT 2% | Not Detected | Single: 0.38% Total: 0.38% | Not Detected |

Example 8: Piroxicam (I.15)

The solubility of Piroxicam in Diethylene glycol monoethyl ether was found to be about 0.1 to 35 mg/ml.

A)

| Sr. No | Ingredient | Qty/ml |
|---|---|---|
| 1 | Piroxicam | 20 mg |
| 2 | Dimethyl Isosorbide | 15% v/v |
| 3 | Diethylene Glycol Monoethyl Ether pH of solution | q.s 4.23 |

B)

| Sr. No | Ingredient | Qty/ml |
|---|---|---|
| 1 | Piroxicam | 20 mg |
| 2 | Tris Buffer | 2.5 mg |
| 3 | Diethylene Glycol Monoethyl Ether pH of solution | q.s 5.71 |

1 g to 5 g of drug is dissolved in 100 ml Diethylene glycol monoethyl ether to give a clear solution to give 10 mg/ml to 50 mg of Piroxicam per ml with the viscosity 3.365 cps.

Further pH of the solution can be brought to alkaline side using alkaliser.

The same may be used as injection after aseptic filtration using 0.22μ filter and filled in ampoules or vials as per therapeutic requirements.

The hard filled or soft gelatin caps can be filled in a suitable concentration for the oral delivery or suitable formulated for the dermal delivery in form of gels or for use as sprays.

Stability Study Data of Piroxicam Injection 20 mg/ml:

| Sr. No. | Test | Initial | 40° C./ 75% RH/ 1M A | 40° C./ 75% RH/ 1M B |
|---|---|---|---|---|
| 1 | Description | Greenish Yellow Colour Liquid | | |
| 2 | Assay, Limit 90% to 110% | 98.78 | 97.52 | 96.28 |
| 3 | Related Substances, Limit NMT 2% | Not Detected | Not Detected | Single: 0.53% Total: 0.72% |

Stability study was performed for new injectable solution of Piroxicam of dose strength 20 mg/ml. It was found to be in acceptable range and the formulation was stable at studied accelerated conditions.

Example 9: Vitamin $D_3$ (I.10)

The solubility of Vitamin $D_3$ was found up to 0.1 to 33.33 mg/ml in Diethylene glycol monoethyl ether.

| Sr. No. | Ingredient | Qty/ml | Qty/ml |
|---|---|---|---|
| 1 | Vitamin $D_3$ | 15 mg | 15 mg |
| 2 | BHA | 1 mg | 1 mg |
| 3 | Vitamin E Acetate | 1 mg | 1 mg |
| 4 | BHT | 1 mg | — |
| 5 | Diethylene Glycol Monoethyl Ether | Q.s. | Q.s |

Weigh accurately 15 mg of Vitamin D3 and add into clean 100 ml glass vessel. Dissolve the drug into Diethylene glycol with addition of Vitamin E acetate, BHA and BHT optionally.

Mix the solution till drug get dissolve to produce final solution. The same is filled aseptically through 0.22µ filter and filled aseptically in syringe, PFS or vials for therapeutic use through I.M. or I.V. route.

The solution thus prepared can be made available as injectables as well as can be used for preparing other dosage forms like filled into capsule when matrixed with other excipients and adjuvants Stability Study Data of Vitamin $D_3$ Injection 15 mg/ml:

| Sr. No | Test | Initial | 1 M 25° C. | 1 M 40° C. | 2 M 25° C. | 2 M 40° C. | 3 M 25° C. | 3 M 40° C. |
|---|---|---|---|---|---|---|---|---|
| 1 | Description | | | Clear Colourless Solution | | | | |
| 2 | Assay, Limit 90% to 110% | 120.62 | 108.48 | 110.33 | 105.46 | 101.26 | 105.90 | 105.90 |

Vitamin D3 Injection 15 mg/ml prepared in Diethylene glycol monoethylether was kept for stability study. The viscosity of it in Diethylene glycol monoethyl ether is 3.13 cps. The results were found to be satisfactory.

Example 10: Paclitaxel (I.14)

| Sr. No. | Ingredients | Trial 1 Qty (ml) | Trial 2 Qty (ml) | Trial 3 Qty (ml) |
|---|---|---|---|---|
| 1 | Paclitaxel | 6 mg | 6 mg | 6 mg |
| 2 | Polysorbate 80 | 0.15 ml | 0.1 ml | 0.1 ml |
| 3 | PEG 400 | 0.15 ml | 0.3 ml | 0.2 ml |
| 4 | Ethanol | 0.4 ml | 0.3 ml | 0.3 ml |
| 5 | Diethylene Glycol Monoethyl Ether | 0.3 ml | 0.1 ml | 0.2 ml |
| | pH of final solution adjusted with acetic acid | 6.85 | 6.17 | 6.26 |

300 mg to 1200 mg of paclitaxel is dissolved in 100 ml Diethylene glycol monoethyl ether to give a clear solution.

The solution is stable and can be administered directly for its therapeutic purpose as injectable form by filling in ampoule or vials.

The same can also be prepared in the concentration of 6 mg/ml which is therapeutically recommended concentrations using above compositions. The solution is clear and limpid. It is further process under nitrogen to filter it aseptically through 0.22µ membrane and filled suitably in ampoules or vials, PFS for multidose applications for use in infusions.

The same can be administered as bolus or slow infusion.

The trial of Paclitaxel injection prepared in Diethylene glycol monoethyl ether was kept for stability study and the formulation was found to be stable. Viscosity of it in Diethylene glycol monoethyl ether was found to be 2.967 cps.

Example 11: Artesunate (II.3)

The solubility of Artesunate in Diethylene glycol monoethyl ether was found to be from 1 to 100 mg/ml.

| Sr. No | Name of Ingredient | Qty/ml |
|---|---|---|
| 1 | Artesunate | 60 mg |
| 2 | Benzyl Alcohol | 2% |
| 3 | Diethylene Glycol Monoethyl Ether | q.s |

5 g to 8 g in acid form of the drug is dissolved in 100 ml Diethylene glycol monoethyl ether to give a clear, therapeutically acceptable concentration solution. Preservative like benzyl alcohol can be added along with antioxidants like Vit E derivatives, thioglycerol or ascorbyl palmitate can be optionally added which keeps the solution pellucid, physically and chemically stable. Same is filtered aseptically under nitrogen through 0.22µ filter and filled in ampoules, PFS or vials as per therapeutic need and further use.

The injection can be administered as slow infusion or as bolus for safe, for I.V. use for therapeutic action.

The solution of Artesunate in therapeutic dose of 60 mg/ml is prepared using Diethylene glycol monoethyl ether by mixing with 2% Benzyl alcohol. This solution of 60 mg/ml prepared is having the viscosity of about 3.466 cps.

Stability Study Data of Artesunate Injection 60 mg/ml:

| Sr. No. | Test | Initial | 1M/ 40° C./ 75% RH | 2M/ 40° C./ 75% RH | 3M/ 40° C./ 75% |
|---|---|---|---|---|---|
| 1 | Description | | Clear Colourless Solution | | |
| 2 | Assay, Limit 90% to 110% | 100.23 | 98.02 | 99.65 | 99.58 |

The stability data of marketed injection and Artesunate injection 60 mg/ml were compared and it was found that the new formulation prepared in Diethylene glycol monoethyl ether were stable.

Example 12: Paracetamol (II.13)

The solubility of Paracetamol was found to be about 1 to 66.6 mg per ml of Diethylene glycol monoethyl ether solvent and when mixed with co-solvent, same is increased to 200 mg/ml for preparation of therapeutic dosage of Paracetamol injection for 1 mg and 225 mg/ml of Paracetamol Injection

| Sr. No. | Packing Details of Product | Ingredients | Qty/ml |
|---|---|---|---|
| 1 | Paracetamol 10 mg/ml (5 ml clear glass vial) For 100 ml infusion | Paracetamol | 10 mg |
| | | Sodium Chloride | 9 mg |
| | | Diethylene Glycol Monoethyl Ether | 5.0% v/v |
| | | Water for injection | q.s |

-continued

| Sr. No. | Packing Details of Product | Ingredients | Qty/ml |
|---|---|---|---|
| 2 | Paracetamol 20 mg/ml (10 ml clear glass vial) For 50 ml infusion | Paracetamol Sodium Chloride Diethylene Glycol Monoethyl Ether Water for injection | 20 mg 9 mg 7.5% v/v q.s |
| 3 | Paracetamol 200 mg/ml | Paracetamol PEG 400 Tris Buffer Diethylene Glycol Monoethyl Ether | 200 mg 15% 2.5 mg q.s |
| 4 | Paracetamol 150 mg/ml | Paracetamol Benzyl Alcohol Diethylene Glycol Monoethyl Ether | 150 mg 2% q.s. | clear solution is obtained. Then, PEG 400 is added into the solution while dissolving the drug Paracetamol. Maintain the temperature 80-85° C., a clear solution is obtained. Then solution is cooled and final volume is make up with Diethylene glycol monoethyl ether in sufficient quantity to give final solution of drug, 200 mg/ml. Filter the solution in 0.22μ filter and fill in 2 ml clear ampoule, 5 ml clear ampoule, 5 ml clear vial as well can be filled in prefilled syringes or multi dose vials.

Similarly, final solution of 100 mg/ml & 150 mg/ml can also be prepared as given above.

The final solutions of Paracetamol containing 150 mg/ml have viscosity about 7.34 cps. This solution can be filled into 2 ml clear ampoule, PFS or in multidose vials.

The solution may be used for parenteral as i.v bolus or infusion or oral purpose after filling in ampoule, vial or in caps forms.

Stability Study Data of Paracetamol Injection 150 mg/ml:

| S. No | Tests | Specification | Initial | 40° C./75% RH/1M | 40° C./75% RH/2M | 25° C./60% RH/3M | 30° C./65% RH/3M | 40° C./75% RH/3M |
|---|---|---|---|---|---|---|---|---|
| 1 | Description | | | | Clear Colourless Solution | | | |
| 2 | Assay (%) | 90-110 | 103.24 | 105.09 | 100.76 | 100.87 | 100.37 | 99.16 |
| 3 | Impurities | 4 Aminophenol- NMT 0.5% Total impurity- NMT 2.0% | 4 Aminophenol- ND Total impurity - ND | 4 Aminophenol- ND Total impurity - ND | 4 Aminophenol- ND Total impurity - ND | 4 Aminophenol- ND Total impurity - 0.28% | 4 Aminophenol- ND Total impurity - 0.34% | 4 Aminophenol- ND Total impurity - 0.128% |

| S. No | 25° C./60% RH/6M | 30° C./65% RH/6M | 40° C./75% RH/6M | 25° C./60% RH/9M | 30° C./65% RH/9M |
|---|---|---|---|---|---|
| 1 | | Clear Colourless Solution | | | |
| 2 | 101.94 | 99.30 | 98.99 | 101.18 | 99.75 |
| 3 | 4 Aminophenol- ND Total impurity - 0.023% | 4 Aminophenol- ND Total impurity - 0.023% | 4 Aminophenol- ND Total impurity - 0.57% | 4 Aminophenol- ND Total impurity - ND | 4 Aminophenol- ND Total impurity - ND |

-continued

| Sr. No. | Packing Details of Product | Ingredients | Qty/ml |
|---|---|---|---|
| 5 | Paracetamol 100 mg/ml | Paracetamol Benzyl Alcohol Diethylene Glycol Monoethyl Ether | 100 mg 2% q.s. |

For Sr. No. 1 & 2:

In a suitable vessel, Paracetamol in required quantity is dissolved in Diethylene glycol monoethyl ether with stirring simultaneously. In another beaker, sodium chloride is added in water for injection. Then, both the solution are mixed together and final volume is make up with water for injection to give final solution of 10 mg/ml and 20 mg/ml respectively. The pH of final solution containing dose strength 10 mg/ml is 5.78 and same for 20 mg/ml is 5.67 respectively.

As the viscosity is very less, the solution can be infused slowly 1 g to 20 g of paracetamol is dissolved in 100 ml Diethylene glycol monoethyl ether to give a clear solution with addition of suitable preservative like Benzyl alcohol and adjusting pH with suitable buffering agent like Tris buffer.

For Sr. No. 3:

Diethylene glycol monoethyl ether is heated up to 80° C. in suitable vessel and Tris buffer is added with stirring till a The stability study for Paracetamol Injection 150 mg/ml was performed and was found to be in acceptable range and is satisfactory when compared with the available marketed product of the same dose strength.

Example 13: Dicyclomine Hydrochloride (II.12)+Diclofenac Sodium Injection

The solubility of Dicyclomine was about 0.1 to 20 mg/ml and of Diclofenac up to 0.1 to 133 mg/ml in Diethylene glycol monoethyl ether.

Following example is cited to study combination of 20 mg Dicyclomine HCl with 50 mg Diclofenac Sodium using the inventive process which is giving stable injections. Same is easily syringable and administered in the tissues without causing pain. Viscosity of the solution in Diethylene glycol monoethyl ether is 5.022 cps.

| | | Example No. | | |
|---|---|---|---|---|
| Sr. No. | Ingredients | 1 Qty/ml | 2 Qty/ml | 3 Qty/ml |
| 1 | Dicyclomine Hydrochloride | 20 mg | 20 mg | 20 mg |
| 2 | Diclofenac Sodium | 50 mg | 50 mg | 50 mg |

-continued

| Sr. No. | Ingredients | 1 Qty/ml | 2 Qty/ml | 3 Qty/ml |
|---|---|---|---|---|
| 3 | Diethylene Glycol Monoethyl Ether | Q.s | 60% | 60% |
| 4 | 0.1M NaOH | Q.s | Q.s | — |
| 5 | Sodium Metabisulphite | — | 1 mg | 1 mg |
| 6 | WFI | — | Q.s | Q.s |
| 7 | Benzyl alcohol | — | 2% | 2% |

The Stability study data given below for Diclofenac (50 mg)+Dicyclomine HCl (20 mg) injection is of optimized example Nos. 2 and 3.

| Sr. No. | Test | Initial | 40° C./75% RH/1M | 40° C./75% RH/2M | 40° C./75% RH/3M |
|---|---|---|---|---|---|
| 1 | Description | Clear Transparent Liquid | Clear Transparent Liquid | Clear Transparent Liquid | Clear Transparent Liquid |
| 2 | Assay of Diclofenac, Limit 90 to | 99.4 | 99.1 | 98.7 | 100.6 |
| 3 | Assay of Dicyclomine hydrochloride Limit 90 to 110% | 101.2 | 100.7 | 99.9 | 98.6 |
| 4 | Impurity, NMT 2% | Not detected | 0.01 | 0.01 | 0.01 |

The combination of Diclofenac (50 mg) and Dicyclomine HCl (20 mg) injection were kept for stability study as per ICH guidelines and were found to be stable with all the tests in acceptable criteria.

Example 14: Pantoprazole Sodium Injection (II.19)

Pantoprazole Sodium is soluble in Diethylene glycol monoethyl ether from 1 to 80 mg/ml.

| Sr. No. | Examples Name of Ingredients | 1 Qty/ml | 2 Qty/ml | 3 Qty/ml |
|---|---|---|---|---|
| 1 | Pantoprazole Sodium | 40 mg | 40 mg | 40 mg |
| 2 | BHA | 1 mg | 1 mg | 0.3 mg |
| 3 | Benzyl Alcohol | 2% | 2% | 2% |
| 4 | BHT | — | 1 mg | 0.3 mg |
| 5 | Diethylene Glycol Monoethyl Ether | q.s | q.s | q.s |

In the current example, 40 mg/ml of Pantoprazole Sodium stable injection are prepared by dissolving preferably sodium or its acid salts by taking 4 g of the drug in mixture of Diethylene glycol monoethyl ether and Benzyl alcohol in 100 ml vessel, BHA i.e, Butylated Hydroxy Anisole (in Example 1) or in combination of BHA and BHT i.e, Butylated Hydroxy Toulene (can be added as antioxidant/preservative in Example 2 & 3) or Thioglycerol is added into this mixture. Finally, the total volume is make up with Diethylene glycol monoethyl ether in sufficient quantity to give clear colorless solution which is filtered and filled in vials, PFS or ampoules.

It is preferred to bubble the liquid with nitrogen and filled under nitrogen. The viscosity of Pantoprazole Sodium injection 40 mg/ml was found to be 3.816 cps.

Similarly, 1 g to 10 g of drug in acid form (Pantaprazole Sodium) is dissolved in 100 ml Diethylene glycol monoethyl ether to give a clear solution and compounded as above.

The therapeutic concentration is suitably filled in ampoules, PFS or vials for its direct use after, filling aseptically through 0.22μ and filling suitable antioxidants and preservatives are added to the liquid.

Alternatively, Water for injection q.s and preservative like Benzyl alcohol 2 to 4%, buffer agents may be optionally added to maintain pH more than 8 i.e. 9.5 to 11.5 which keeps the solution pellucid, physically and chemically stable.

Stability Study Data of Pantaprazole Sodium Injection 40 mg/ml:

| Sr. No | Test | Initial | 1M/ 40° C./ 75% RH | 3M/ 25° C./ 60% RH | 3M/ 40° C./ 75% RH |
|---|---|---|---|---|---|
| 1 | Description | Slight Yellow Colour Solution | | | |
| 2 | Assay, Limit 90 to 110% | 101.36% | 95.12% | 98.43% | 95.94% |
| 3 | Impurities, single NMT 1% Total NMT | Single: 0.003% Total: 0.05% | Single: 0.42% Total: 0.55% | Single: 0.04% Total: 0.08% | Single: 0.62% Total: 0.81% |

The stability study of Pantaprazole Sodium injection 40 mg/ml was found to be satisfactory. Viscosity of the solution in Diethylene glycol monoethyl ether is 3.816 cps.

Example 15: Voriconazole (II.25)

The solubility profile of Voriconazole is found to be from 0.1 to 83 mg/ml in Diethylene glycol monoethyl ether.

| Sr. No. | Ingredient | Qty/ml |
|---|---|---|
| 1 | Voriconazole | 10 mg |
| 2 | Diethylene Glycol Monoethyl Ether | 0.5 ml |
| 3 | Water For Injection | Q.s |

1 g to 10 g of drug is dissolved in 100 ml Diethylene glycol monoethyl ether to give a physically clear solution. Viscosity of the solution in Diethylene glycol monoethyl ether is 2.977 cps.

The finally achieved therapeutic concentration may be employed for parenteral use as slow infusion or solution so preferred can be used to prepare oral delivery suitably formulated with adjuvants, additives and preservatives for treating the mammals for therapeutic purpose.

Example 16: Ibuprofen (II.27)

The solubility of Ibuprofen in Diethylene glycol monoethyl ether was found to be about 500 mg/ml.

The following formulation can be prepared using Diethylene glycol monoethyl ether:

| Sr. No. | Ingredient | Qty/ml | Qty/ml |
|---|---|---|---|
| 1 | Ibuprofen | 400 mg | 200 mg |
| 2 | Diethylene Glycol Monoethyl Ether | q.s to 1 ml | q.s to 1 ml |

10 g to 50 g of Ibuprofen is taken in a vessel and dissolved in Diethylene glycol monoethyl ether to give final solution. The therapeutically available and marketed 400 mg/ml and 200 mg/ml of Ibuprofen injectable solution were prepared using the invention solvent which was found to be colorless and physically stable in nature and the viscosity in Diethylene glycol monoethyl ether is 6.76 cps and 4.51 cps respectively.

Example 17: Methyl Prednisolone (III.2)

The solubility of Methyl Prednisolone was found to be about 1 to 30 mg/ml in Diethylene glycol monoethyl ether and about 130 mg/ml in benzyl alcohol. Hence, formulations were prepared using co-solvents.

| Sr. No | Ingredients | Qty/ml | Qty/100 ml |
|---|---|---|---|
| | Example 1: | | |
| 1 | Methyl Prednisolone | 40 mg | 4 g |
| 2 | Benzyl Alcohol | 10% v/v | 10 ml |
| 3 | Dimethyl Isosorbide | 2% v/v | 2 ml |
| 4 | Diethylene Glycol Monoethyl Ether | q.s | q.s |
| | Example 2: | | |
| 1 | Methyl Prednisolone | 40 mg | 4 g |
| 2 | Benzyl Alcohol | 10% v/v | 10 ml |
| 3 | Dimethyl Isosorbide | 2% v/v | 2 ml |
| 4 | Vitamin E | 1 mg | 100 mg |

-continued

| Sr. No | Ingredients | Qty/ml | Qty/100 ml |
|---|---|---|---|
| 5 | Diethylene Glycol Monoethyl Ether | q.s | q.s |
| | Example 3: | | |
| 1 | Methyl Prednisolone | 40 mg | 4 g |
| 2 | Benzyl Alcohol | 10% v/v | 10 ml |
| 3 | Dimethyl Isosorbide | 2% v/v | 2 ml |
| 4 | BHA (Butylated Hydroanisole) | 1 mg | 100 mg |
| 5 | Diethylene Glycol Monoethyl Ether | q.s | q.s |

Example 1

In mixture of Diethylene glycol monoethyl ether, benzyl alcohol and Dimethyl isosorbide in a vessel, Methyl prednisolone is dissolved and stirs well to get a clear colorless solution. Make up the final volume with Diethylene glycol monoethyl ether

Example 2/3

A mixture of Diethylene glycol monoethyl ether, Benzyl alcohol and Dimethyl isosorbide is prepared in a vessel. Methyl prednisolone is dissolved and stirs well to get a clear colorless solution. Then Vitamin E in example 2 and BHA (butylated hydroxy anisole) in example 3 is added into the solution respectively and make up the final volume using Diethylene glycol monoethyl ether.

The viscosity of Methyl Prednisolone Injection 40 mg/ml was measured about 3.70 cps which is lesser than the available marketed products.

Similarly, 2 g to 10 g of drug is dissolved in 100 ml Diethylene glycol monoethyl ether to give a clear solution for therapeutic use as injectable. Preservative like benzyl alcohol at 2 to 10% may be added with antioxidants like Thioglycerol, Sodium Ascorbate, Tocopherols are added in the desired concentration to give clear, pellucid liquid which is physically and chemically stable.

After making of volume for the desired strength the liquid is filtered aseptically through 0.22μ filter and filled in ampoules, PFS, vials with nitrogen bubbling.

Above solutions are found to be stable and yields a comfortably syringable, low viscosity solution which can be easily administered in the tissues without causing pain.

Stability Study Data of Methyl Prednisolone Injection 40 mg/ml:

| Sr. No | Test | Specification | Initial | 1M 40° C. | 3M 40° C. | 3M 25° C. | 6M 25° C. | 6M 40° C. |
|---|---|---|---|---|---|---|---|---|
| 1 | Description | Clear Colourless Solution | | | | | | |
| 2 | Assay IH (HPLC) | 90-110 | 99.08 | 101.49 | 98.40% | 98.39 | 99.68 | 98.53 |
| 3 | RS | Single = 1.%0 | Single = 0.09% | Single = 0.33% | Single = 0.935% | Single = 0.444% | Single = 0.38% | Single = 0.56% |
| | | Total = 2.0% | Total = 0.09% | Total = 0.52% | Total = 1.67% | Total 0.78% | Total = 0.63% | Total = 0.85% |

Stability study of Methyl Prednisolone Injection 40 mg/ml was performed and result was obtained in the acceptable range.

Example 18: Triamcinolone Acetonide (III.4)

The solubility of Triamcinolone Acetonide was found up to 1 to 15 mg/ml in Diethylene glycol monoethyl ether.

| Sr. No | Ingredients | Qty/ml | Qty/ml |
|---|---|---|---|
| 1 | Triamcinolone Acetonide | 10 mg | 20 mg |
| 2 | Benzyl Alcohol | 0.8% | 0.8% |
| 3 | Diethylene Glycol Monoethyl Ether | q.s | q.s |

While preparation of injection, Diethylene glycol monoethyl ether & Benzyl alcohol are mixed well in a suitable vessel. Triamcinolone acetonide is added in required dose strength (i.e 1 gm to 5 gm) and stirred till a clear solution is obtained. Final volume of this solution is made up with Diethylene glycol monoethyl ether. The solution is filtered aseptically through 0.22μ filter and filled in ampoules, PFS and vials. Optionally, benzyl alcohol can be added which keeps the solution pellucid as well as physically and chemically stable.

The viscosity of Triamcinolone injection 20 mg/ml was measured about 3.036 cps.

Stability Study Data of Triamcinolone Acetonide Injection 20 mg/ml:

| Sr. No. | Tests | Initial | 40° C./75% RH/1M | 25° C./60% RH/3M | 30° C./65% RH/3M | 40° C./75% RH/3M | 25° C./60% RH/6M | 30° C./65% RH/6M | 40° C./75% RH/6M |
|---|---|---|---|---|---|---|---|---|---|
| 1 | Description | Clear colourless, solution | Complies | Complies | Complies | Complies | Complies | Complies | Complies |
| 2 | Assay (90%-110%) | 103.97% | 98.52% | 99.93% | 99.79% | 99.83% | 99.96% | 98.45% | 98.87% |
| 3 | Impurities; single NMT 1% Total impurities NMT 2% | Single = 0.12% Total = 0.12% | Single = 0.29% Total = 0.52% | Single = 0.62% Total = 0.84% | Single = 0.52% Total = 0.80% | Single = 0.42% Total = 0.71% | Single = 0.32% Total = 0.64% | Single = 0.28% Total = 0.63% | Single = 0.19% Total = 0.54% |

Stability Study Data of Triamcinolone Acetonide Injection 10 mg/ml:

| Sr. No. | Tests | Initial | 40° C./75% RH 1M | 40° C./75% RH/2M | 25° C./60% RH/3M | 40° C./75% RH/3M | 25° C./60% RH/6M | 40° C./75% RH/6M | 25° C./60% RH/9M |
|---|---|---|---|---|---|---|---|---|---|
| 1 | Description | Clear colorless solution | Complies | Complies | Complies | Complies | Complies | Complies | Complies |
| 2 | Assay (90%-110%) | 101.30% | 101.88% | 101.58% | 101.40% | 98.53% | 98.34% | 96.77% | 97.97% |
| 3 | Impurities; single NMT 1% Total impurities NMT 2% | ND | Single = 0.291% Total = 0.592% | Single = 0.07% Total = 0.21% | Single = 0.24% Total = 0.37% | Single = 0.40% Total = 0.56% | Single = 0.12% Total = 0.22% | Single = 0.33% Total = 0.76% | Single = 0.16% Total = 0.40% |

The stability study of both the dose strength 10 mg/ml and 20 mg/ml of Triamcinolone acetonide injection was found to be satisfactory as per ICH guidelines.

Example 19: Aceclofenac (III.9)

The solubility profile of aceclofenac in Diethylene glycol monoethyl ether was observed up to 1 to 160 mg/ml.

| Sr no. | Ingredient | Qty/ml |
|---|---|---|
| | Example 1: | |
| 1 | Aceclofenac | 150 mg |
| 2 | Trisodium citrate aqeous solution 30% (pH = 4.57) | q.s |
| 3 | Diethylene Glycol Monoethyl Ether | q.s |
| | Example 2: | |
| 1 | Aceclofenac | 150 mg |
| 2 | Benzyl alcohol | 2% |
| 3 | Triss Buffer 30% aqeous solution | 0.026 ml |
| 4 | Diethylene Glycol Monoethyl Ether | q.s |
| | Example 3: | |
| 1 | Aceclofenac | 150 mg |
| 2 | Benzyl Alcohol | 2% |
| 3 | Tris buffer | 8 mg |
| 4 | Diethylene Glycol Monoethyl Ether | q.s |
| | Example 4: | |
| 1 | Aceclofenac | 150 mg |
| 2 | Dimethyl Isosorbide | 5% |
| 3 | Diethylene Glycol Monoethyl Ether | q.s |

5 g to 16 g of drug is dissolved in 100 ml Diethylene glycol monoethyl ether with other excipients as above to give therapeutically acceptable stable clear solution liquid.

The same may be used therapeutically after aseptically filtering and filling in ampoule, PFS or vials with use of suitable preservative and antioxidants like benzyl alcohol, other alcohols and butylated hydroxyl anisole, sodium metabisulphite, thioacetamide.

Alternatively for an aqueous injection, preservative like benzyl alcohol 2 to 4%, buffer agents and pH adjusting agents like NaOH or HCl may be added which keeps the solution pellucid, physically and chemically stable.

The viscosity of final solution containing Aceclofenac 150 mg/ml was found about 5.11 cps.

Stability Study Data of Aceclofenac 150 mg/ml Injection:

| Sr. No | Parameter | Specification | Initial | 1M/40° C./ 75% RH | 3M/25° C./ 60% RH | 3M/40° C./ 75% RH | 6M/40° C./ 75% RH | 6M/25° C./ 60% RH | 9M/25° C./ 60% RH | 12M/25° C./ 60% RH |
|---|---|---|---|---|---|---|---|---|---|---|
| 1 | Description | Light yellow coloured, clear liquid fill in amber coloured 1 ml glass ampoules. | Complies | Complies | Complies | Complies | Complies | Complies | Complies | Complies |
| 2 | Assay (By UV) Aceclofenac | (90%-110%) | 103.25% | 102.15% | 102.90% | 102% | 101.8% | 102.8% | 102.41% | 98.25% |
| 3 | Related Substance | Diclofenac impurity NMT 5.0% | ND | 0.26% | 0.23% | 0.57% | 1.25% | 0.57% | 0.70% | 0.70% |
| | | Single unknown impurity NMT 1.0% | ND | ND | ND | ND | ND | ND | ND | ND |
| | | Total unknown impurity NMT 2.0% | ND | ND | ND | ND | ND | ND | ND | ND |

The stability study of Aceclofenac Injection 150 mg/ml was found to be in acceptable criteria. The injectable formulation of Aceclofenac in dose strength 150 mg/ml was found to be stable. As the viscosity of the liquid is less it is easily syringable and administered in the tissues without causing pain.

Example 20: Nepafenac Eye Drops 0.1% (III.23$_B$)

The solubility of Nepafenac in Diethylene glycol monoethyl ether was found to be up to 2 mg/ml.

| Sr. No. | Ingredient | Qty/ml |
|---|---|---|
| 1 | Nepafenac | 0.1% |
| 2 | Sodium Chloride | 0.8% |
| 3 | Benzyl Alkonium Chloride | 0.05% |
| 4 | Diethylene Glycol Monoethyl Ether | 50% |
| 5 | Water for Injecton | Q.s |
| 6 | Sodium Hydroxide (1N) | To adjust pH 7.37 |

The viscosity of Nepafenac eye drop prepared by using Diethylene glycol monoethyl ether was found to be 4.137 cps. It was kept for stability study at 40° C.

Stability Study Data of Nepafenac Eye Drops 0.1%:

| Sr. No. | Tests | Specification | Initial | 40° C./75% RH/1M | 25° C./60% RH/3M | 30° C./65% RH/3M | 40° C./75% RH/3M |
|---|---|---|---|---|---|---|---|
| 1 | Description | | | Yellow Coloured Clear Solution | | | |
| 2 | Assay (Glass vial) | 90-110% | 102.18% | 103.29% | 103.58% | 102.21% | 98.64% |
| 3 | Impurity (Glass vial) | Single: NMT 1.0% Total impurity: NMT 2.0% | Single: 0.11% Total: 0.17% | Single: 0.39% Total: 0.39% | Single: 0.39% Total: 0.39% | Single: 0.39% Total: 0.39% | Single: 0.39% Total: 0.39% |

The formulation examples described herein and which is containing Diethylene glycol mono ethyl ether as solvent can also be used for prepare other drug delivery like preparing oral delivery systems, dermal, delivery systems by filling in as roll on gels or creams and for otic delivery systems like drops or filling in capsules for rectal delivery or other delivery systems as stated in the description.

Oral delivery like filing the liquid directly in to Hard fill capsule with band sealing. Eg 30 mg to 120 mg of Etoricoxib filled in HFC.

It can also be mixed with PEGs and oils or it derivatives to fill in soft gelatin capsules.

Paracetamol liquid, Dilcofeneac liquid, Acelcofenac liquid prepared in Dietheyne glycol monoethyl ether can be employed for filling in soft gelatin capsules for rectal deliveries.

The Liquid gels of antifungal agents like Azole derivatives, Flucanzole, Ticonazole can be prepared for vaginal deliveries.

Drugs like Lignocaine, Prilocaine can be prepared in Diethyleneglycol monoethyl ether can be incorporated in spray delivery systems for treating erectile dysfunction.

Drugs like Amlodipine, Nifedipine can be solubilized in Diethyleneglycol monoethyl ether and sprayed in the granulation of tablet matrix containing starch, lactose, stearates and compressed in to tablets.

Dermal delivery of gels like Etoricoxib is prepared with other gel matrices to prepare Gels for dermal application for faster onset of pharmacological action.

Drug solutions like Aceclofenac solution prepared in Diethylene glycol monoethyl ether can also be prepared for preparing the Roll on for dermal delivery.

The solution can further be used for preparing Tulles by appropriately mixing the drug solution with various PEGS sprayed on waxes like wool fat, PEG 4000, 6000 etc for dermal application in pain managements, (ex Aceclofenac, NSAIDs, Cox 2 inhibiots etc)

Tioconazole Gel 6.5%

| Sr. No | Ingredients | Spec | Rationale | Qty Gm/mg |
|---|---|---|---|---|
| 1 | Tioconazole | BP | Active | 65.0 |
| 2 | Carbomer-940 (Acrypol-940) | USP | Gelling agent | 11 |
| 3 | Propylene Glycol | IP | Gel base | 804 |
| 4 | Di ethylene glycol mono ethyl ether | BP | Solubilser | 120 |

Spray:

| Lignocaine | 8.82% |
|---|---|
| Prilocaine | 2.94% |
| Propellent HFA | 58.83% |
| Diethyleneglycol monoethyl ether | 29.41% |

Acute Eye Irritation/Corrosion Test for Diethylene Glycol Monoethyl Ether (Transcutol HP) in Rabbits
Test Item: Transcutol HP
Diluted with: Water for injection
Test System: Rabbits (New Zealand White)
Total No. of Animals: 6 animals for initial test
    12 animals for confirmatory test
No. of groups: 06
Study Design:

| Sr. No | Group | Volume (ml/animal) | Route | Concentration (%) | Total No. of Animals For Initial test | Total No. of Animals For confirmatory test |
|---|---|---|---|---|---|---|
| 1 | 1 | 0.1 | Intra Occular | 2% | 1 | 2 |
| 2 | 2 | 0.1 | Intra Occular | 20% | 1 | 2 |
| 3 | 3 | 0.1 | Intra Occular | 40% | 1 | 2 |
| 4 | 4 | 0.1 | Intra Occular | 60% | 1 | 2 |
| 5 | 5 | 0.1 | Intra Occular | 80% | 1 | 2 |
| 6 | 6 | 0.1 | Intra Occular | 100% | 1 | 2 |

Summary:
Initial Test:

Initial test is carried out by using one animal per group. After dosing animals were observed for irritation at 1, 24, 48, and 72 hours There is no test item related effects were observed during first hour in all the animals of first three groups. Mild irritation was observed in group 4 and 5 animals. Group 6 animal showed moderate irritation and more severity when compared to the group 4 and group 5 animals.

Irrigation was carried out after 24 hrs from the treatment and the animals are again observed for symptoms of toxicity.

During 24 hr observation, all the animals are appeared normal except group 6 animal which was showed mild irritation including Chemosis and Lacrimation. Mild conjunctivitis was also observed.

Depending up on the observations made from the initial test and there was no corrosion effect was observed, hence we proceeded for the confirmatory test.

Confirmatory Test:

Confirmatory test is carried out by using two animals per group. After dosing animals were observed at 1, 24, 48, and 72 hours for toxicity.

The dosing methodology and irrigation procedure was same as mentioned in the initial test and the observations were found as follows:

During 1 hr observations, there is no test item related effects were observed in all the animals of first three groups.

Mild irritation was observed in group 4 and group 5 animals.

One animal from the group 6 was showed severe irritation when observed after 1 hr from the dosing and the other animal also showed irritation but the severity was less when compared with the previous animal.

During 24 hr observation, animals from group 1 to group 3 were normal and there is no irritation was observed in all the animals.

Animals from group 4 and group 5 were showed mild irritation including Chemosis, lacrimation and mild pupillary constriction.

Group 6 animals were suffered with severe irritation and the symptoms includes Chemosis, lacrimation, conjunctivitis, pupillary constriction. The corneal reflex and Iris were normal in all the animals.

The above mentioned observations were lasts for 48 hrs.

Summary:

In summary, all the above mentioned observations, the test item Transcutol is not showing any ocular toxicity up to 80% of concentration. But, the test item Transcutol, may irritant but not corrosive, at the concentration of 100% when administered intra occularly.

Further, when performing Intramuscular, Intravenous and Intraocular studies, Diethyelene glycol monoethyl ether was found to be safe and non toxic.

Protocol:

Pain Assessment Model Study:

Measurement of Pain Sensitivity (Threshold) at Injection Site in Wistar Rats by Intravenous Route & Intramuscular Route The pain assessment model study was carried out on two representative drugs from each class prepared as per application. This study was performed to prove that the injectables prepared by this solvent are painless and less viscous when compared to the respective marketed products as a reference.

The following procedure was carried out to check pain assessment of new formulation against the marketed products:

Objective:

To evaluate pain sensitivity (threshold) at injection site by Pressure application measurement method and comparison with control.

Test Injections: Different injectable formulations (2 drugs from each group of class I, II and III)

Reference Injections: Marketed formulations w.r.t each group of class I, II, and III.

Species used for the study: Wistar rats

No of animals used during different route I.M & I.V individually:

The total number of 18 animals will be divided in to 3 groups containing 6 animals (3M+3F) per group.

Study Design:

The following table are given as study design as pain assessment study through I.V as well I.M route

TABLE A

| Sr. No | Group | Dose (in mg/kg) | Dose (in mL/kg) | Route | Duration of treatment | No. of animals |
|---|---|---|---|---|---|---|
| 1 | Negative control (Water for Injection) | $N1_{IV}$ | $N2_{IV}$ | IV | Single dose | 6 (3M + 3F) |
| 2 | Reference Injection | $R1_{IV}$ | $R2_{IV}$ | IV | Single dose | 6 (3M + 3F) |
| 3 | Test Injection | $T1_{IV}$ | $T2_{IV}$ | IV | Single dose | 6 (3M + 3F) |

TABLE B

| Sr. No | Group | Dose (in mg/kg) | Dose (in mL/kg) | Route | Duration of treatment | No. of animals |
|---|---|---|---|---|---|---|
| 1 | Negative control (Water for Injection) | $N1_{IM}$ | $N2_{IM}$ | IM | Single close | 6 (3M + 3F) |
| 2 | Reference Injection | $R1_{IM}$ | $R2_{IM}$ | IM | Single dose | 6 (3M + 3F) |
| 3 | Test Injection | $T1_{IM}$ | $T2_{IM}$ | IM | Single dose | 6 (3M + 3F) |

Rationale of the Study:

The Pressure Application Measurement (PAM) device is a novel, easy-to-use tool for measuring mechanical pain threshold in experimental pain hypersensitivity models in rodents.

The PAM applies a quantifiable force for direct stimulation of the injection site and automatic readout of the animal response.

The operator simply wears a special force sensor on thumb and measures the force which elicits the animal response (normally, limb withdrawal) as shown in FIG. 1.

Experimental Procedure:

After administration of Negative control, Reference item and test item by intravenous route/intramuscular route mark will be made at injection site so that every time the pain sensitivity will be measure same site by using transducer/applicator.

Transducer placed at injected site and gradually increases the pressure at peak force elicit the animal response and the Transducer/applicator measures the force which elicits the animal response (normally, limb withdrawal).

Force sensor pass the signals of application force, withdrawal force and duration of highest peak force applied at injected site will be record in compact PAM controller.

Pain sensitivity will be measure in control, reference and test groups Immediately (within one minute after injection), 5 min, 10 min, 20 min, 1 hr, 2 hr, 4 hr, 8 hr, 12 hr and 24 hrs after injection.

Pain sensitivity will be measure in control, reference and treated groups will be compared and difference calculated by using SAS System 8.2.

Results: The following parameters are observed to evaluate the pain assessment value for the test items .vs. reference item:
- body weights;
- Nature, Severity and Duration of pain sensitivity (whether reversible or not);
- Pain sensitivity potentials of control, reference and test item statistical treatment of results, where appropriate as below
- Alternatively other models are also adopted to assess the pain in suitable animal model.
- The results indicated that though not very significant reductions in pain in the animals, the prepared injection using diethyleneglycol monoethyl ether exhibits comparatively less pain against following reference injections.
- It may be concluded logically with prudent scientific judgments that with a large body surface in human as compared animals, the perception of pain will be much lesser when similar injections are injected in human tissues and thus the injections prepared using Diethyelene glycol monoethyl ether will be beneficial for the parenteral purpose.

Summary:

From the studies of viscosity for various formulations prepared in diethyele glycol mono ethyl ether, it is imminent that the formulations are easily drawable in the syringe and can be easily administered in the tissues in the required volume without causing pain at the site of injection.

Following injections are tested against the marketed formulation:
1. Paracetamol injection prepared in Diethyelene glycol monoethyl ether against Fabrinil
2. Triamcinolone Acetonide injection in diethylene glycol monoethyl ether against Kenacort.
3. Methyl Prednisolone Acetate injection in Diethyele glycol monoethyl ether against Depo Medrol.
4. Nandrolone Decanoate injection in Diethyele glycol monoethyl ether against Deca Durabolin.
5. Progesterone injection in Diethyele glycol monoethyl ether against Susten 100.
6. Pantaprazole Sodium injection Diethyele glycol monoethyl ether against Pentodec.

Measurement of Pain Sensitivity (Threshold) at Triamcinolone Acetonide Injection Site in Wistar Rats by Intramuscular Route The aim of the study is to evaluate pain sensitivity at Triamcinolone acetonide injection site and comparison with reference

Details of Test System:

| Species | Rat (Wistar) |
|---|---|
| Animal age | 6-8 weeks |
| Number of Animals | The total number of 8 animals divided into 2 groups containing 4 animals (2M + 2F) per gorup. |

Study Design:

| S. No. | Group | Dose (in g/kg) | Dose (in L/KG) | Route | Duration of treatment | No. of animals |
|---|---|---|---|---|---|---|
| 1 | Reference item (Kenacort) | 7.2 | 0.1 | IM | Single dose | 4 (2M + 2F) |
| 2 | Test item (Triamcinolone acetonide injection) | 7.2 | 0.1 | IM | Single dose | 4 (2M + 2F) |

Experimental Procedure: After administration of test and reference item by intramuscular routemark will be made at injection site so that every time the pain sensitivity will be observed same site.

Results: There were no significant pain sensitivity observed at Triamcinolone acetonide injected site compared with Kenacort at 15, 30 Min, 1, 2, 4 hrs. Kenacort injected animals observed with slightly higher pain compared with Triamcinolone acetonide injection.

Measurement of Pain Sensitivity (Threshold) at Progesterone Injection Site in Wistar Rats by Intramuscular Route The aim of the study is to evaluate pain sensitivity at Progesterone injection site and comparison with reference

Details of Test System:

| Species | Rat (Wistar) |
|---|---|
| Animal age | 6-8 weeks |
| Number of Animals | The total number of 8 animals divided into 2 groups containing 4 animals (2M + 2F) per group. |

Study Design:

| S. No | Group | Dose (in g/kg) | Dose (in L/KG) | Route | Duration of treatment | No. of animals |
|---|---|---|---|---|---|---|
| 1 | Reference item (SUSTEN100) | 0.9 | 0.009 | IM | Single dose | 4 (2M + 2F) |
| 2 | Test item (Progesterone injection) | 0.9 | 0.009 | IM | Single dose | 4 (2M + 2F) |

Experimental Procedure: After administration of test and reference item by intramuscular route mark will be made at injection site so that every time the pain sensitivity will be observed same site.

Results: There were no significant pain sensitivity observed at Progesterone injected site compared with SUSTEN100 at 15, 30 Min, 1, 2, 4 hrs. SUSTEN100 injected animals observed with slightly higher pain compared with Progesterone injection.

Measurement of Pain Sensitivity (Threshold) at Nandrolone Decanoate Injection Site in Wistar Rats by Intramuscular Route The aim of the study is to evaluate pain sensitivity at Nandrolone Decanoate injection site and comparison with reference

| Details of Test System: | |
|---|---|
| Species | Rat (Wistar) |
| Animal age | 6-8 weeks |
| Number of Animals | The total number of 8 animals divided into 2 groups containing 4 animals (2M + 2F) per group. |

Study Design:

| S. No. | Group | Dose (in mg/kg) | Dose (in mL/kg) | Route | Duration of treatment | No. of animals |
|---|---|---|---|---|---|---|
| 1 | Reference item (DECA-DURABOLIN) | 18 | 0.18 | IM | Single dose | 4 (2M + 2F) |
| 2 | Test item (Nandrolone Decanoate injection) | 18 | 0.18 | IM | Single dose | 4 (2M + 2F) |

Experimental Procedure: After administration of test and reference item by intramuscular route mark will be made at injection site so that every time the pain sensitivity will be observed same site.

Results: There were no significant pain sensitivity observed at Nandrolone Decanoate injected site compared with DECA-DURABOLIN at 15, 30 Min. 1, 2, 4 hrs. DECA-DURABOLIN injected animals observed with slightly higher pain compared with Progesterone injection.

Measurement of Pain Sensitivity (Threshold) at Methyl Prednisolone Injection Site in Wistar Rats by Intramuscular Route The aim of the study 1 to evaluate pain sensitivity at Methyl Prednisolone injection site and comparison with reference

| Details of Test System: | |
|---|---|
| Species | Rat (Wistar) |
| Animal age | 6-8 weeks |
| Number of Animals | The total number of 8 animals divided into 2 groups containing 4 animals (2M + 2F) per group. |

Study Design:

| S. No. | Group | Dose (in mg/kg) | Dose (in mL/kg) | Route | Duration of treatment | No. of animals |
|---|---|---|---|---|---|---|
| 1 | Reference item (DEPO-MEDROL) | 7.2 | 0.17 | IM | Single dose | 4 (2M + 2F) |
| 2 | Test item (Methyl Prednisolone injection) | 7.2 | 0.17 | IM | Single dose | 4 (2M + 2F) |

Experimental Procedure: After administration of test and reference item by intramuscular route mark will be made at injection site so that every time the pain sensitivity will be observed same site.

Results: There were no significant pain sensitivity observed at Methyl Prednisolone injected site compared with DEPO-MEDROL at 15, 30 Min. 1, 2, 4 hrs. DEPO-MEDROL injected animals observed with slightly higher pain compared with Methyl Prednisolone injection.

Measurement of Pain Sensitivity at Paracetamol Injection Site in Wistar Rats by Intramuscular Route The aim of the study is to evaluate pain sensitivity at paracetamol injection site and comparison with reference

| Details of Test system | |
|---|---|
| Species | Rat (Wistar) |
| Animal age | 6-8 weeks |
| Number of animals | The total number of 8 animals divided in to 2 group containing 4 animals (2M + 2F) per group |

Study Design:

| S. No. | Group | Dose (in mg/kg) | Dose (in mL/kg) | Route | Duration of treatment | No. of animals |
|---|---|---|---|---|---|---|
| 1 | Reference item (febtinil) | 27 | 0.18 | IM | Single dose | 4 (2m + 2F) |
| 2 | Test item (Paracetamol injection 150 g/ml) | 27 | 0.18 | IM | Single dose | 4 (2m + 2F) |

Experimental Procedure: After administration of test and reference item by intramuscular route mark all be made at injection site so that every time the pain sensitivity will be observed same site Results: There were no significant pain sensitivity observed a paracetamol injection 150 mg/ml injected site compared with Febrinil at 15.30 Min 1, 2, 4 hrs, Febrinil injected animal observed with slightly higher pain compared with paracetamol injection 150 mg/mL injection.

Measurement of Pain Sensitivity (Threshold) at Pantoprazole Injection Site in Wistar Rats by Intravenous Route Study Design:

| Details of Test system | |
|---|---|
| Species | Rat (Wistar) |
| Animal age | 6-8 weeks |
| Number of animals | The total number of 8 animals divided into 2 group containing 4 animals (2M + 2F) per group |

| S. No. | Group | Dose (in mg/kg) | Dose (in mL/kg) | Route | Duration of treatment | No. of animal |
|---|---|---|---|---|---|---|
| 1 | Reference item (Pantrodac i.v) | 3.6 | 0.9 | IV | Single dose | 4 (2m + 2F) |

-continued

| S. No. | Group | Dose (in mg/kg) | Dose (in mL/kg) | Route | Duration of treatment | No. of animal |
|---|---|---|---|---|---|---|
| 2 | Test item (Pantoprazole injection) | 3.6 | 0.9 | IV | Single dose | 4 (2m + 2F) |

Experimental Procedure: After administration of test and reference item by intravenous route mark all be made at injection site so that every time the pain sensitivity will be observed same site Results: There were no significant pain sensitivity observed at Pantoprazole Injected site compared with Pantodac i.v at 15.30 Min 1, 2, 4 hrs, Pantodac i.v injected animals observed with slightly higher pain compared with Pantoprazole injection.

We claim:

1. An injectable pharmaceutical composition comprising Vitamin D3 in an amount of 0.1 to 33.33 mg/ml of diethylene glycol monoethyl ether, diethylene glycol monoethyl ether in amount of 25% to 30% by weight of the composition, BHA in an amount of 0.001 to 2% by weight of the composition, and vitamin E acetate.

2. The pharmaceutical composition according to claim 1, further comprising one or more of a preservative, buffering agent, antioxidant, chelating agent, stabilizer, co-solvent and other excipients.

3. The pharmaceutical composition according to claim 1, formulated for intravenous, intramuscular, subcutaneous or ocular administration.

4. The pharmaceutical composition according to claim 1, wherein the pharmaceutical active is not milled or micronized prior to use.

5. The pharmaceutical composition according to claim 2, wherein the buffering agent is selected from 0.1 N Sodium hydroxide, Acetic acid, Sodium citrate, Potassium chloride, Sodium chloride, Citric acid, Sodium bicarbonate, L-Arginine, Tris buffers, Cholic acid Derivatives, and Amino acid Derivatives.

6. The pharmaceutical composition according to claim 2, wherein the preservative is selected from Benzyl alcohol, Methyl paraben, Propyl paraben, Thimerosal, Phenyl mercuric salts (acetate, borate, nitrate), Chlorobutanol, and Meta-cresol.

7. The pharmaceutical composition according to claim 2, wherein the antioxidant is selected from Ascorbic acid, Ascorbyl palmitate, Thioglycerol and its derivatives, Sodium bisulphate, Sodium metabisulphite, Sodium formaldehyde sulphoxylate, Thiourea, Ascorbic acid ester, Butylated hydroxyl toluene and Tocopherols.

8. The pharmaceutical composition according to claim 2, wherein the preservative is present in an amount of 0.001% to 2% by weight of the composition.

9. The pharmaceutical composition according to claim 2, wherein the antioxidant is present in an amount of 0.004% to 2% by weight of the composition.

10. The pharmaceutical composition according to claim 2, wherein the chelating agent is Ethylene diamine tetraacetic acid, and is present in an amount of 0.01% to 0.075% by weight of the composition.

11. The pharmaceutical composition according to claim 2, wherein the stabilizer is maleic acid or a malate salt.

* * * * *